United States Patent
Burnett et al.

(10) Patent No.: US 7,504,391 B2
(45) Date of Patent: Mar. 17, 2009

(54) SELECTIVE $D_1/D_5$ RECEPTOR ANTAGONISTS FOR THE TREATMENT OF OBESITY AND CNS DISORDERS

(75) Inventors: Duane A. Burnett, Bernardsville, NJ (US); William J. Greenlee, Teaneck, NJ (US); Brian McKittrick, New Vernon, NJ (US); Jing Su, Scotch Plains, NJ (US); Zhaoning Zhu, Plainsboro, NJ (US); Thavalakulamgara K. Sasikumar, Westfield, NJ (US); Robert Mazzola, Clinton, NJ (US); Li Qiang, Fords, NJ (US); Yuanzan Ye, Iselin, NJ (US)

(73) Assignee: Schering Corporation, Kenilworth, NJ (US)

( * ) Notice: Subject to any disclaimer, the term of this patent is extended or adjusted under 35 U.S.C. 154(b) by 477 days.

(21) Appl. No.: 10/850,530

(22) Filed: May 20, 2004

(65) Prior Publication Data

US 2005/0075325 A1    Apr. 7, 2005

Related U.S. Application Data

(60) Provisional application No. 60/472,534, filed on May 22, 2003.

(51) Int. Cl.
*A61P 1/00* (2006.01)
*A61K 31/55* (2006.01)
*C07D 223/14* (2006.01)
*C07D 223/16* (2006.01)

(52) U.S. Cl. .................. 514/213.01; 514/217.02; 540/576; 540/595

(58) Field of Classification Search ............ 514/213.01, 514/217.02; 540/576, 595
See application file for complete search history.

(56) References Cited

U.S. PATENT DOCUMENTS

| | | | |
|---|---|---|---|
| 4,104,379 A | 8/1978 | Gallagher, Jr. et al. . | 514/217.02 |
| 4,707,483 A | 11/1987 | Bondinell et al. ........... | 514/273 |
| 5,440,033 A | 8/1995 | Berger et al. .................. | 540/549 |

FOREIGN PATENT DOCUMENTS

| | | |
|---|---|---|
| EP | 0 127 423 | 5/1984 |
| EP | 0 244 088 | 3/1987 |
| EP | 0 285 919 | 3/1988 |

OTHER PUBLICATIONS

Wen-Lian Wu et al., Dopamine D1/D5 Receptor Antagonists with Improved Pharmacokinetics: Design, Synthesis, and Biological Evaluation and Phenol Bioisosteric Analogues of Benzazepine D1/D5 Antagonists, *J. Med. Chem* 2005, 48:680-693.

Tamagnan et al., Cyclopentadienyltricarbonylrheniumbenzazepines: Synthesis and binding affinity, *Bioorg. Med. Chem. Lett* 2000, 10(10): 1113-1115.

Theresa M. Filtz et al., Synthesis and Applications of an Aldehyde-Containing Analogue of SCH-23390, *Bioconjugate Chem.* 1990, 1: 394-399.

M. A. Rehman et al., Azabenzocycloheptenones. Part VI. * Preparation and Some Reactions of 1,2,4,5-Tetrahydro-1-oxo-3-toluene-*p*-sulphonylbenz[*d*]azepine, *J. Chem. Soc.* 1967 58-61.

Eric Hollander et al., Obsessive-Compulsive and Spectrum Disorders: Overview and Quality of Life Issues, *J. Clin. Psychiatry* 1996, 8: 3-6.

Katharine A. Phillips, Body Dysmorphic Disorder: Diagnosis and Treatment and Imagined Ugliness, *J. Clin. Psychiatry* 1996, 8: 61-64.

Gary Christenson et al., Trichotillomania Rational Treatment Options, *CNS Drugs* 1996 6:1 23-34.

Turkel R. Keser et al., Comparison of Clinical Characteristics in Trichotillomania and Obsessive-Compulsive Disorder, *Journal of Anxiety Disorders* 2001 15:5 433-441.

P. L. du Toit et al., Characteristics and Phenomenology of Hair-pulling; and exploration of subtypes, *Comprehensive Psychiatry* 2001, 42:3 247-256.

*Primary Examiner*—Brenda L Coleman
(74) *Attorney, Agent, or Firm*—Palaiyur S. Kalyanaraman; Willaim Y. Lee

(57) ABSTRACT

The present invention provides compounds, which, are novel antagonists for $D_1/D_5$ receptors as well as methods for preparing such compounds. In another embodiment, the invention provides pharmaceutical compositions comprising such $D_1/D_5$ receptor antagonists as well as methods of using them to treat CNS disorders, obesity, metabolic disorders, eating disorders such as hyperphagia, and diabetes.

26 Claims, No Drawings

SELECTIVE $D_1/D_5$ RECEPTOR ANTAGONISTS FOR THE TREATMENT OF OBESITY AND CNS DISORDERS

CROSS REFERENCE TO RELATED APPLICATIONS

This application claims the benefit of U.S. Provisional Application No. 60/472,534 filed on May 22, 2003.

FIELD OF THE INVENTION

The present invention relates to compounds useful as $D_1/D_5$ receptor antagonists, pharmaceutical compositions containing the compounds, and methods of treatment using the compounds and compositions to treat obesity, metabolic disorders and CNS disorders.

BACKGROUND OF THE INVENTION

Considerable research has been directed at controlling obesity, nicotine addiction and substance abuse. The cost to society is very high from the health costs associated with obesity and addictions. Accordingly, it would be desirable to provide a substance that would suppress cravings for food, and other substances in a predisposed patient.

Substances, which are administered to reduce craving should not produce significant physiological effects, such as stimulation of mood or elevation of blood pressure or heart rate. This could result in the substitution of one abused substance for another. Compounds that dampen the desire for the abused substance, also should not exacerbate the physiological symptoms of the abused substance in the event the individual relapses and takes the abused substance. Substances administered to reduce craving also should not produce significant adverse effects, such as dysphoria, restlessness or stiffness.

In addition to obesity and the disorders listed above, there is a strong need for drug therapy which can effectively treat, ameliorate and prevent central nervous system (CNS) disorders such as obsessive compulsive disorder, somatoform disorders, dissociative disorders, eating disorders, impulse control disorders, trichotillomania and autism. Obsessive-compulsive disorder ("OCD"), recognized to be among the most common of all psychiatric disorders, occurs in 2 to 3% of the U.S. population. OCD is characterized by anxiety-provoking and intrusive thoughts (e.g., fear of contamination and germs, doubt and uncertainty about future harm, need for symmetry, etc.), which lead to ritualistic and/or irrational behavior (e.g., constant checking, washing, touching, counting, etc.). See Hollander, et al., J. Clin. Psychiatry 57 (Suppl. 8), pp. 3-6 (1996).

Somatoform disorders (e.g., body dysmorphic disorder and hypochondriasis) are characterized by abnormal preoccupation with one's appearance or physical condition. For example, body dysmorphic disorder is a preoccupation with an imagined or slight defect in appearance. Many sufferers of body dysmorphic disorder are severely debilitated by their abnormal preoccupation, with significant impairment in social, occupational, or other important aspects of daily life. See Phillips, J. Clin. Psychiatry 57 (suppl. 8), pp. 61-64 (1996). Hypochondriasis is characterized by a persistent conviction that one is, or is likely to become ill. Many hypochondriacs are unable to work or engage in ordinary activities due to their preoccupation with illness.

Dissociative disorders (e.g., depersonalization) are characterized by sudden temporary alterations in identity, memory, or consciousness, segregating normally integrated memories or parts of the personality from the dominant identity of the individual. Depersonalization disorder, which is a dissociative disorder, is characterized by one or more episodes of depersonalization (feelings of unreality and strangeness in one's perception of the self or one's body image).

Eating disorders (e.g., anorexia nervosa, bulimia, and binge eating) are characterized by abnormal compulsions to avoid eating or uncontrollable impulses to consume abnormally large amounts of food. These disorders affect not only the social well-being, but also the physical well-being of sufferers.

Impulse control disorders (e.g., pathological gambling, compulsive buying, sexual compulsions and kleptomania) are characterized by a preoccupation with, and an inability to refrain from repeatedly engaging in various behaviors that are either socially unacceptable, or abnormally excessive by societal norms.

Trichotillomania is a habitual hair pulling that usually appears in children. See Merck Index, $15^{th}$ Edition (1987); Christenson, Gary; O'Sullivan, Richard, Trichotillomania: Rational treatment options, CNS Drugs (1996), 6(1), 23-34; Tukel R; Keser V; Karali N T; Olgun T O; Calikusu C., Comparison of clinical characteristics in trichotillomania and obsessive-compulsive disorder, JOURNAL OF ANXIETY DISORDERS (September-October 2001), 15(5), 433-41; du Toit P L; van Kradenburg J; Niehaus D J; Stein D J, Characteristics and phenomenology of hair-pulling: an exploration of subtypes, COMPREHENSIVE PSYCHIATRY (May-June 2001), 42(3), 247-56.

Autism is a disorder characterized by a preoccupation with one's own self and a severe impairment of the ability to perceive or react to outside stimuli in a normal fashion. Many autistics are incapable of even communicating with others.

In view of the tragic and debilitating effects of these disorders, there is a strong need for a drug therapy which can effectively treat such disorders.

SUMMARY OF THE INVENTION

In its many embodiments, the present invention provides a novel class of compounds as $D_1/D_5$ receptor antagonists, methods of preparing such compounds, pharmaceutical compositions comprising one or more such compounds, methods of preparing pharmaceutical compositions or formulations comprising one or more such compounds, and methods of treatment, prevention, inhibition or amelioration of obesity, metabolic disorders, CN,S disorders or one or more diseases associated with obesity using such compounds or pharmaceutical compositions.

In one aspect, the present application provides a compound, or a pharmaceutically acceptable salt or solvate of said compound, said compound having the general structure shown in formula I:

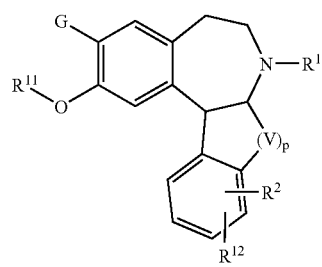

or a pharmaceutically acceptable salt or solvate of said compound, isomer or racemic mixture wherein p is 0, 1 or 2 and when p is 0, the carbons to which $(V)_p$ is shown connected are not linked to each other but are each linked to a hydrogen atom;

G is hydrogen, halogen, alkyl, alkylthio, nitro, nitrile, hydroxy, alkoxy, alkylsulfinyl, alkylsulfonyl, trifluoromethyl or trifluromethoxy;

V is —C(alkyl)$_2$-, —CH(alkyl)- or —CH$_2$—;

$R^1$ is hydrogen, alkyl, allyl, cycloalkyl or cycloalkyl(alkyl);

$R^2$ is one substituent selected from the group consisting of trifluoromethoxy, aryl, —NO$_2$, —NR$^5$R$^6$, —(CH$_2$)$_{1-6}$—NR$^5$R$^6$, —N(R$^6$)C((R$^7$)(R$^8$))C(O)R$^8$, —CN, heteroaryl, —C(O)R$^8$, —C(O)OR$^8$, —C(O)NR$^3$R$^4$, —S(O)$_2$NR$^3$R$^4$, —C(R$^7$)(R$^8$)NR$^5$R$^6$, —C(R$^7$)=NOR$^4$ and —C(R$^7$)(R$^8$)OR$^6$;

$R^3$ and $R^4$ are aryl, aralkyl, alkenyl, heterocyclyl, heteroaryl, cycloalkyl, cycloalkylalkyl, heteroaralkyl, heterocyclylalkyl, alkyl or hydrogen, or $R^3$, $R^4$ and the N to which they are attached can be joined together to form a ring selected from the group consisting of azetidine, azepane, indane, pyrrolidine, piperidine, piperazine, morpholine and

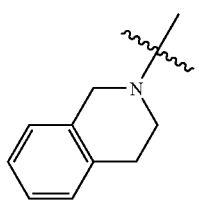

wherein said ring is unsubstituted or optionally substituted with one to four $R^{10}$ moieties;

$R^5$ is hydrogen, alkyl, alkenyl, aryl, aralkyl, cycloalkyl, heteroaralkyl, —C(O)NR$^3$R$^4$, —S(O)$_2$NR$^3$R$^4$, —S(O)$_2$R$^8$, —C(O)R$^8$, —C(O)OR$^8$ or —R$^9$;

$R^6$ is hydrogen, alkyl, aryl, aralkyl, cycloalkyl, cycloalkylalkyl, heteroaralkyl, heterocyclylalkyl, heterocyclyl or heteroaryl, or $R^5$, $R^6$ and the N to which they are attached can be joined together to form a ring selected from the group consisting of azetidine, azepane, indane, pyrrolidine, piperidine, piperazine, morpholine and

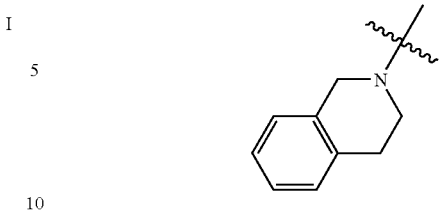

wherein said ring is unsubstituted or optionally substituted with one to four $R^{10}$ moieties;

$R^7$ is hydrogen, alkyl, aryl or aralkyl;

$R^8$ is hydrogen, aryl, alkyl, aralkyl, cycloalkyl, cycloalkylalkyl, heterocyclyl or heteroaryl;

$R^9$ is alkoxyalkyl, alkoxyaryl, alkoxyheteroaryl or alkoxyaralkyl;

$R^{10}$ is 1 to 4 substituents which can be the same or different, each $R^{10}$ being independently selected from the group consisting of alkyl, aryl, aralkyl, heteroaryl, heteroaralkyl, hydroxy, hydroxyalkyl, alkoxy, aryloxy, aralkoxy, acyl, aroyl, halogen, nitro, cyano, carboxy, alkoxycarbonyl, alkoxycarbonylalkylenyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, trifluoromethyl, $Y_1Y_2N$—, $Y_1Y_2N$-alkyl-, $Y_1C(O)N$—, $Y_1Y_2NC(O)$— and $Y_1Y_2NS(O)_2$—, wherein $Y_1$ and $Y_2$ may be the same or different and are independently selected from the group consisting of hydrogen, alkyl, aryl, and aralkyl or two $R^{10}$ groups on adjacent carbons can be joined together to form a methylenedioxy or ethylenedioxy group;

$R^{11}$ is hydrogen or alkyl; and $R^{12}$ is one to three substituents which can be the same or different, each $R^{12}$ being independently selected from the group consisting of $R^2$, halogen, alkyl, alkylthio, alkylsulfonyl, hydroxy, alkoxy and trifluoromethyl;

wherein each of said alkyl, allyl, alkylene, alkylenyl, heteroalkylene, aryl, aralkyl, alkoxy, aryloxy, aralkoxy, acyl, aroyl, aryloxyalkyl, hydroxyalkyl, alkoxyalkyl, heteroaralkyl, heterocyclyl, heterocyclylalkyl, heteroaryl, heteroaralkyl, hydroxy, hydroxyalkyl, cycloalkylalkyl, heterocyclyl and cycloalkyl is unsubstituted or optionally substituted with one to four $R^{10}$ moieties, where two adjacent $R^{10}$ groups can be joined together to form a methylenedioxy or ethylenedioxy group.

The compounds of formula I can be useful as $D_1/D_5$ receptor antagonists and can be useful in the treatment of CNS disorders, metabolic disorders such as obesity and eating disorders such as hyperphagia. Another embodiment of this invention is directed to pharmaceutical compositions for the treatment of obesity which comprise an obesity treating amount of a compound of formula I, or a pharmaceutically acceptable salt of said compounds, and a pharmaceutically acceptable carrier therefore.

DETAILED DESCRIPTION OF THE INVENTION

In one embodiment, the present invention provides compounds which are represented by structural formula I, or a pharmaceutically acceptable salt or solvate thereof, wherein the various moieties are as described above.

In additional preferred embodiments of the above formula I with the structure:

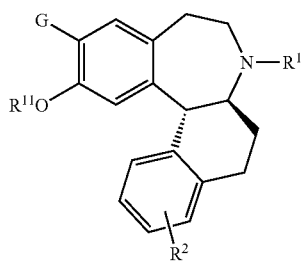

wherein G, $R^1$, $R^2$ and $R^{11}$ are defined above.

Additional preferred embodiments of formula I include compounds wherein: G is halogen, $R^1$ is alkyl and $R^{11}$ is hydrogen. Compounds represented by formula I wherein G is chloro, $R^1$ is methyl are also preferred.

Still additional preferred embodiments of formula I include compounds wherein:
$R^2$ is —$CH_2$—$NR^5R^6$;
$R^5$ is hydrogen;
and $R^6$ is

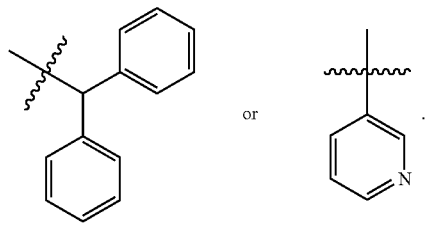

Still additional preferred embodiments of formula I include compounds wherein:
$R^2$ is —$CH_2$—$NR^5 R^6$;
$R^5$ is $C(O)CH_3$;
and $R^6$ is

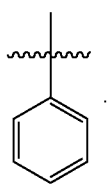

Still additional preferred embodiments of formula I include compounds wherein:
$R^2$ is —$CH_2$—$NR^5R^6$;
$R^5$ is benzyl;
and $R^6$ is

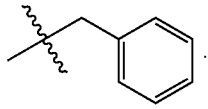

Still additional preferred embodiments of formula I include compounds wherein:
$R^2$ is —$CH_2$—$NR^5R^6$;
$R^5$ is —$S(O)_2$-methyl;
and $R^6$ is

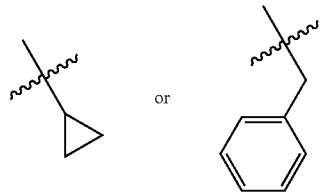

Still additional preferred embodiments of formula I include compounds wherein:
$R^2$ is —$CH_2$'$NR^5R^6$;
$R^5$ is —$C(O)NH$-ethyl;
and $R^6$ is

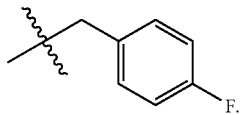

Still additional preferred embodiments of formula I include compounds wherein:
$R^2$ is —$CH_2$—$NR^5R^6$;
$R^5$ is —$C(O)NH$-isopropyl;
and $R^6$ is

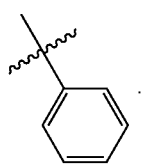

Still additional preferred embodiments of formula I include compounds wherein $R^2$ is selected from the group consisting of:

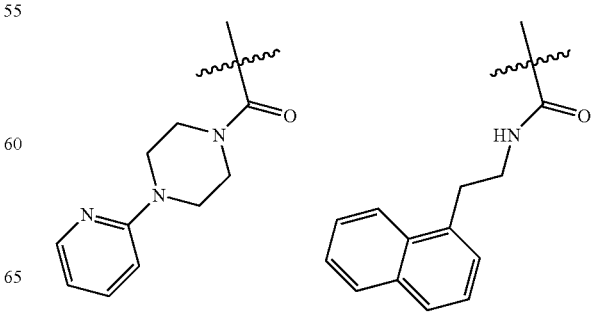

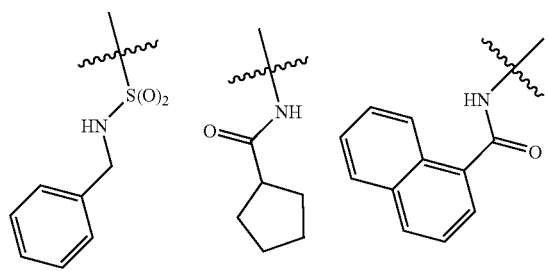
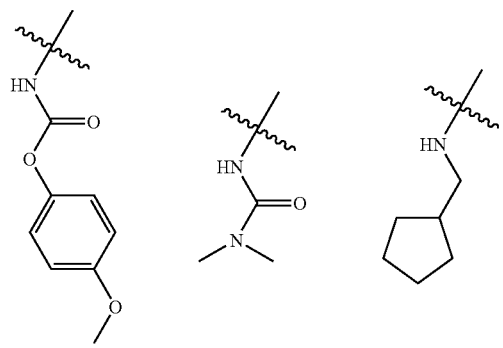
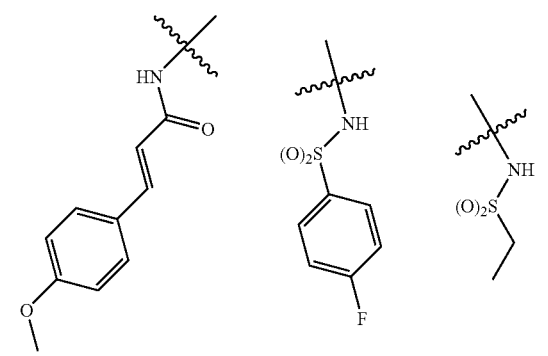
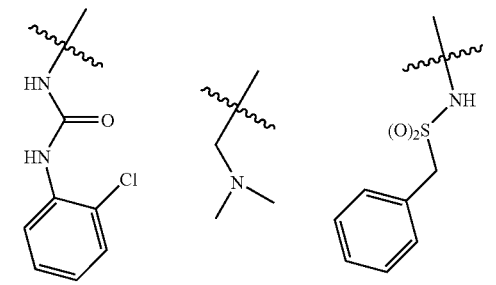
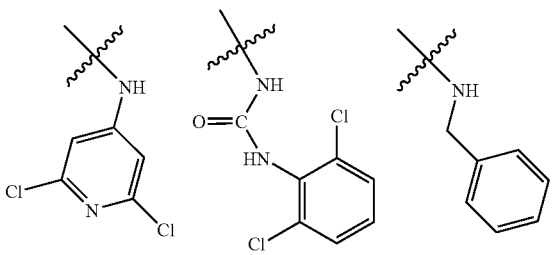
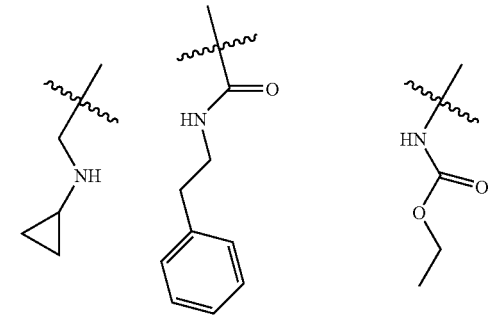
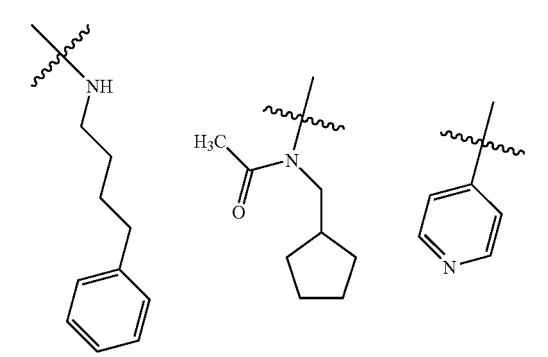
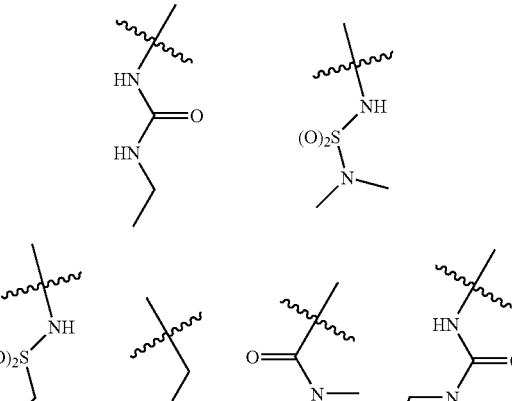
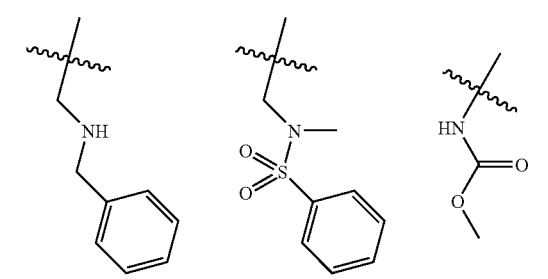
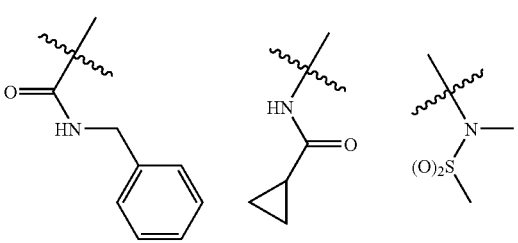

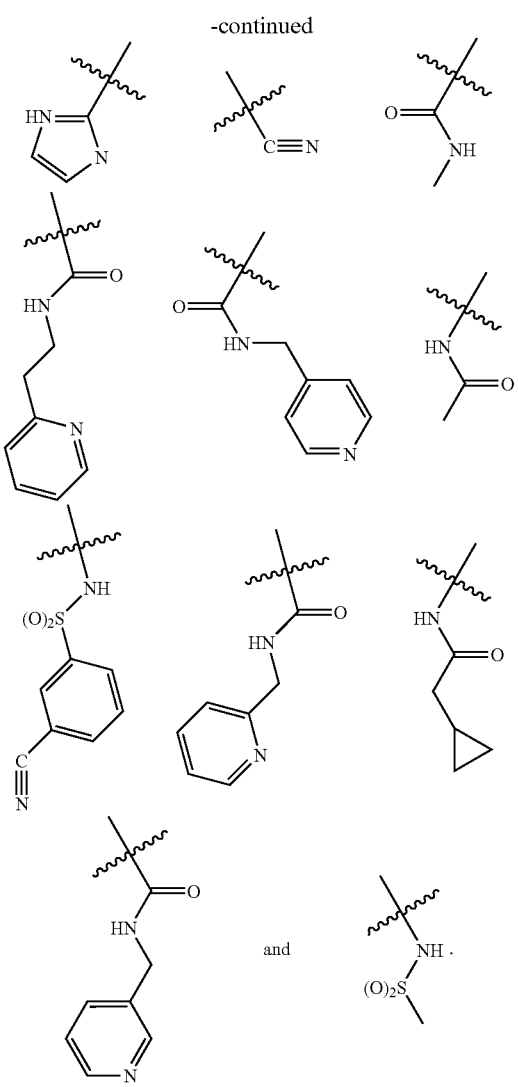

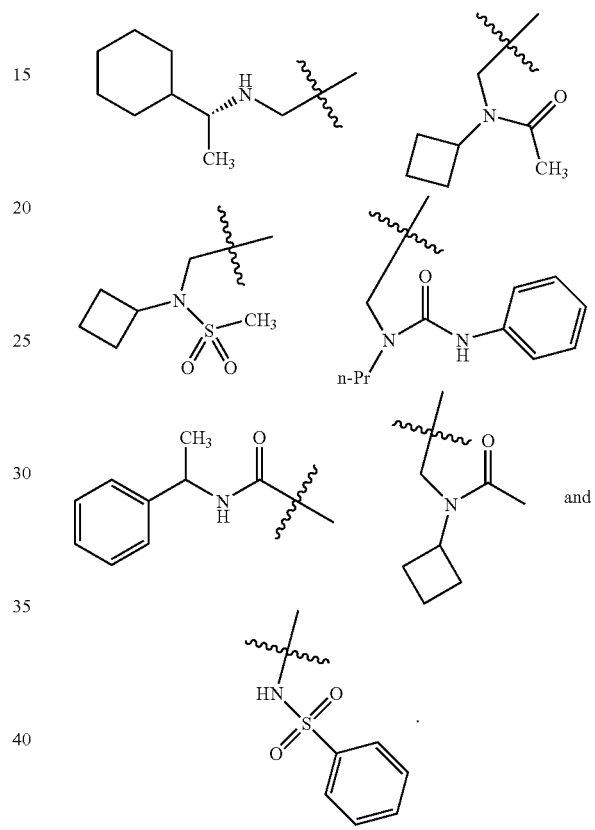

Still yet another class of preferred compounds of the above formula I has the structure:

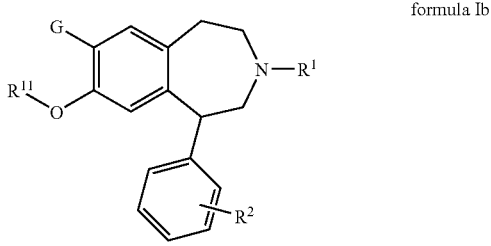

formula Ib wherein G, $R^1$, $R^2$ and $R^{11}$ are defined above.

In still another class of preferred compounds of formula Ib wherein: G is halogen, $R^1$ is alkyl and $R^{11}$ is hydrogen. Compounds represented by formula Ib wherein G is chloro, $R^1$ is methyl are also preferred.

Still yet another class of preferred compounds of formula Ib wherein $R^2$ is —$NR^5R^6$ is $R^5$ is alkyl, alkenyl, aryl, aralkyl, cycloalkyl, heteroaralkyl, —C(O)$NR^3R^4$, —S(O)$_2R^8$ or —C(O)$R^8$;

and
$R^6$ is hydrogen, alkyl, aryl, aralkyl, cycloalkyl, cycloalkylalkyl, heteroaralkyl, heterocyclylalkyl, heterocyclyl or heteroaryl, or $R^5$, $R^8$ and N in —$NR^5R^6$ together can be joined together to form a ring selected from the group consisting of azetidine, pyrrolidine, piperidine, piperazine, and morpholine wherein said ring is unsubstituted or optionally substituted with one or more $R^{10}$ moieties.

Still yet another class of preferred compounds of formula I wherein p is 0 and $R^2$ is selected from the group consisting of:

Preferred compounds of formula I include but are not limited to Examples: 5a1, 5a14, 5a38, 5a50, 5b46, 5c16, 6a6, 6b1, 6c26, 7b7, 7c16, 7c18, 8b11, 8a3, 8c33, 13a2, 13a6, 13a7, 13a12, 13a14, 13a16, 13a19, 13a20, 13a21, 13a24, 13d1, 14t, 15l, 18a1, 18a4, 18a6, 18a8, 18b15, 19a6, 19b1, 19b5, 19b23, 19b31, 19b24, 19b32, 20a7, 20a8, 20a33, 20b5, 20b6, 20b30, 21a1, 21a2, 22a2, 22b1, 23, 24a1, 24a2, 24a3, 24b2, 25c, 27a, 29c, 30a, 34a2, 35a2 and 35a1.

The compounds of formula I can be administered as racemic mixtures or enantiomerically pure compounds.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of alkyl, aryl, aralkyl, heteroaryl, heteroaralkyl, hydroxy, hydroxyalkyl, alkoxy, aryloxy, aralkoxy, acyl, aroyl, halogen, nitro, cyano, carboxy, alkoxycarbonyl, alkoxycarbonylalkylenyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, trifluoromethyl, $Y_1Y_2N-$, $Y_1Y_2N$-alkyl-, $Y_1C(O)N-$, $Y_1Y_2NC(O)-$ and $Y_1Y_2NS(O)_2-$, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group. Non-limiting examples of suitable alkyl groups include methyl, ethyl, n-propyl, isopropyl and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of alkyl, aryl, aralkyl, heteroaryl, heteroaralkyl, hydroxy, hydroxyalkyl, alkoxy, aryloxy, aralkoxy, acyl, aroyl, halogen, nitro, cyano, carboxy, alkoxycarbonyl, alkoxycarbonylalkylenyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, trifluoromethyl, $Y_1Y_2N-$, $Y_1Y_2N$-alkyl-, $Y_1C(O)N-$, $Y_1Y_2NC(O)-$ and $Y_1Y_2NS(O)_2-$, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group. Non-limiting examples of suitable alkenyl groups include ethenyl, propenyl, and n-butenyl.

"Alkylene" or "alkylenyl" means an alkanediyl group commonly having free valencies on two carbon atoms. Non-limiting examples include methylene, ethylene, propylene and the like. The term "substituted alkylene" means that the alkylene group may be substituted by one or more substituents which may be the same or different, each substituent being independently selected from the group consisting of alkyl, aryl, aralkyl, heteroaryl, heteroaralkyl, hydroxy, hydroxyalkyl, alkoxy, aryloxy, aralkoxy, acyl, aroyl, halogen, nitro, cyano, carboxy, alkoxycarbonyl, alkoxycarbonylalkylenyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, trifluoromethyl, $Y_1Y_2N-$, $Y_1Y_2N$-alkyl-, $Y_1C(O)N-$, $Y_1Y_2NC(O)-$ and $Y_1Y_2NS(O)_2-$, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group.

"Aryl" means an aromatic monocyclic or bicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or bicyclic ring system comprising about 5 to about 14 ring atoms, preferably about 5 to about 10 ring atoms, in which one or more of the ring atoms is an element other than carbon, for example nitrogen, oxygen or sulfur, alone or in combination. There are no adjacent oxygen and/or sulfur atoms present in the ring system. Preferred heteroaryls contain about 5 to about 6 ring atoms. The "heteroaryl" can be optionally substituted by one or more "ring system substituents" which may be the same or different, and are as defined herein. The ring system substituents can be attached to the nitrogen, oxygen and sulfur. The prefix aza, oxa or thia before the heteroaryl root name means that at least one nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or bicyclic ring system comprising about 3 to about 10 carbon atoms, preferably about 3 to about 10 carbon atoms. Preferred cycloalkyl rings contain about 3 to about 7 ring atoms. Included in the definition of heterocyclyl are benzo-fused cycloalkyls such as

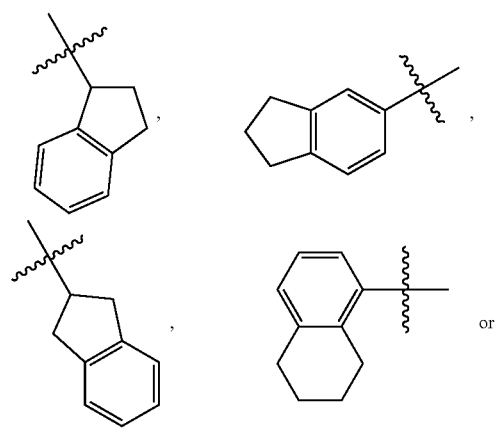

or

-continued

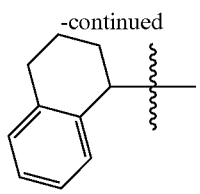

Benzo-fused cycloalkyls can be attached to the parent moiety either through the saturated or unsaturated portions of the ring. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable bicyclic cycloalkyls include 1-decalinyl, norbornyl, adamantyl and the like.

"Cycloalkylalkyl" means a cycloalkylalkyl group. Non-limiting examples of suitable cycloalkylalkyl groups include cyclopropylmethyl and cyclopropylethyl. The bond to the parent moiety is through the alkyl.

"Heterocyclyl" means a non-aromatic saturated monocyclic or bicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Included in the definition of heterocyclyl are benzo-fused heterocyclyls such as

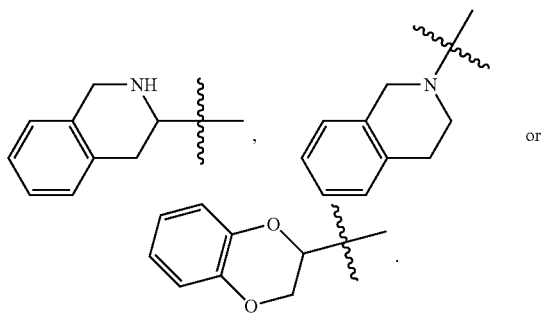

Benzo-fused heterocyclyls can be attached to the parent moiety either through the saturated or unsaturated portions of the ring. There are no adjacent oxygen and/or sulfur atoms present in the ring system. Preferred heterocyclyls contain about 5 to 7 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, pyrrolidonyl, tetrahydrothiophenyl, azepanyl and the like.

"Heterocyclylalkyl" means a heterocyclyl-alkyl group. Non-limiting examples of suitable heterocyclylalkyl groups include piperidinylmethyl and piperazinylmethyl. The bond to the parent moiety is through the alkyl.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system, which, for example, replaces an available hydrogen on the ring system. Ring system substituents may be the same or different, each being independently selected from the group consisting of alkyl, aryl, aralkyl, heteroaryl, heteroaralkyl, hydroxy, hydroxyalkyl, alkoxy, aryloxy, aralkoxy, acyl, aroyl, halogen, nitro, cyano, carboxy, alkoxycarbonyl, alkoxycarbonylalkylenyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, trifluoromethyl, $Y_1Y_2N-$, $Y_1Y_2N$-alkyl-, $Y_1C(O)N-$, $Y_1Y_2NC(O)-$ and $Y_1Y_2NS(O)_2-$, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the oxygen.

"Aralkoxy" means an aralkyl-O— group. Non-limiting example of a suitable aralkoxy group is benzyloxy. The bond to the parent moiety is through the oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Heteroaralkylthio" means a heteroaralkyl-S— group in which the heteroaralkyl group is as previously described. The bond to the parent moiety is through the sulfur.

"Alkoxyalkyl" means an alkoxy-alkyl- group in which the alkoxy and alkyl groups are as previously described. The bond to the parent moiety is through the alkyl group.

"Alkoxyaryl" means an alkoxy-aryl- group in which the alkoxy and aryl groups are as previously described. The bond to the parent moiety is through the aryl group.

"Alkoxyheteroaryl" means an alkoxy-heteroaryl- group in which the alkoxy and heteroaryl groups are as previously described. The bond to the parent moiety is through the heteroaryl group.

"Alkoxyaralkyl" means an alkoxy-aralkyl- group in which the alkoxy and aralkyl groups are as previously described. The bond to the parent moiety is through the aralkyl group.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Alkoxycarbonylalkylenyl" means an alkyl-O—CO-alkylenyl group. Non-limiting examples of suitable alkoxycarbonylalkylenyl include ethoxycarbonylmethylenyl and methoxycarbonylmethylenyl. The bond to the parent moiety is through the alkylenyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Alkylsulfinyl" means an alkyl-S(O)— group. Preferred groups are those in which the alkyl group is lower alkyl. The bond to the parent moiety is through the sulfinyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Heteroarylsulfonyl" means a heteroaryl-S($O_2$)— group. The bond to the parent moiety is through the sulfonyl.

"Heteroarylthio" means a heteroaryl-S— group in which the heteroaryl group is as previously described. The bond to the parent moiety is through the sulfur.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in antagonizing the dopamine receptor and thus producing the desired therapeutic, ameliorative or preventative effect.

The compounds of formula I can form salts, which are also within the scope of this invention. Reference to the compounds of formula I herein is understood to include reference to salts thereof, unless otherwise indicated. The term "salt(s) ", as employed herein, denotes acidic salts formed with inorganic and/or organic acids, as well as basic salts formed with inorganic and/or organic bases. In addition, when compounds of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compounds of formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms-of the corresponding compounds for purposes of the invention.

Compounds of formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Compounds of formula I can have reduced potency at the Cytochrome P450 2D6 receptor and therefore can have reduced potential for affecting the metabolism of other drugs.

Compounds of formula I can be highly selective, high affinity $D_1/D_5$ receptor antagonists useful for the treatment of obesity.

Another aspect of this invention is a method of treating a patient (e.g., human) having a disease or condition therapeutically treated by administering a therapeutically effective amount of at least one compound of formula I, or a pharmaceutically acceptable salt or solvate, of said compound to the patient.

A useful dosage is about 0.001 to 100 mg/kg of body weight/day of the compound of formula I. A preferred dosage is about 0.01 to 25 mg/kg of body weight/day of a compound of formula I, or a pharmaceutically acceptable salt or solvate of said compound.

Another aspect of this invention is directed to a method of treating obesity comprising administering to a patient in need of such treatment a therapeutically effective amount of at least one compound of formula I, or a pharmaceutically acceptable salt or solvate of said compound.

Another aspect of this invention is directed to a method for treating eating and metabolic disorders such as bulimia or anorexia comprising administering to a patient a therapeutically effective amount of at least one compound of formula I, or a pharmaceutically acceptable salt or solvate of said compound.

Another aspect of this invention is directed to a method for treating hyperlipidemia comprising administering to a patient a therapeutically effective amount of at least one compound of formula I, or a pharmaceutically acceptable salt or solvate of said compound.

Another aspect of this invention is directed to a method for treating cellulite and fat accumulation comprising administering to a patient a therapeutically effective amount of at least one compound of formula I, or a pharmaceutically acceptable salt or solvate of said compound.

Another aspect of this invention is directed to a method for treating type II diabetes comprising administering to a patient a therapeutically effective amount of at least one compound of formula I, or a pharmaceutically acceptable salt or solvate of said compound.

In addition to the "direct" effect of the compounds of this invention on the $D_1/D_5$ receptor, there are diseases and conditions that can benefit from weight loss such as insulin resistance, impaired glucose tolerance, Type II Diabetes, hypertension, hyperlipidemia, cardiovascular disease, gall stones, certain cancers, and sleep apnea.

The compounds of formula I are expected to be useful in the therapy of a patient suffering from obsessive compulsive disorder, a somatoform disorder, a dissociative disorder, an eating disorder, an impulse control disorder, or autism by administering an effective amount of a compound of formula I, or salt or solvate thereof.

More specifically the compounds of formula I can be useful in the treatment of a variety of eating disorders including (but not limited to) anorexia nervosa, bulimia, and binge eating.

Compounds of formula I can be useful in the treatment of a variety of impulse control disorders including (but not limited to) pathological gambling, trichotillomania, compulsive buying, and sexual compulsion.

The compounds of the invention (i.e., the compounds of formula I) may also be used in combinations with other compounds as described below. Accordingly, another aspect of this invention is a method for treating obesity comprising administering to a patient (e.g., a female or male human)

a. an amount of a first compound, said first compound being a compound of the invention, a solvate thereof, or a pharmaceutically acceptable salt of said compound or of said solvate; and b. an amount of a second compound, said second compound being an anti-obesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a. a first compound, said first compound being a compound of the invention, a solvate thereof, or a pharmaceutically acceptable salt of said compound or of said solvate; and b. a second compound, said second compound being an anti-obesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a compound of the invention, a solvate thereof, or a pharmaceutically acceptable salt of said compound or of said solvate and a pharmaceutically acceptable carrier, vehicle or diluent in a first unit dosage form;

b. an amount of an anti-obesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred anti-obesity and/or anorectic agents (taken singly or in any combination thereof) in the above combination methods, combination compositions and combination kits include: phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a patient (e.g., a female or male human)

a. an amount of a first compound, said first compound being a compound of the invention, a solvate thereof, or a pharmaceutically acceptable salt of said compound or of said solvate; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of the invention, a solvate thereof, or a pharmaceutically acceptable salt of said compound or of said solvate; a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of the invention, a solvate thereof, or a pharmaceutically acceptable salt of said compound or of said solvate and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For combination treatment with more than one active agent, where the active agents are in separate dosage formulations, the active agents may be administered separately or in conjunction. In addition, the administration of one element may be prior to, concurrent to, or subsequent to the administration of the other agent.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The dosage regimen utilizing the compounds of formula I or their pharmaceutical compositions of the present invention, is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compounds of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.01 mg/kg to 500 mg/kg of bodyweight. The range is more particularly from about 0.01 mg/kg to 150 mg/kg of body weight per day or most particularly 0.01 mg/kg to 10 mg/kg.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following solvents and reagents may be referred to by their abbreviations in parenthesis:
Dimethylsulfoxide: DMSO
Butyl Lithium: BuLi
N-methyl pyrrolidinone: NMP
1-hydroxy-7-aza benzotriazole: HOAT
o-(7-azabenzotriazol-1-yl)-N,N,N',N'-tetramethyl uranium hexafluorophosphate: HATU
tetrabutyldimethylsilyl chloride: TBDMSCL
Reverse phase liquid chromatography mass spectroscopy: RP-LC MS
Triethylamine: Et$_3$N or TEA
1-(3-dimethylaminopropyl)-3-ethyl carbodiimide hydrochloride: EDCl
1-hydroxybenzotriazole: HOBt
trifluoroacetic acid: TFA
acetic acid: AcOH or HOAc
N,N-dimethylformamide: DMF
Acetonitrile: CH$_3$CN
Ethanol: EtOH
Methanol: MeOH
para-toluenesulfonic acid: p-TsOH
Tetrahydrofuran: THF
1,2-dichloroethane: DCE
Dichloromethane: DCM
Di-tert-butyl dicarbonate: (Boc)$_2$O
t-butyloxycarbonyl: -Boc
ethyl acetate: AcOEt or EtOAc
Thin layer chromatography: TLC or tlc
preparative thin layer chromatography: PTLC
Electrospray Mass Spectrum: ES MS
4-dimethylaminopyridine: DMAP
room temperature (ambient) about 25° C. (rt).

Experimental Procedures

Scheme 1

Method 1:

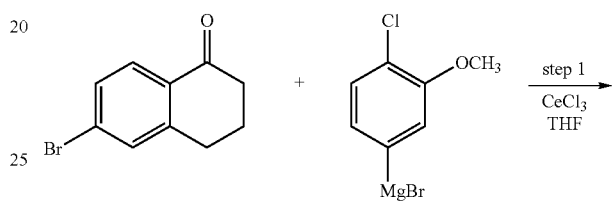

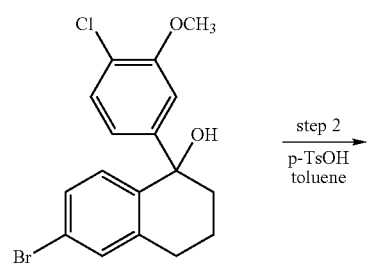

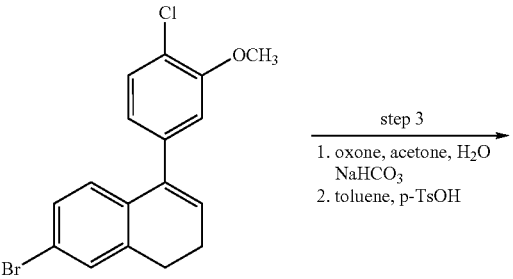

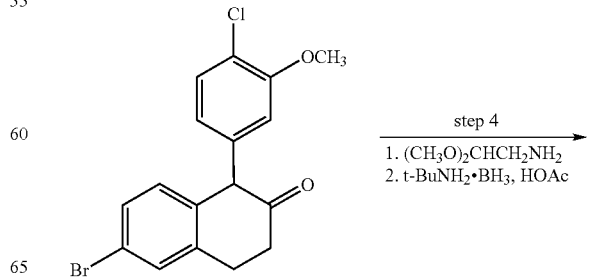

-continued

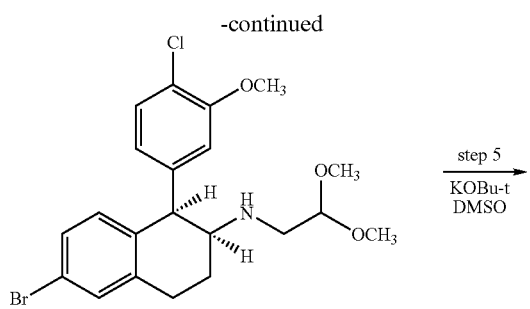

step 5
KOBu-t
DMSO

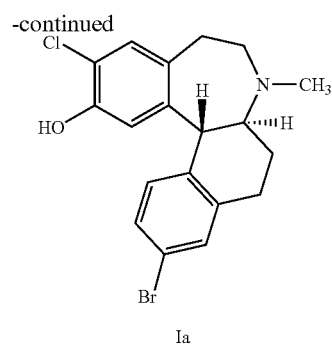
Ia

Compounds 3a and 3b can be prepared analogously starting with regioisomeric bromotetralones according to Scheme 1 or alternatively by the route shown in Scheme 2 starting with the known benzazepine ecopipam. (reference: J. G. Berger, W. K. Chang, J. W. Clader, D. Hou, R. E. Chipkin, A. T. McPhail *J. Med. Chem.* 1989, 32, 1913-1921)

Scheme 2

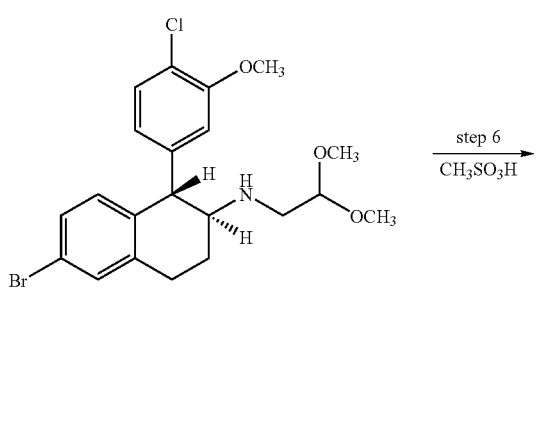

step 6
$CH_3SO_3H$

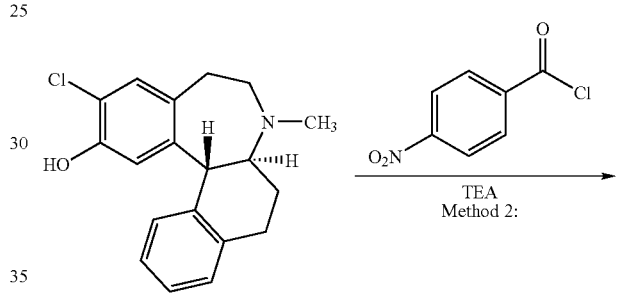

TEA
Method 2:

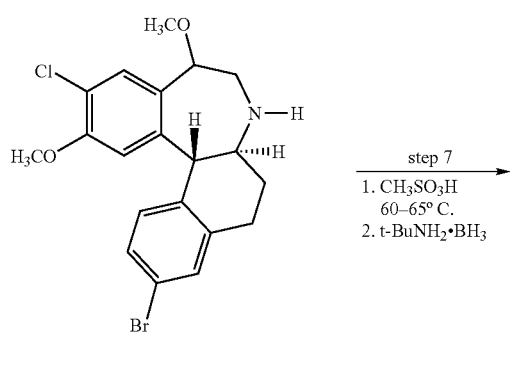

step 7
1. $CH_3SO_3H$
   60–65° C.
2. t-BuNH$_2$·BH$_3$

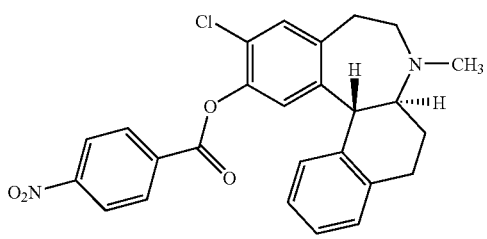
2a

Method 3 | 1. Br$_2$, Al$_2$O$_3$
         | 2. KOH

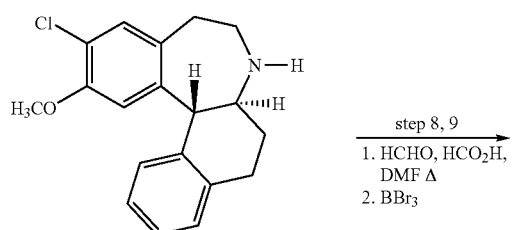

step 8, 9
1. HCHO, HCO$_2$H, DMF Δ
2. BBr$_3$

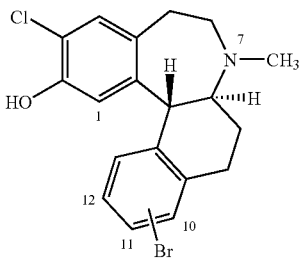

1a C-11-Br
3a C-10-Br
3b C-12-Br

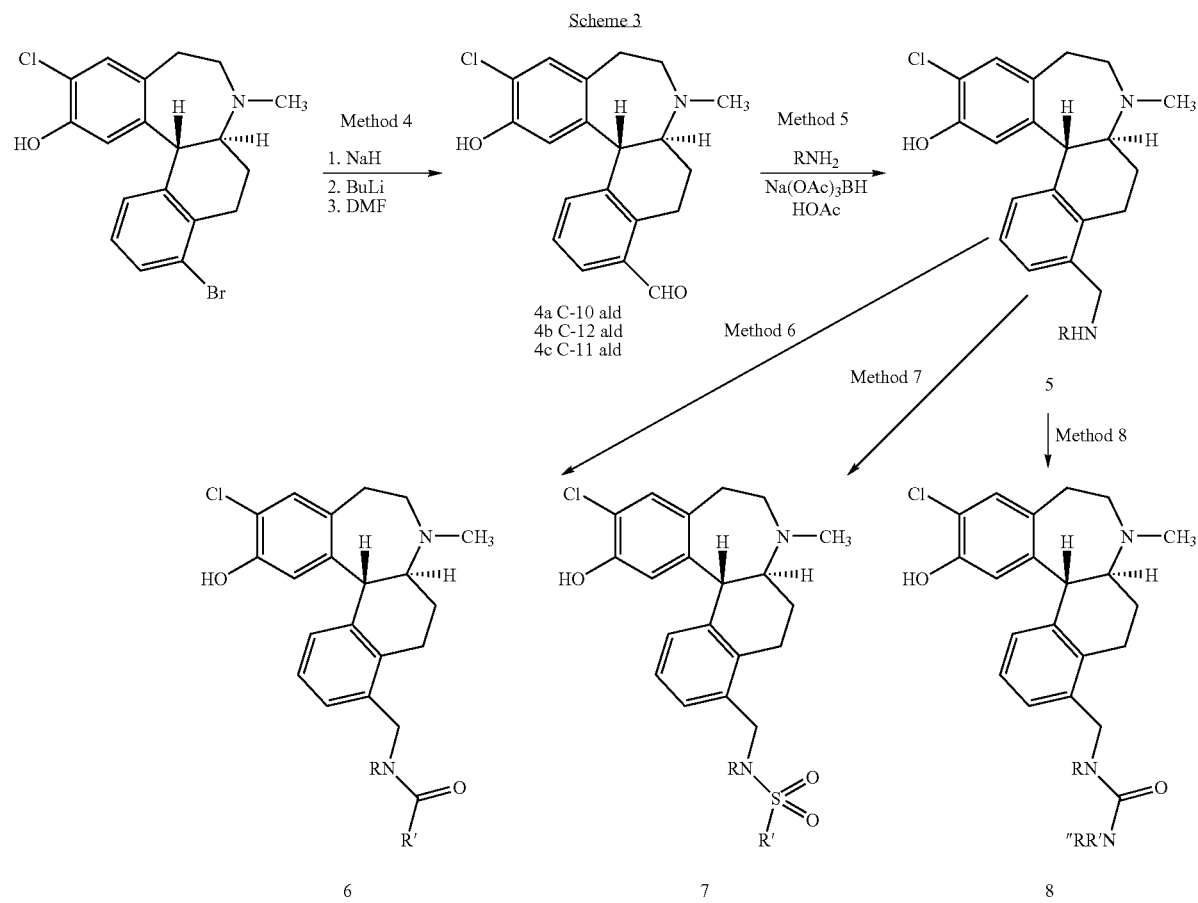
Scheme 3
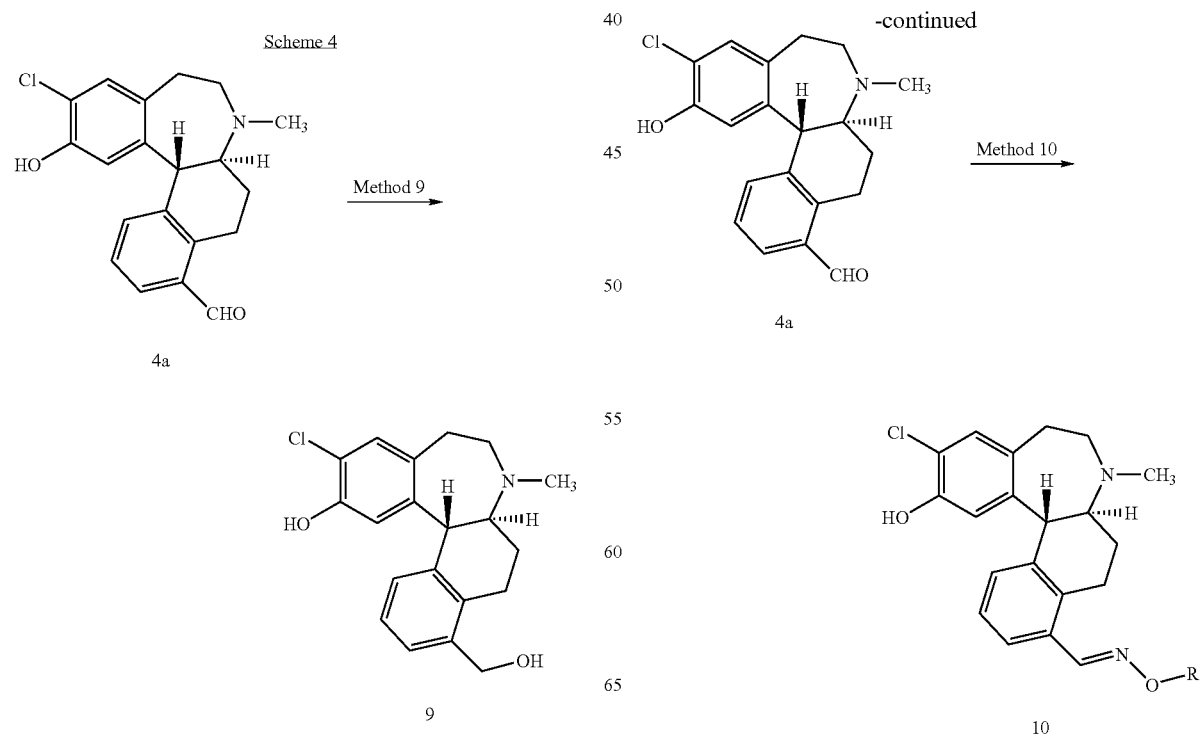
Scheme 4

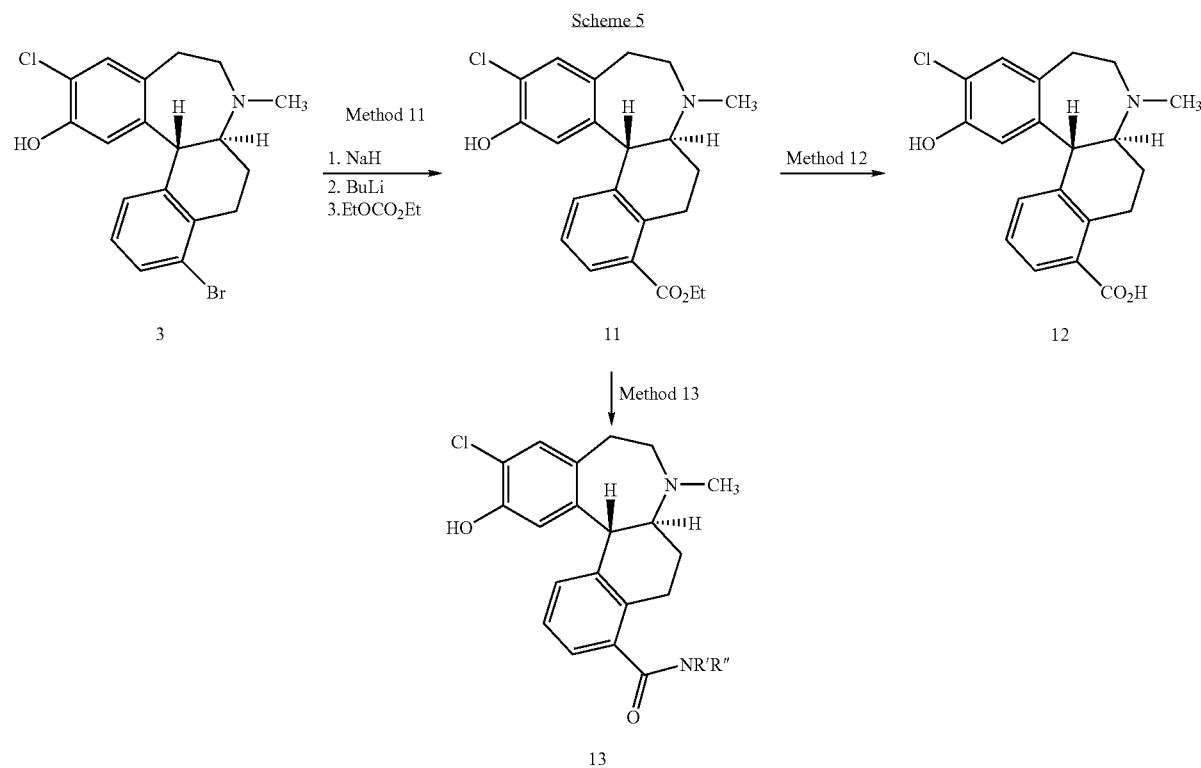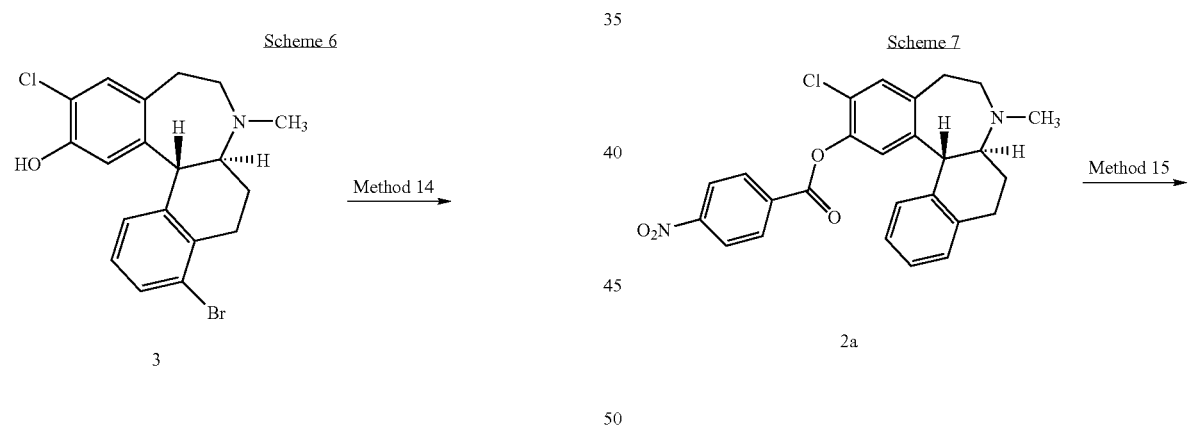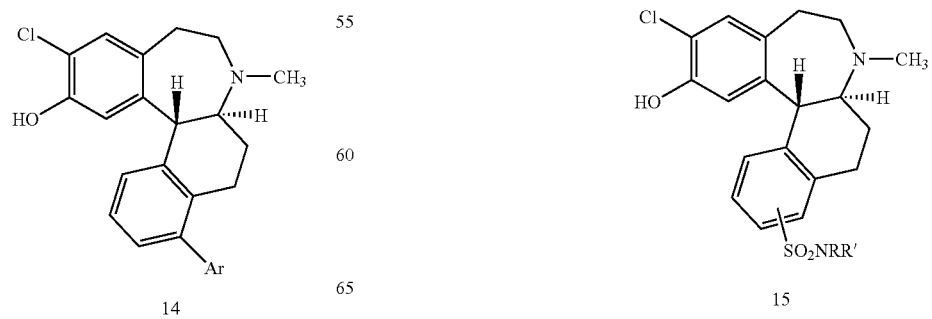

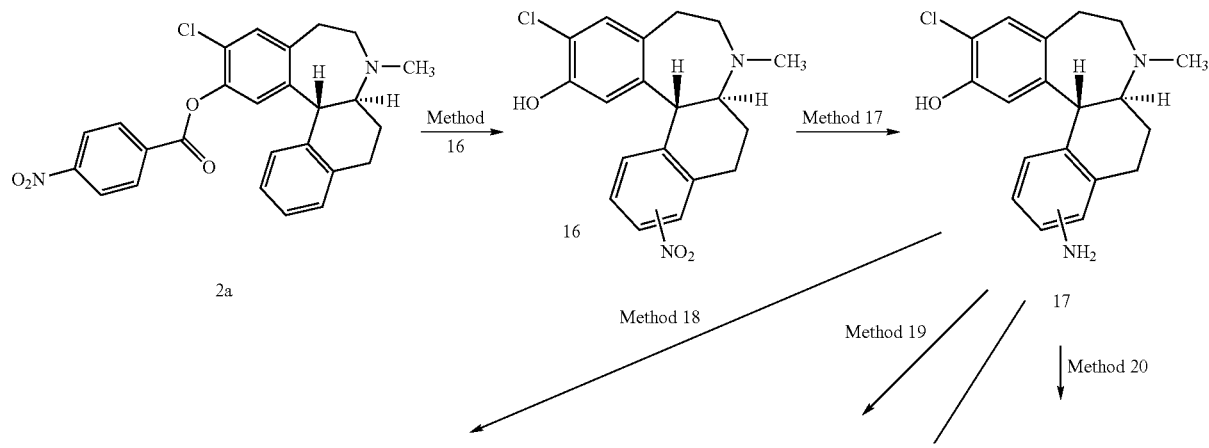
Scheme 8
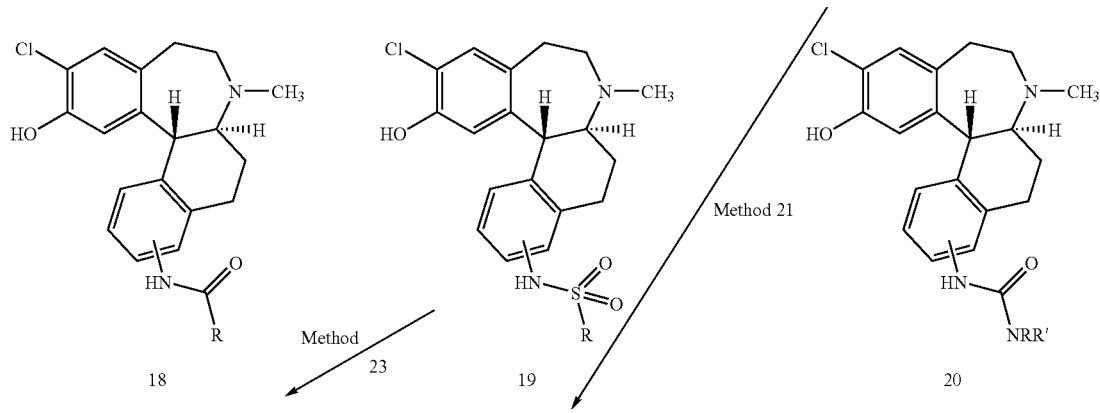
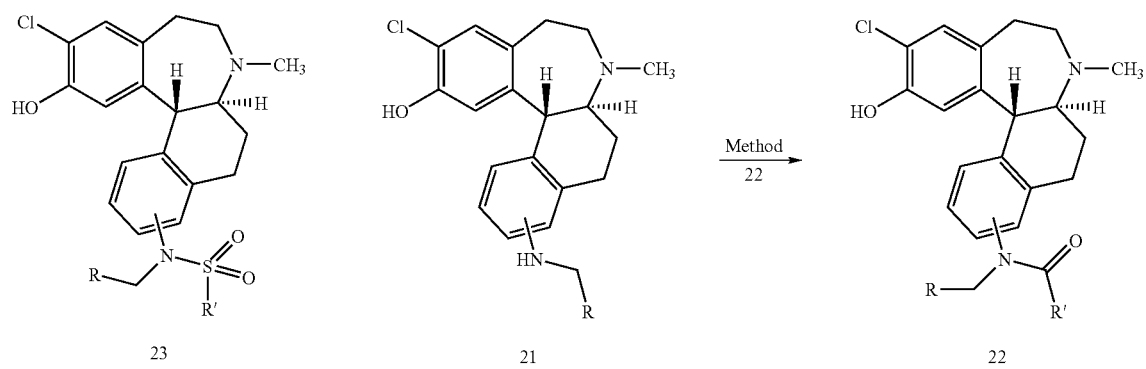

Scheme 9
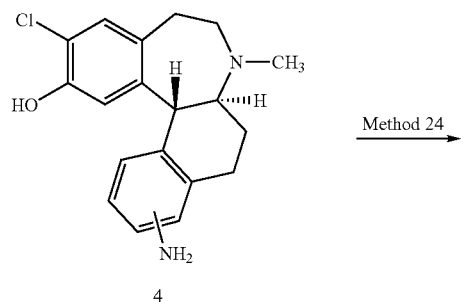
4
→ Method 24
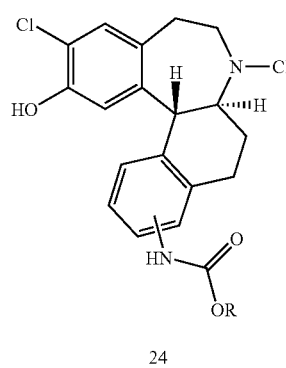
24
Scheme 10
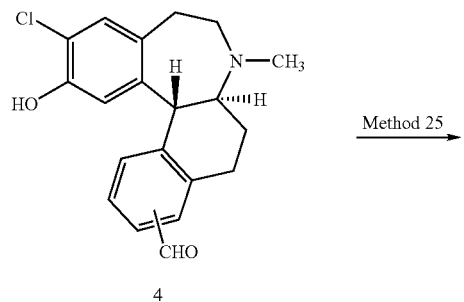
4
→ Method 25
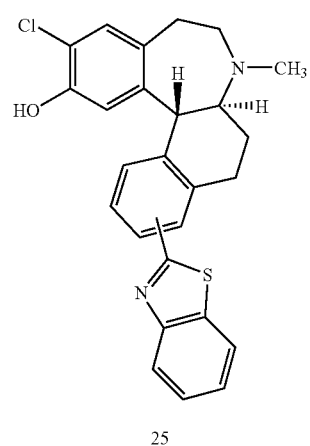
25
Scheme 11
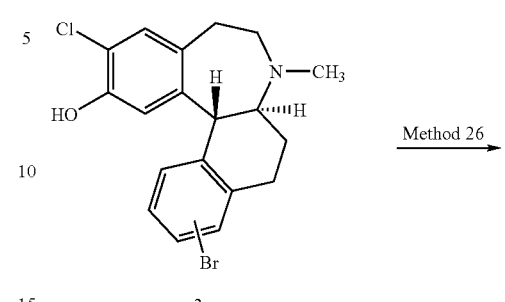
3
→ Method 26
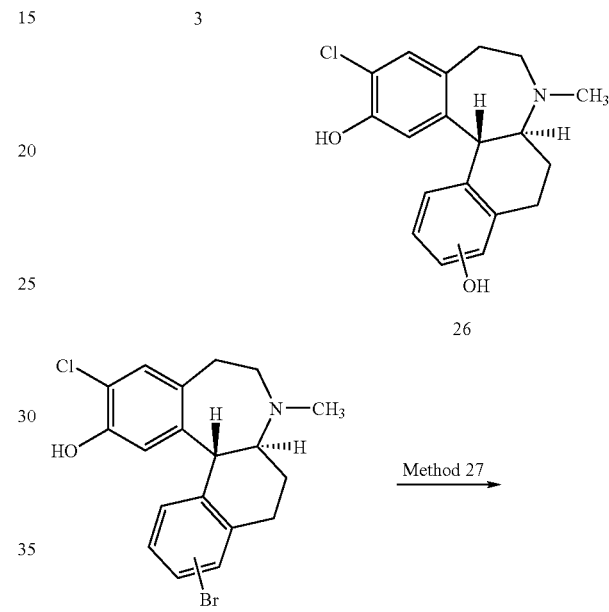
26
3
→ Method 27
27
Scheme 12
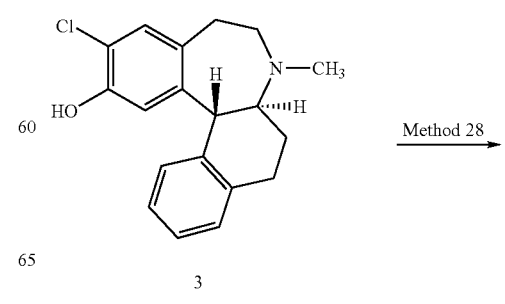
3
→ Method 28

-continued
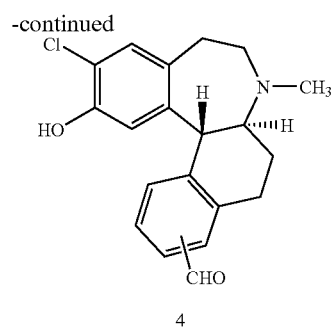
4
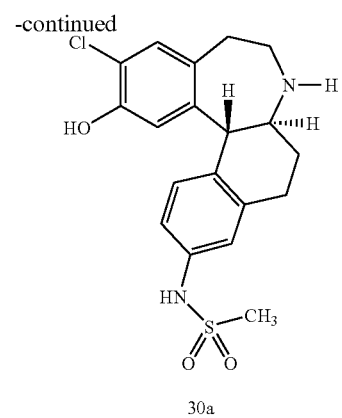
30a
Scheme 13
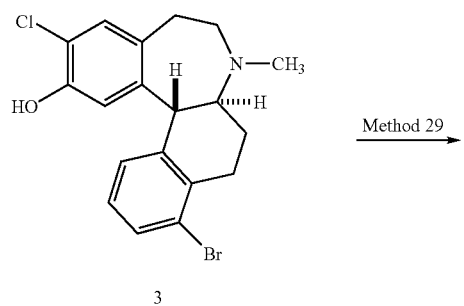
3
Method 29 →
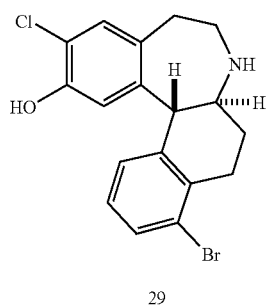
29
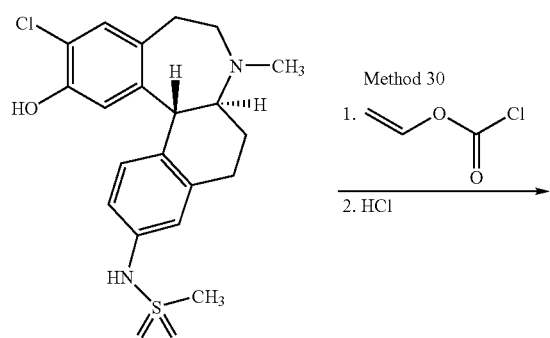
19b1
Method 30
1. <span>vinyl chloroformate</span>
2. HCl
→
Scheme 14
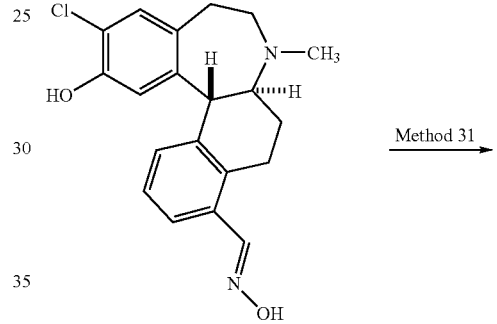
31a
Method 31 →
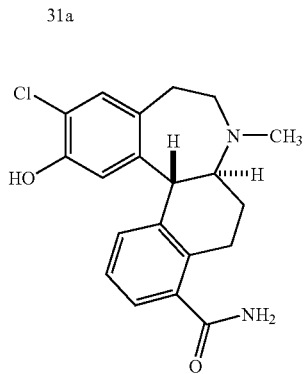
+
31c
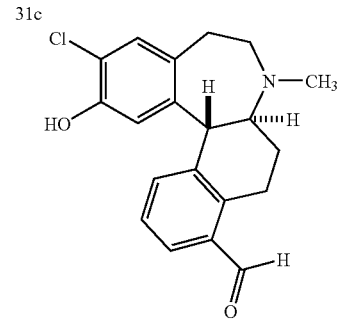
4

35

Scheme 15

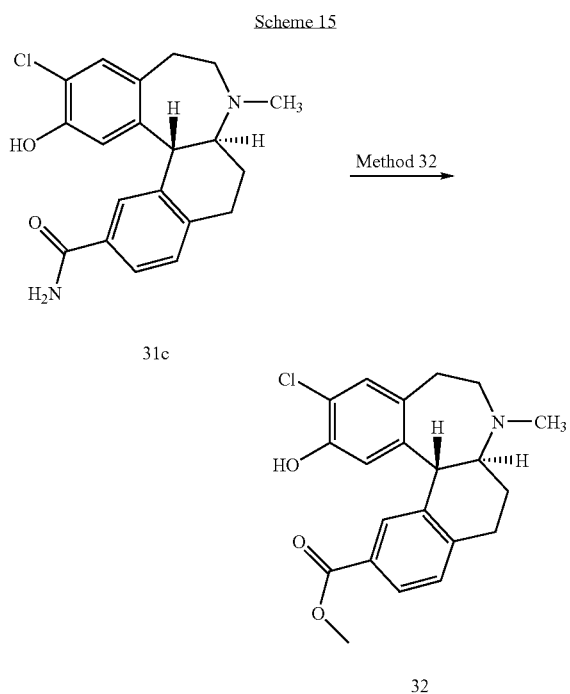

Method 1
Step 1: Process for the Compound of Formula:

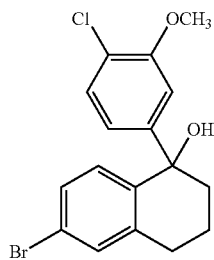

Cerium trichloride (6.14 g, 0.025 moles) was stirred rapidly under vacuum and heated in an oil bath at 145-150° C. for 4 hr. Stirring was continued at 120-150° C. overnight under vacuum. The material was then stirred at r.t. An atmosphere of argon was introduced, followed by the addition of 35 mL of anhydrous THF. The suspension was stirred at room temperature for 1.5 h and was cooled to 0° C. The solution of the Grignard reagent prepared from 5-bromo-2-chloroanisole (5.25 g 0.024 moles) and magnesium turnings (0.58 g, 0.024 moles) in THF (32 mL) was added dropwise to the stirring cerium trichloride suspension at 0° C. The reaction was stirred at 0° C. for 30 min. and then overnight at room temperature. The reaction was shown to be complete by tlc analysis (5% ethyl acetate/hexane). Cooling to 0° C. was followed by quenching with the dropwise addition of 50 mL of saturated aqueous ammonium chloride. The mixture was stirred at room temperature and diluted with additional sat. ammonium chloride (30 mL) and water (50 mL). The aqueous phase was extracted twice with ethyl acetate (150 mL). The combined ethyl acetate extracts were washed with brine (50 mL), dried over anhydrous sodium sulfate and concentrated in vacuo to a thick oil (7.01 g). The crude product was purified by column chromatography on silica gel (300 g) using 15% ethyl acetate/hexane as eluting solvent to give an oil (5.60 g). ES MS: m/z calcd for $C_{17}H_{17}BrClO_2^+$=367.0; found m/z=367.9 (M+1)$^+$ Step 2: Process for the Compound of Formula:

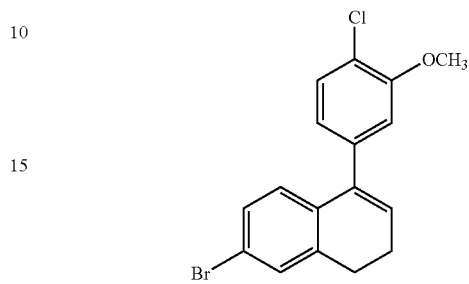

A solution of the above carbinol (5.50 g 0.015 moles) in toluene (150-175 mL) containing p-toluenesulfonic acid (0.010 g) was heated to reflux with the azeotropic removal of water. After 1.5 h, the reaction was cooled to room temperature. A tlc analysis (5% ethyl acetate/hexane) indicated the reaction to be complete. The toluene was evaporated under reduced pressure. The residue was partitioned between ethyl acetate (200 mL) and water (40 mL). The layers were separated and the water was extracted with ethyl acetate (125 mL). The combined ethyl acetate layers were extracted with saturated aqueous sodium bicarbonate and brine (60 mL), then dried over anhydrous sodium sulfate. The solvent was evaporated to an oil (5.28 g). Purification by column chromatography on silica gel (250 g) using 3% ethyl acetate/hexane yielded an oil (4.74 g). ES MS: m/z calcd for $C_{17}H_{15}BrClO^+$= 349.0; found m/z=349.1 (M+1)$^+$ Step 3: Process for the Compound of Formula:

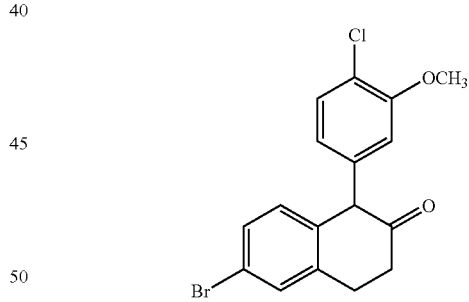

A solution of the above dihydronaphthylene (4.60 g, 0.013 moles) in acetone (45 mL) was stirred with sodium bicarbonate (4.44 g, 0.053 moles) while cooling to 0° C. A solution of Oxone (14.63 g, 0.024 moles) in water (55 mL) was added dropwise over a period 1 h. After the addition was complete, the mixture was stirred at 0° C. for 20 min. It was then warmed to room temperature. The reaction was complete after 1 hr. (tlc analysis, 5% ethyl acetate/hexane). The reaction was diluted with water (75 mL) and dichloromethane (200 mL). The layers were partitioned and separated. The water was extracted with dichloromethane (400 mL). The combined organic extracts were washed with brine (100 mL), dried over anhydrous sodium sulfate, and evaporated to a foamy solid 4.91 g. A solution of this material in toluene (150 mls) containing ptoluenesulfonic acid (0.010 g) was heated to reflux with the azeotropic removal of water. After 2 hrs., the solution was cooled to room temperature. The toluene was evaporated under vacuum. The residue was partitioned between dichloromethane (200 mL) and saturated aqueous sodium bicarbonate (75 mL). Following the separation of the layers, the aqueous phase was extracted with dichloromethane (300 mL). The combined organic extracts were washed with brine (100 mL), dried over anhydrous sodium sulfate, and evaporated under vacuum to a foamy residue 4 67 g. ). ES MS: m/z calcd for $C_{17}H_{15}BrClO_2{}^+$=365.0; found m/z=365.1 (M+1)$^+$ Step 4: Process for the Compound of Formula:

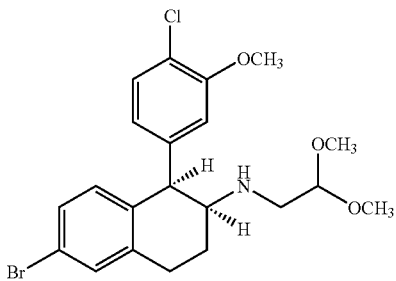

A solution of the tetralone above (4.59 g, 0.013 moles) and amino acetaldehyde dimethyl acetal (1.99 g, 0.019 moles) in toluene (100 mL) was heated to reflux with the removal of water using a Dean-Stark trap. After 5 h, the solution was cooled to 0° C. The t-butyl amine-borane complex (3.29 g, 0.038 moles) was added in portions. Glacial acetic acid (3.60 mL, 0.063 moles) was added dropwise. The solution was then stirred at room temperature overnight. It was cooled in an ice bath, followed by the dropwise addition of water (10 mL) and saturated aqueous sodium bicarbonate (20 mL). The mixture was then stirred at room temperature and saturated sodium bicarbonate was added. The pH was adjusted to 9-10 with 1N sodium hydroxide. Partitioning with ethyl acetate (100 mL) and layer separation. The aqueous phase was extracted with ethyl acetate (300 mL). The combined ethyl acetate extracts were washed with brine (75 mL), dried over anhydrous sodium sulfate, and concentrated under vacuum to a semisolid 8.89 g. This material was purified by column chromatography on silica gel (300 g). Elution with a solvent gradient 35% ethyl acetate/hexane progressing to 50% ethyl acetate/hexane. An oil (2.76 g) was obtained. ). ES MS: m/z calcd for $C_{21}H_{26}BrClNO_3{}^+$=456.1; found m/z=456.1 (M+1)$^+$ Step 5: Process for the Compound of Formula:

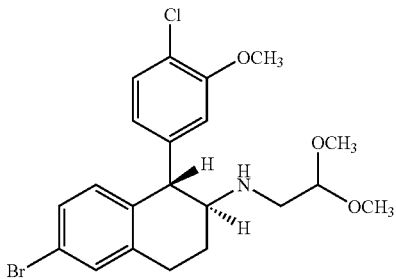

A stirring solution of the above cis amine (2.15 g, 4.73 mmol) in anhydrous DMSO (15 mL) at room temperature was treated with the addition of KOBu-t (0.150 g, 1.34 mmol) in portions. After 1h, the reaction was complete by tlc. The DMSO solution was added in portions to stirring ice/saturated aqueous sodium bicarbonate (200 mL). The aqueous phase was extracted with ether (200 mL). The layers were separated and the water was extracted with ether (250 mL). The combined ether extracts were washed with brine (100 mL), dried over anhydrous sodium sulfate, and evaporated under vacuum to a thick oil 2.03 g. This material was purified by column chromatography on silica gel (200 g) using a solvent gradient 40% ethyl acetate/hexane to 80% ethyl acetate/hexane. An oil was obtained 1.00 g. ES MS: m/z calcd for $C_{21}H_{26}BrClNO_3{}^+$=456.1; found m/z=456.2 (M+1)$^+$ Step 6: Process for the Compound of Formula:

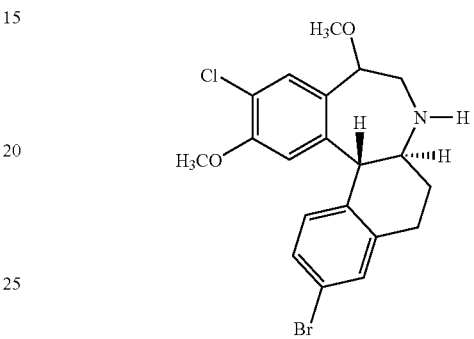

A solution of the trans amine from the previous step (0.95 g, 2.09 mmol) in 5 mL of dichloromethane cooled to 0° C. was treated with the dropwise addition of methane sulfonic acid (2.0 mL, 31.4 mmol). After the addition was complete, stirring at 0° C. was continued for 15 min. and then maintained at room temperature for 2 hrs. The dichloromethane solution was added dropwise to stirring ice/water (100 mL). The aqueous mixture was made strongly basic with 3N sodium hydroxide and was extracted with dichloromethane (100 mL). The layers were separated and the water was extracted with dichloromethane (100 mL). The combined organic extracts were washed with brine (50 mL), dried over anhydrous sodium sulfate, and evaporated to a foamy solid 0.869 g. ES MS: m/z calcd for $C_{20}H_{22}BrClNO_2{}^+$=424.1; found m/z=424.1 (M+1)$^+$ Step 7: Process for the Compound of Formula:

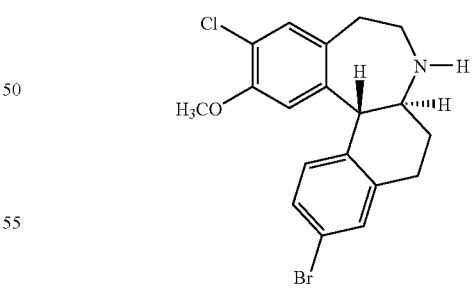

The benzazepine from step 6 above (0.40 g, 0.94 mmol) was dissolved in dichloroethane (5 mL) and cooled in an ice bath. Methane sulfonic acid (0.92 mL, 14.1 mmol) was added dropwise. After the addition was complete, stirring at 0° C. was, continued for 15 min. The reaction was then maintained at room temperature for 2 h. The reaction was then heated in an oil bath at 60 to 65° C. for 4 h. It was cooled to room temperature and the tert-butyl amine borane complex (0.41 g, 4 71 mmol) was added in portions. It was stirred at room temperature for 4 hrs. The dichloromethane solution was added to stirring ice/water (30 mL) and was made strongly basic with the addition of 3N sodium hydroxide. The mixture was extracted with dichloromethane (50 mL). The layers were separated and the water was washed with dichloromethane (100 mLs). The combined organic extracts were washed with brine (50 mL), dried over anhydrous sodium sulfate, and concentrated to a solid 0.359 g. ES MS: m/z calcd for $C_{19}H_{20}BrClNO^+$=392.0; found m/z=394.1 (M+1)$^+$ Step 8: Process for the Compound of Formula: 1a

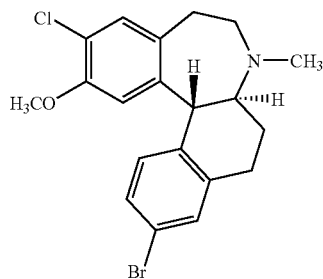

To a stirring solution of the N-unsubstituted benzazepine from step 7 (0.33 g, 0.84 mmol) in DMF (2.5 mL) at room temperature was added formic acid (1.60 mL, 41.8 mmol) dropwise and 37% formaldehyde in water (4.20 mL). The reaction was heated in an oil bath at 60 to 65° C. for 3h and then at room temperature for 1.5 h. Dichloromethane (50 mL) and water (20 mL) were added followed by subsequent stirring. The aqueous phase was made strongly basic with 3N sodium hydroxide. The partitioned layers were separated and the water was extracted with dichloromethane (80 mL). The combined organic extracts were washed with brine (50 mL), dried over anhydrous sodium sulfate, and evaporated to a solid 0.323 g. The product was purified by column chromatography on silica gel (30 g) eluting with a solvent gradient of 80% ethyl acetate/hexane to 95% ethyl acetate/hexane. The product was obtained as a solid 0.233 g. ES MS: m/z calcd for $C_{20}H_{22}BrClNO^+$=408.1; found m/z=408.1 (M+1)$^+$ Step 9: Process for the Compound of Formula: Ia

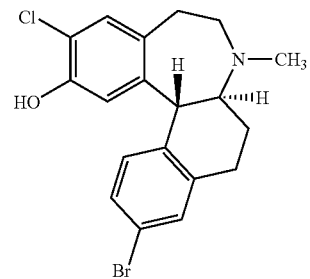

A solution of the above N-Me product from step 8 (0.030 g, 0.074 mmol) in dichloromethane (0.5 mL) was cooled to −78° C. and 1M boron tribromide in dichloromethane (0.33 mL, 0.33 mmol) was added dropwise. The reaction was stirred at −78° C. for 15 min and then maintained at room temperature for 2.5 h. Methanol (0.50 mL) was added dropwise while cooling the reaction in an ice bath. The reaction was stirred at room temperature for 45 min. and heated at reflux for 30 min. The reaction was cooled followed by stirring with water (5 mL). The reaction was made basic with saturated aqueous sodium bicarbonate. The aqueous phase was extracted with ethyl acetate (40 mL). The layers were separated and the water was extracted with ethyl acetate (40 mL). The combined organic extracts were washed with brine (30 mL), dried over anhydrous sodium sulfate, and evaporated to give 0.031 g of the phenolic benzazepine 1a as a solid. ES MS: m/z calcd for $C_{19}H_{20}BrClNO^+$=394.0; found m/z=394.1 (M+1)$^+$ Method 2:

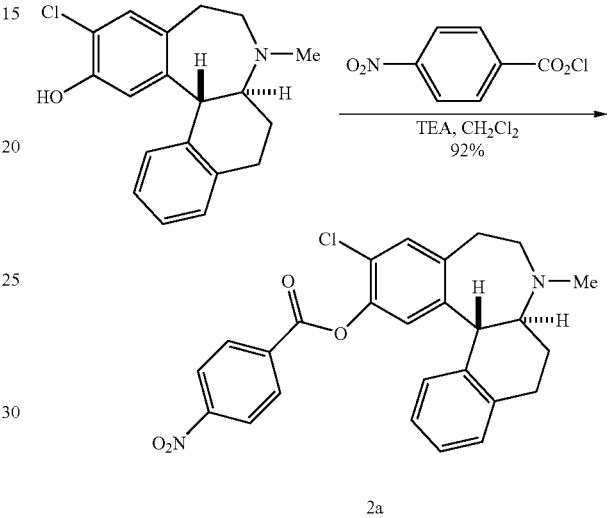

2a

To a suspension of 5.0 g of ecopipam (15.9 mmol) in 100 mL of dichloromethane was added 10 mL of triethylamine at room temperature under nitrogen. 4-Nitrobenzoyl chloride (3.0 g, 16.2 mmol) was added slowly and stirred at room temperature for 1 h. The reaction mixture was poured into aqueous NaHCO$_3$/dichloromethane mixture and extracted with 2-100 mL portions of dichloromethane. The organic extract was washed twice with saturated sodium bicarbonate solution and brine. The organic layer was dried over sodium sulfate and concentrated in vacuo to give 6.8 g of 2a as a solid. ES MS: m/z calcd for $C_{26}H_{24}ClN_2O_4^+$=463.14; found m/z=462.92 (M+1)$^+$.

Compound 2b can also be made by an analogous procedure starting with a compound of formula II.

Formula II

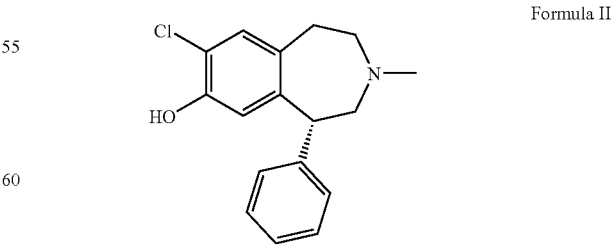

:$^1$HNMR (CDCl$_3$) δ 2.38 (m, 1H) 2.40 (s, 3H) 2.80-3.00 (m, 3H) 3.10-3.22 (m, 2H) 4.38 (d, 1H, J=8.6Hz) 6.50 (s, 1H) 7.20 (d, 2H, J=7.6Hz) 7.30 (m, 2 H) 7.39 (m, 2H) 8.18 (s, 4H).

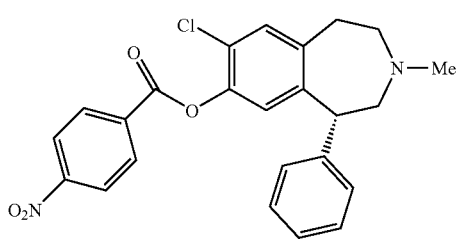

2b

Method 3:

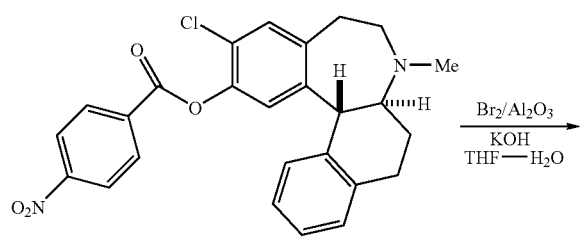

2a

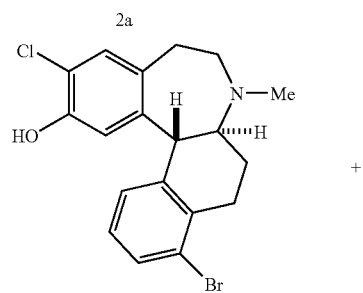

3a

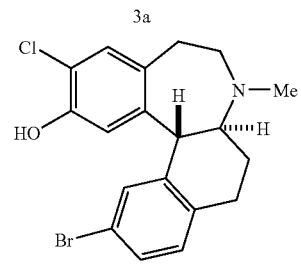

3b

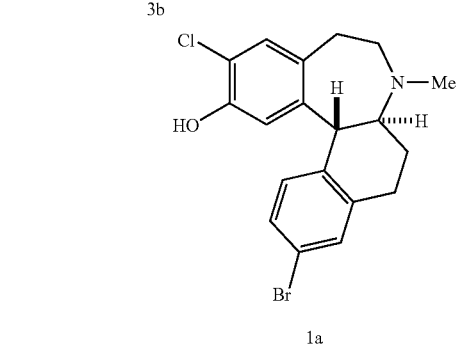

1a 5 g of p-nitrobenzoate, 2a, (10.8 mmol) was mixed with 10 g of neutral alumina (chromatography grade, 50-200 micron). In a separate bottle, bromine (17.27 g, 10 eq.) was mixed with 10 g of alumina. The above mixtures were shaken together for 30 minutes and charged onto a small silica gel column. The excess bromine was eluted with hexane followed by dichloromethane. The column was washed with methanol to elute the bromination products. The solvent was removed in vacuo. The resulting residue was redissolved in 50 mL of THF—H$_2$O (9:1) and treated with 15 mL 1N KOH. The mixture was stirred for 4h, then neutralized with acetic acid. The contents were poured into a saturated NaHCO$_3$/dichloromethane mixture and extracted with 2-100 mL portions of dichloromethane. The organic layer was washed with sodium bicarbonate solution and brine. The organic layer was dried over sodium sulfate and concentrated in vacuo. The products were purified by silica gel chromatography eluting with 50% acetone/hexane. The products were further purified by repeated crystallization from ethanol. This purification method gave 1.02 g of 3a: ES MS: calcd for C$_{19}$H$_{20}$BrClNO$^+$= 392.04, 394.04; found=394.1 (M+1)$^+$ as the major product.

The following compounds were also isolated by this process:

| Cpd. # | Structure | Analytical data |
|---|---|---|
| 3b | 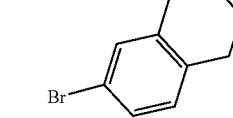 | ES MS: calcd for C$_{19}$H$_{20}$BrClNO$^+$ = 392.04, 394.04; found = 394.1 (M + 1)$^+$ |
| 1a | 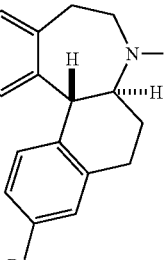 | ES MS: calcd for C$_{19}$H$_{20}$BrClNO$^+$ = 392.04, 394.04; found = 394.1 (M + 1)$^+$ |

Alternatively, the aryl ring can be brominated as follows:

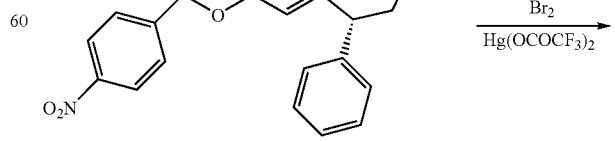

2b

-continued

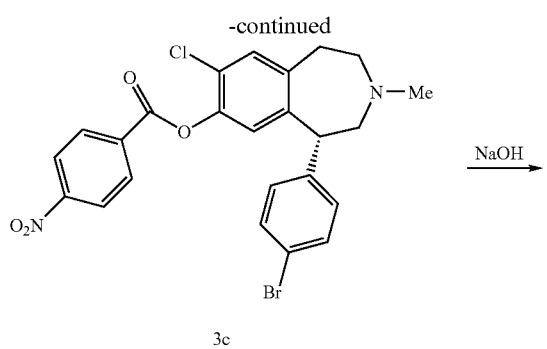

3c

Using analogous chemistry the following compound can also be prepared

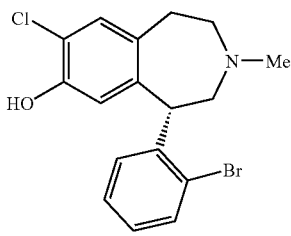

3g

3g ¹H NMR (CDCl₃) δ 2.20 (m, 1H) 2.40 (s, 3H) 2.60-2.80 (m, 2H) 3.10 (m, 2H) 3.20-3.38 (m, 2H) 4.80 (d, 1H, J=8.8 Hz) 5.40 (br s, 1H) 6.05 (s, 1H) 7.10(s,1H) 7.10-7.38 (m, 4H) 7.60 (dd, 2H, J=1.2, 8.0Hz).

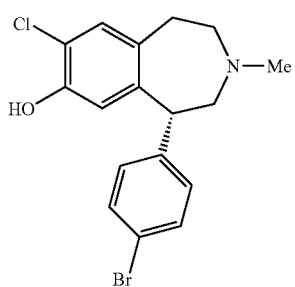

3f

Method 4

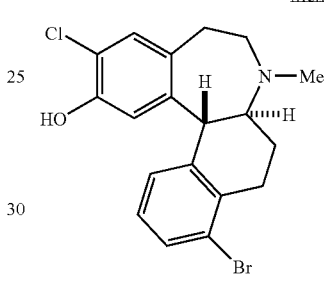

3a

1. NaH/THF
2. BuLi/THF
3. DMF

Step 1:

Compound 2b (0.99 g, 2.27 mmol) was dissolved in 10 mL trifluoroacetic acid followed by the addition of 0.97 g of Hg(OCOCF₃)₂. The mixture was cooled to −20° C. followed by dropwise addition of Br₂ (0.4 g, 1.1 eq). The mixture was stirred for 30 min and the solvent was removed in vacuo. The residue was partitioned between EtOAc and saturated aqueous NaHCO₃. Concentration of the organic extracts gave a mixture of three products by NMR: p-Br analog 3c, o-Br analog 3d, (1:1) and a small amount of the o,p-dibromo analog, 3e. Repeated SiO₂ chromatography eluting with EtOAc: hexanes:triethylamine (50:50:1) gave 3c in 25% yield: ¹H NMR (CDCl₃) δ 2.38 (m, 1H) 2.40 (s, 3H) 2.80-3.00 (m, 3H) 3.01-3.18 (m, 2H) 4.30 (d, 1H, J=8.3 Hz) 6.50 (s, 1H) 7.05 (d, 2H, J=8.3 Hz) 7.22 (s, 1H) 7.50 (d, 2H, J=8.3 Hz) 8.18 (s, 4H).

Step 2:

Compound 3c (1.7 g, 3.29 mmol, 1 eq) was treated with NaOH (0.39 g) in 10 mL of water and 25 mL of THF under N₂. After 3 h, the pH was adjusted to 10 and extraction with dichloromethane afforded 1.2 g of phenol 3f as a white solid. ¹HNMR (CDCl₃) δ 2.38 (m, 1H) 2.40 (s, 3H) 2.70-3.10 (m, 5H) 4.20 (br, 1H, J=8.3 Hz) 5.70 (br s, 1H) 6.30 (s, 1H) 7.00 (d, 2H, J=8.3 Hz) 7.08 (s, 1H) 7.48 (d, 2H, J=8.3 Hz).

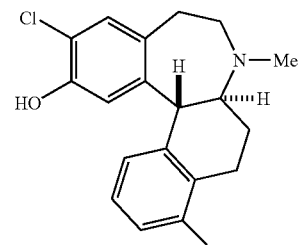

4a

Compound 3a (2.7 g, 6.87 mmol) was dissolved in 200 mL of THF and cooled to −78° C. under nitrogen. Sodium hydride (90%, 0.25 g, 1.5 eq) was added and the mixture was stirred at −78° C. for 30 minutes. n-BuLi (2.5 M solution in hexanes, 6 mL, 2.2 eq) was added dropwise and the mixture stirred at −78° C. for 30 minutes. DMF (10 mL) was added to the above reaction mixture and the reaction stirred at −78° C. for 1 h. The reaction was quenched by the addition of saturated NH₄Cl and extracted with dichloromethane. The organic layer was washed with brine and dried over sodium sulfate. The solvent was evaporated in vacuo and the product was isolated by silica gel column chromatography eluting with 3% MeOH/dichloromethane mixture to give 1.93 g of 4a as a solid. ES MS: calcd for $C_{20}H_{21}ClNO_2^+$=342.1; found=342.1 $(M+1)^+$ The following compounds can be prepared by an analogous procedure starting with regioisomeric aryl bromides:

| Cpd. # | Structure | Analytical data |
|---|---|---|
| 4b | (structure) | ES MS: calcd for $C_{20}H_{21}ClNO_2^+$ = 342.1; found = 342.1 $(M + 1)^+$ |
| 4c | (structure) | |

The following compound can be prepared analogously from 3C:

| Cpd. # | Structure | Analytical data |
|---|---|---|
| 4d | (structure) | ES MS: calcd for $C_{18}H_{18}ClNO_2^+$ = 315; found = $(M + 1)^+$ |

Method 5

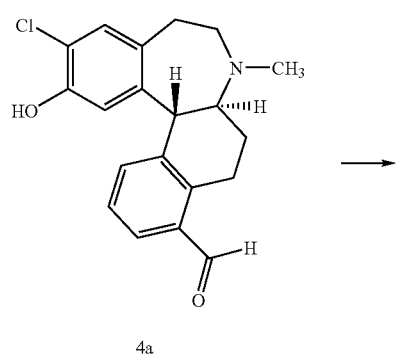

4a

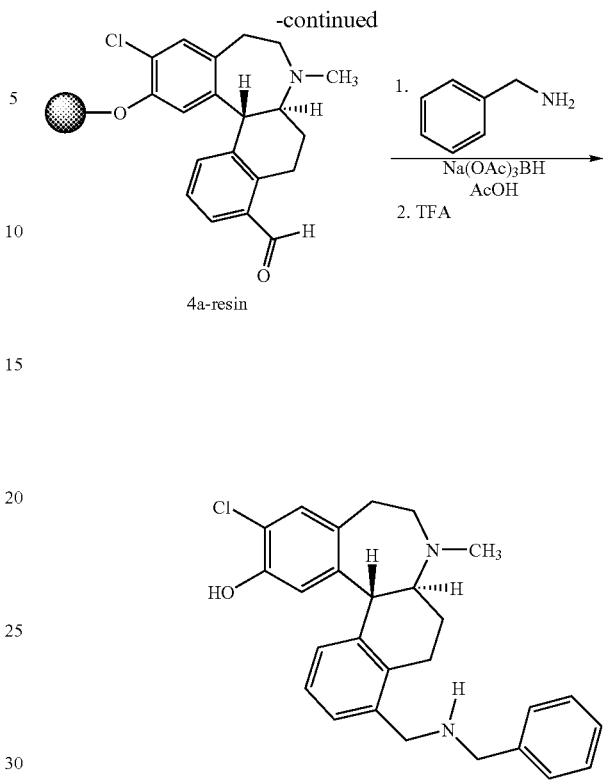

To a preconditioned mixture of 3.70 g of 2-chlorotrityl chloride resin (0.8 mmol/g) in dichloromethane (26 mL) was added 0.985 g (2.88 mmol) of aldehyde 4a, followed by 3.2 mL (18.4 mmol) of iPr$_2$Net. The resulting mixture was agitated for 16 hours at ambient temperature. The reaction was quenched with 15 mL of a 10% iPr$_2$NEt/methanol solution and agitated for an additional 10 minutes. The liquid was drained, and the resin was washed three times each with dichloromethane, THF, and methanol. The beads were dried under reduced pressure to provide 4.40 g of resin-bound aldehyde 4a-resin.

To a 104 mg (0.62 mmol/g) of a preconditioned mixture of resin-bound 4a in 3.0 mL of dichloroethane was added 0.24 mL (2.2 mmol) of benzyl amine followed by 0.032 mL of acetic acid (0.56 mmol). The resulting mixture was agitated for 18 hours at ambient temperature. At this time, 460 mg (2.2 mmol) of Na(OAc)$_3$BH was added and the agitation continued for 68 hours at room temperature. The supernatant liquid was drained, and the resin was washed with methanol (3×), THF (3×), and dichloromethane (3×). The yellow beads were subjected to 3% TFA in dichloromethane (2 mL) and agitation for 25 minutes. The liquid was drained, the beads were washed with dichloromethane (3×), and the solvent was removed in vacuo. The residue was purified by preparative TLC eluting with 2M NH$_3$ in methanol/dichloromethane (5:95) to provide 25 mg of product 5a1 as a solid: LCMS: m/z calcd for $C_{27}H_{30}ClN_2O^+(M+1)^+$=433.2; m/z obsvd=433.1.

The following compounds can be prepared analogously:
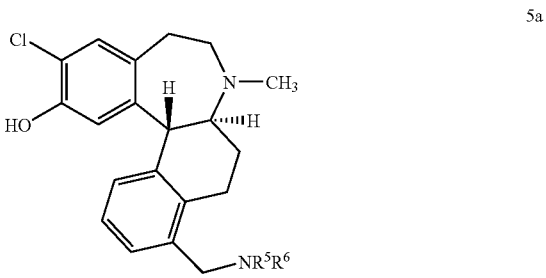
5a
| Cpd. # | NR⁵R⁶ | Molecular Formula | Mol. Wt. | Obs. (M + 1)⁺ |
|---|---|---|---|---|
| 5a2 | (3-pyridyl)NH– | $C_{25}H_{26}ClN_3O$ | 419.96 | 420.1 |
| 5a3 | (4-methoxyphenyl)NH– | $C_{27}H_{29}ClN_2O_2$ | 449.00 | 449.1 |
| 5a4 | (2-chlorobenzyl)NH– | $C_{27}H_{28}Cl_2N_2O$ | 467.44 | 467.1 |
| 5a5 | (2-pyridylmethyl)NH– | $C_{26}H_{28}ClN_3O$ | 433.99 | 434.1 |
| 5a6 | 1,2,3,4-tetrahydroisoquinolin-2-yl | $C_{29}H_{31}ClN_2O$ | 459.04 | 459.1 |

-continued
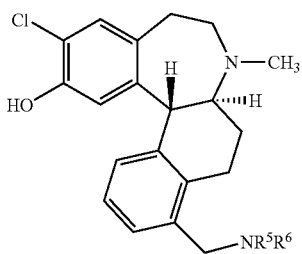
5a
| Cpd. # | NR⁵R⁶ | Molecular Formula | Mol. Wt. | Obs. (M + 1)⁺ |
|---|---|---|---|---|
| 5a7 | 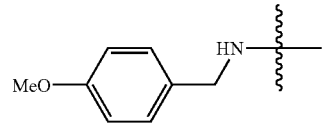 | $C_{28}H_{31}ClN_2O_2$ | 463.02 | 463.1 |
| 5a8 | 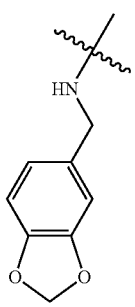 | $C_{28}H_{29}ClN_2O_3$ | 477.01 | 477.1 |
| 5a9 | 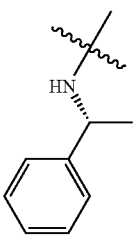 | $C_{28}H_{31}ClN_2O$ | 447.03 | 447.1 |
| 5a10 | 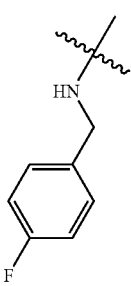 | $C_{27}H_{28}ClFN_2O$ | 450.99 | 451.1 |
| 5a11 | 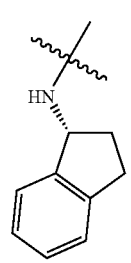 | $C_{29}H_{31}ClN_2O$ | 459.04 | 459.1 |

-continued
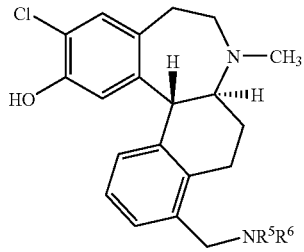
5a
| Cpd. # | NR⁵R⁶ | Molecular Formula | Mol. Wt. | Obs. (M + 1)⁺ |
|---|---|---|---|---|
| 5a12 | (4-pyridylmethyl-amino) | $C_{26}H_{28}ClN_3O$ | 433.99 | 434.1 |
| 5a13 | (2-methylbenzyl-amino) | $C_{28}H_{31}ClN_2O$ | 447.03 | 447.1 |
| 5a14 | (diphenylmethyl-amino) | $C_{33}H_{33}ClN_2O$ | 509.10 | 509.1 |
| 5a15 | (3-trifluoromethyl-benzylamino) | $C_{28}H_{28}ClF_3N_2O$ | 501.00 | 501.1 |
| 5a16 | (3,4-dichlorobenzyl-amino) | $C_{27}H_{27}Cl_3N_2O$ | 501.89 | 503.1 |

-continued
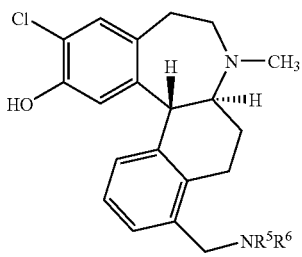
5a
| Cpd. # | NR⁵R⁶ | Molecular Formula | Mol. Wt. | Obs. (M + 1)⁺ |
|---|---|---|---|---|
| 5a17 | 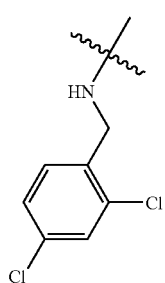 | $C_{27}H_{27}Cl_3N_2O$ | 501.89 | 503.1 |
| 5a18 | 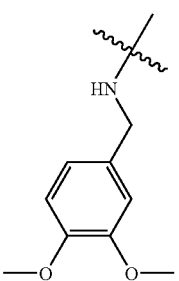 | $C_{29}H_{33}ClN_2O_3$ | 493.05 | 493.1 |
| 5a19 | 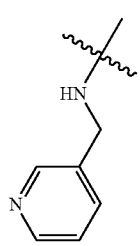 | $C_{26}H_{28}ClN_3O$ | 433.99 | 434.1 |
| 5a20 | 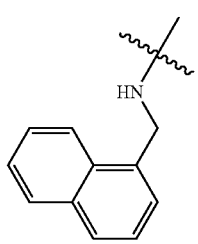 | $C_{31}H_{31}ClN_2O$ | 483.06 | 483.1 |

-continued
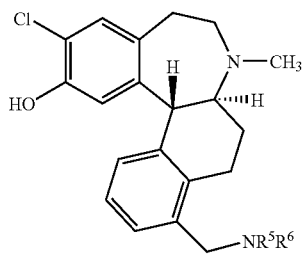
5a
| Cpd. # | NR⁵R⁶ | Molecular Formula | Mol. Wt. | Obs. (M + 1)⁺ |
|---|---|---|---|---|
| 5a21 | 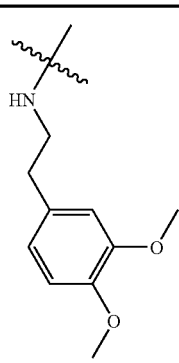 | $C_{30}H_{35}ClN_2O_3$ | 507.08 | 507.1 |
| 5a22 | 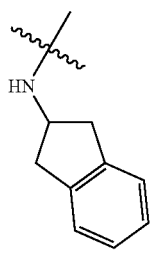 | $C_{29}H_{31}ClN_2O$ | 459.04 | 459.1 |
| 5a23 | 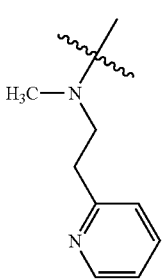 | $C_{28}H_{32}ClN_3O$ | 462.04 | 462.1 |
| 5a24 | 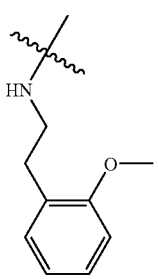 | $C_{29}H_{33}ClN_2O_2$ | 477.05 | 477.1 |

-continued
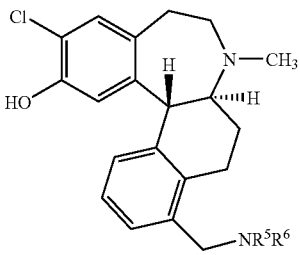
5a
| Cpd. # | NR$^5$R$^6$ | Molecular Formula | Mol. Wt. | Obs. (M + 1)$^+$ |
|---|---|---|---|---|
| 5a25 | 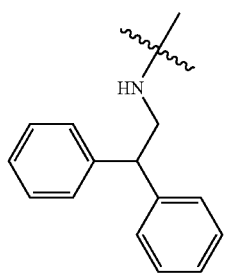 | C$_{34}$H$_{35}$ClN$_2$O | 523.12 | 523.1 |
| 5a26 | 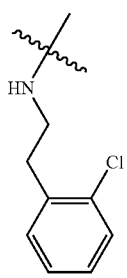 | C$_{28}$H$_{30}$Cl$_2$N$_2$O | 481.47 | 481.1 |
| 5a27 | 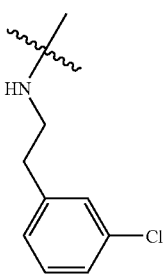 | C$_{28}$H$_{30}$Cl$_2$N$_2$O | 481.47 | 481.1 |
| 5a28 | 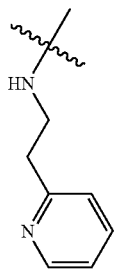 | C$_{27}$H$_{30}$ClN$_3$O | 448.01 | 448.1 |

-continued
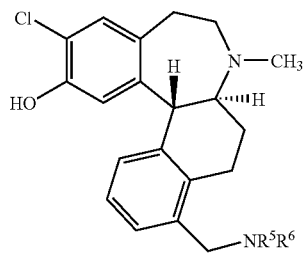
5a
| Cpd. # | NR⁵R⁶ | Molecular Formula | Mol. Wt. | Obs. (M + 1)⁺ |
|---|---|---|---|---|
| 5a29 | 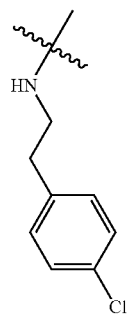 | $C_{28}H_{30}Cl_2N_2O$ | 481.47 | 481.1 |
| 5a30 | 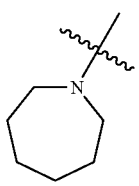 | $C_{26}H_{33}ClN_2O$ | 425.02 | 425.1 |
| 5a31 | 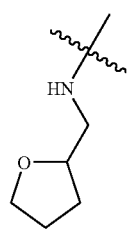 | $C_{25}H_{31}ClN_2O_2$ | 426.99 | 427.1 |
| 5a32 | 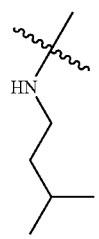 | $C_{25}H_{33}ClN_2O$ | 413.01 | 413.1 |

-continued
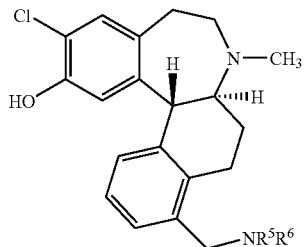
5a
| Cpd. # | NR⁵R⁶ | Molecular Formula | Mol. Wt. | Obs. (M + 1)⁺ |
|---|---|---|---|---|
| 5a33 | | $C_{29}H_{33}ClN_2O$ | 461.05 | 461.1 |
| 5a34 | | $C_{35}H_{37}ClN2O$ | 537.15 | 537.1 |
| 5a35 | | $C_{25}H_{31}ClN_2O$ | 410.99 | 411.1 |
| 5a36 | | $C_{31}H_{35}ClN_2O$ | 487.09 | 487.1 |
| 5a37 | | $C_{24}H_{29}ClN_2O$ | 396.97 | 397.1 |

-continued
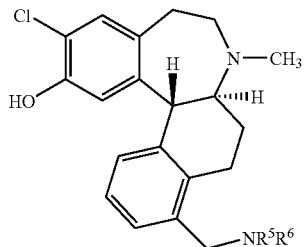
5a
| Cpd. # | NR⁵R⁶ | Molecular Formula | Mol. Wt. | Obs. (M + 1)⁺ |
|---|---|---|---|---|
| 5a38 | (cyclopropylamino) | $C_{23}H_{27}ClN_2O$ | 382.94 | 383.1 |
| 5a39 | (1-ethoxycarbonyl-piperidin-4-ylamino) | $C_{28}H_{36}ClN_3O_3$ | 498.07 | 498.1 |
| 5a40 | (4-(2-methoxyphenyl)piperazin-1-yl) | $C_{31}H_{36}ClN_3O_2$ | 518.10 | 518.1 |
| 5a41 | (4-(pyridin-2-yl)piperazin-1-yl) | $C_{29}H_{33}ClN_4O$ | 489.07 | 489.1 |
| 5a42 | (4-methylpiperazin-1-yl) | $C_{25}H_{32}ClN_3O$ | 426.01 | 426.1 |

-continued
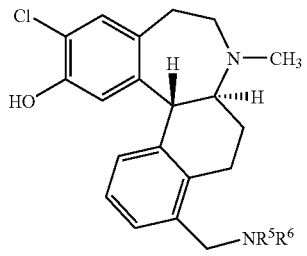
5a
| Cpd. # | NR5R6 | Molecular Formula | Mol. Wt. | Obs. (M + 1)+ |
|---|---|---|---|---|
| 5a43 | 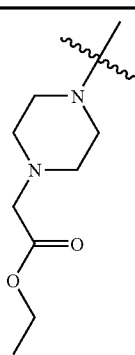 | $C_{28}H_{36}ClN_3O_3$ | 498.07 | 498.1 |
| 5a44 | | $C_{31}H_{36}ClN_3O$ | 502.11 | 502.1 |
| 5a45 | 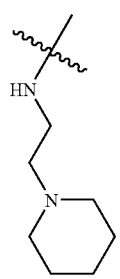 | $C_{27}H_{36}ClN_3O$ | 454.06 | 454.1 |
| 5a46 | 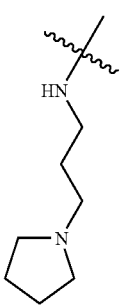 | $C_{27}H_{36}ClN_3O$ | 454.06 | 454.1 |

-continued
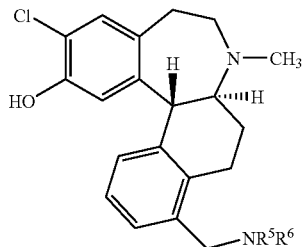
5a
| Cpd. # | NR⁵R⁶ | Molecular Formula | Mol. Wt. | Obs. (M + 1)⁺ |
|---|---|---|---|---|
| 5a47 | (1-ethylpyrrolidin-2-yl)methylamino | $C_{27}H_{36}ClN_3O$ | 454.06 | 454.1 |
| 5a48 | 2-morpholinoethylamino | $C_{26}H_{34}ClN_3O_2$ | 456.03 | 456.1 |
| 5a49 | phenethylamino | $C_{28}H_{31}ClN_2O$ | 447.03 | 447.0 |
| 5a50 | dimethylamino | $C_{22}H_{27}ClN_2O$ | 370.93 | 371.1 |
| 5a51 | propylamino | $C_{23}H_{29}ClN_2O$ | 384.95 | 385.1 |
| 5a52 | cyclobutylamino | $C_{24}H_{29}ClN_2O$ | 396.97 | 397.1 |
| 5a53 | phenylamino | $C_{26}H_{27}ClN_2O$ | 418.97 | 419.1 |

-continued
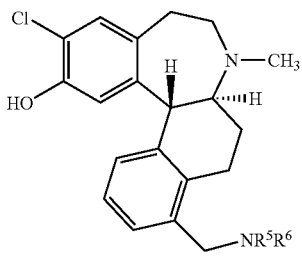
5a
| Cpd. # | NR⁵R⁶ | Molecular Formula | Mol. Wt. | Obs. (M + 1)⁺ |
|---|---|---|---|---|
| 5a54 | 3-F-C₆H₄-NH- | $C_{26}H_{26}ClFN_2O$ | 436.96 | 437.1 |
| 5a55 | 5,6,7,8-tetrahydronaphthalen-1-yl-NH- | $C_{30}H_{33}ClN_2O$ | 473.06 | 473.1 |
| 5a56 | 4-Cl-C₆H₄-NH- | $C_{26}H_{26}Cl_2N_2O$ | 453.42 | 453.1 |
| 5a57 | 3-Cl-C₆H₄-NH- | $C_{26}H_{26}Cl_2N_2O$ | 453.42 | 453.1 |
| 5a58 | 4-F-C₆H₄-NH- | $C_{26}H_{26}ClFN_2O$ | 436.96 | 437.1 |
| 5a59 | 3,4-diCl-C₆H₃-NH- | $C_{26}H_{25}Cl_3N_2O$ | 487.86 | 487.1 |
| 5a60 | biphenyl-2-yl-NH- | $C_{32}H_{31}ClN_2O$ | 495.07 | 495.1 |
| 5a61 | (R)-1-(4-nitrophenyl)ethyl-NH- | $C_{28}H_{30}ClN_3O_3$ | 492.02 | 492.1 |

-continued
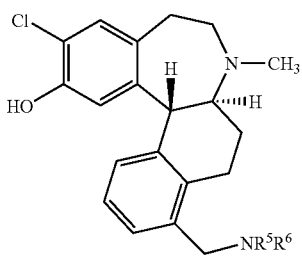
5a
| Cpd. # | NR⁵R⁶ | Molecular Formula | Mol. Wt. | Obs. (M + 1)⁺ |
|---|---|---|---|---|
| 5a62 | (1-(naphthalen-2-yl)ethyl)amino | $C_{32}H_{33}ClN_2O$ | 497.09 | 497.1 |
| 5a63 | N-ethyl-N-(pyridin-4-ylmethyl)amino | $C_{28}H_{32}ClN_3O$ | 462.04 | 462.1 |
| 5a64 | (2-(4-nitrophenyl)ethyl)amino | $C_{28}H_{30}ClN_3O_3$ | 492.02 | 492.1 |
| 5a65 | (2-(pyridin-3-yl)ethyl)amino | $C_{27}H_{30}ClN_3O$ | 448.01 | 448.1 |
| 5a66 | n-BuNH— | $C_{24}H_{31}ClN_2O$ | 398.98 | 399.1 |
| 5a67 | isobutylamino | $C_{24}H_{31}ClN_2O$ | 398.98 | 399.1 |
| 5a68 | Et₂N— | $C_{24}H_{31}ClN_2O$ | 398.98 | 399.1 |
| 5a69 | (4-phenylbutan-2-yl)amino | $C_{30}H_{35}ClN_2O$ | 475.08 | 475.1 |
| 5a70 | (2-methoxyethyl)amino | $C_{23}H_{29}ClN_2O_2$ | 400.95 | 401.1 |
| 5a71 | MeNH— | $C_{21}H_{25}ClN_2O$ | 356.90 | 357.1 |

The following compounds can be prepared by analogous procedures on regioisomeric starting materials:
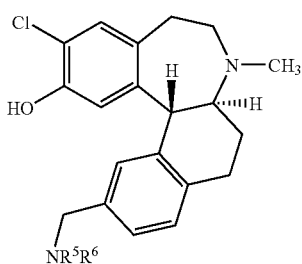
5b
| Cpd. # | NR⁵R⁶ | Mol. Formula | Mol. Wt. | Obs. Mass (M + 1)⁺ |
|---|---|---|---|---|
| 5b1 | -NH-Ph | $C_{26}H_{27}ClN_2O$ | 418.97 | 419.1 |
| 5b2 | piperazine-CH₂-benzodioxole | $C_{32}H_{36}ClN_3O_3$ | 546.12 | 546.1 |
| 5b3 | N(CH₂CH₂Ph)(CH₂Ph) | $C_{35}H_{37}ClN_2O$ | 537.15 | 537.1 |
| 5b4 | pyrrolidinyl | $C_{24}H_{29}ClN_2O$ | 396.97 | 397.1 |
| 5b5 | N(CH₃)(CH₂Ph) | $C_{28}H_{31}ClN_2O$ | 447.03 | 447.1 |

-continued
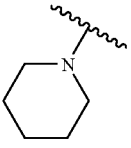
| Cpd. # | NR⁵R⁶ | Mol. Formula | Mol. Wt. | Obs. Mass (M + 1)⁺ |
|---|---|---|---|---|
| 5b6 | 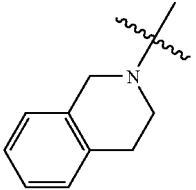 | C₂₅H₃₁ClN₂O | 410.99 | 411.1 |
| 5b7 | 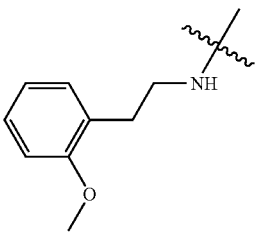 | C₂₉H₃₁ClN₂O | 459.04 | 459.1 |
| 5b8 | 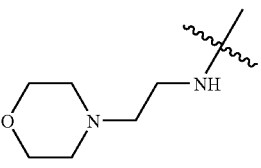 | C₂₉H₃₃ClN₂O₂ | 477.05 | 477.1 |
| 5b9 | 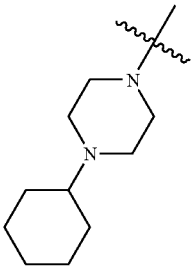 | C₂₆H₃₄ClN₃O₂ | 456.03 | 456.1 |
| 5b10 | 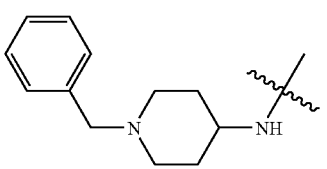 | C₃₀H₄₀ClN₃O | 494.13 | 494.1 |
| 5b11 |  | C₃₂H₃₈ClN₃O | 516.13 | 516.1 |

-continued
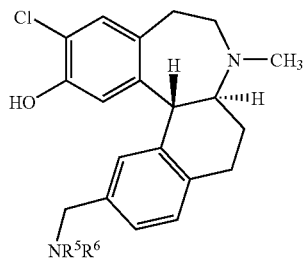
5b
| Cpd. # | NR⁵R⁶ | Mol. Formula | Mol. Wt. | Obs. Mass (M + 1)⁺ |
|---|---|---|---|---|
| 5b12 | 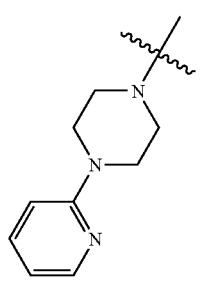 | $C_{29}H_{33}ClN_4O$ | 489.07 | 489.1 |
| 5b13 | 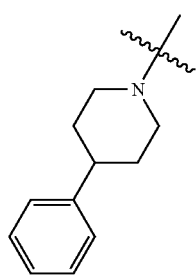 | $C_{31}H_{35}ClN_2O$ | 487.09 | 487.1 |
| 5b14 | 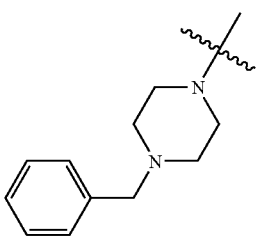 | $C_{31}H_{36}ClN_3O$ | 502.11 | 502.1 |
| 5b15 | 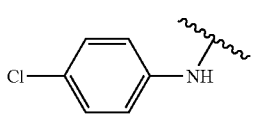 | $C_{26}H_{26}Cl_2N_2O$ | 453.42 | 453.1 |
| 5b16 | 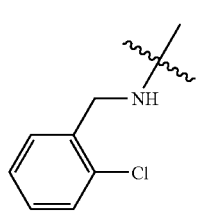 | $C_{27}H_{28}Cl_2N_2O$ | 467.44 | 467.1 |

-continued
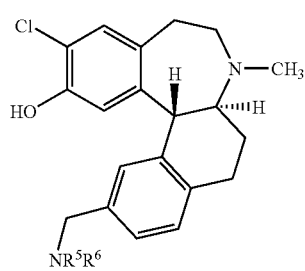
5b
| Cpd. # | NR$^5$R$^6$ | Mol. Formula | Mol. Wt. | Obs. Mass (M + 1)$^+$ |
|---|---|---|---|---|
| 5b17 | | C$_{24}$H$_{31}$ClN$_2$O | 398.98 | 399.1 |
| 5b18 | | C$_{27}$H$_{29}$ClN$_2$O | 433.00 | 433.1 |
| 5b19 | | C$_{26}$H$_{33}$ClN$_2$O | 425.02 | 425.1 |
| 5b20 | | C$_{31}$H$_{31}$ClN$_2$O | 483.06 | 483.1 |
| 5b21 | | C$_{27}$H$_{27}$ClN$_2$O$_3$ | 462.98 | 463.1 |
| 5b22 | | C$_{34}$H$_{35}$ClN$_2$O | 523.12 | 523.1 |

-continued
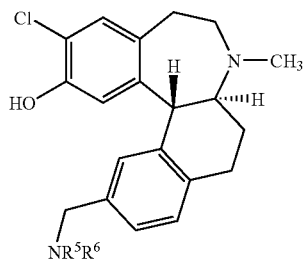
5b
| Cpd. # | NR<sup>5</sup>R<sup>6</sup> | Mol. Formula | Mol. Wt. | Obs. Mass $(M+1)^+$ |
|---|---|---|---|---|
| 5b23 | 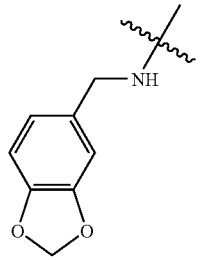 | $C_{28}H_{29}ClN_2O_3$ | 477.01 | 477.1 |
| 5b24 | 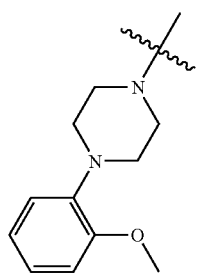 | $C_{31}H_{36}ClN_3O_2$ | 518.10 | 518.1 |
| 5b25 | 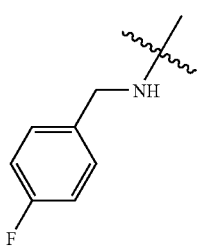 | $C_{27}H_{28}ClFN_2O$ | 450.99 | 451.1 |
| 5b26 | 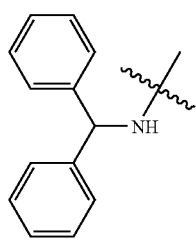 | $C_{33}H_{33}ClN_2O$ | 509.10 | 509.1 |

-continued
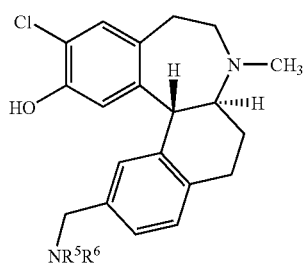
5b
| Cpd. # | NR⁵R⁶ | Mol. Formula | Mol. Wt. | Obs. Mass $(M+1)^+$ |
|---|---|---|---|---|
| 5b27 | 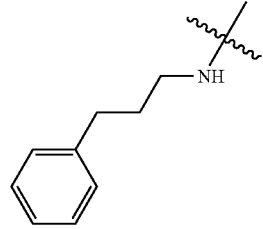 | $C_{29}H_{33}ClN_2O$ | 461.05 | 461.1 |
| 5b28 | 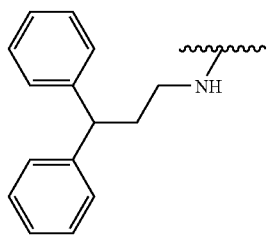 | $C_{35}H_{37}ClN_2O$ | 537.15 | 537.1 |
| 5b29 | 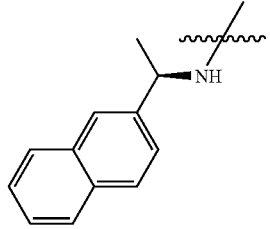 | $C_{32}H_{33}ClN_2O$ | 497.09 | 497.1 |
| 5b30 | 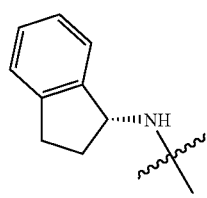 | $C_{29}H_{31}ClN_2O$ | 459.04 | 459.1 |

-continued
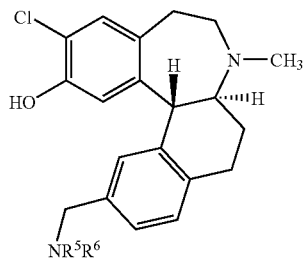
5b
| Cpd. # | NR⁵R⁶ | Mol. Formula | Mol. Wt. | Obs. Mass (M + 1)⁺ |
|---|---|---|---|---|
| 5b31 | 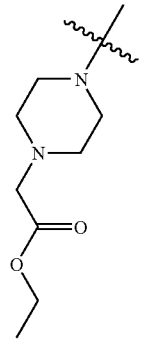 | $C_{28}H_{36}ClN_3O_3$ | 498.07 | 498.1 |
| 5b32 | 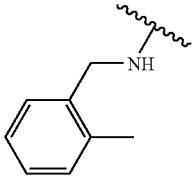 | $C_{28}H_{31}ClN_2O$ | 447.03 | 447.1 |
| 5b33 | 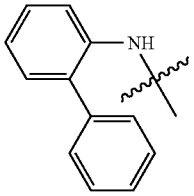 | $C_{32}H_{31}ClN_2O$ | 495.07 | 495.1 |
| 5b34 | 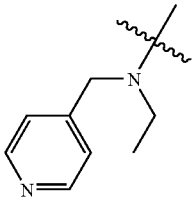 | $C_{28}H_{32}ClN_3O$ | 462.04 | 462.1 |
| 5b35 | 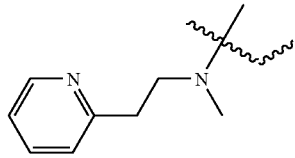 | $C_{28}H_{32}ClN_3O$ | 462.04 | 462.1 |

-continued
| Cpd. # | NR⁵R⁶ | Mol. Formula | Mol. Wt. | Obs. Mass $(M + 1)^+$ |
|---|---|---|---|---|
| 5b36 |  | $C_{27}H_{36}ClN_3O$ | 454.06 | 454.1 |
| 5b37 |  | $C_{30}H_{35}ClN_2O$ | 475.08 | 475.1 |
| 5b38 |  | $C_{28}H_{30}Cl_2N_2O$ | 481.47 | 481.1 |
| 5b39 | 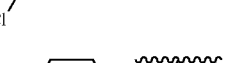 | $C_{28}H_{30}Cl_2N_2O$ | 481.47 | 481.1 |
| 5b40 |  | $C_{29}H_{28}ClN_3O$ | 470.02 | 470.1 |
| 5b41 | | $C_{27}H_{27}Cl_3N_2O$ | 501.89 | 503.1 |

-continued
| Cpd. # | NR5R6 | Mol. Formula | Mol. Wt. | Obs. Mass (M + 1)+ |
|---|---|---|---|---|
| 5b42 | 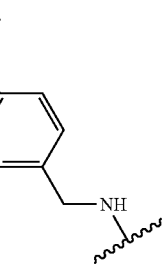 | $C_{27}H_{30}ClN_3O$ | 448.01 | 448.1 |
| 5b43 | 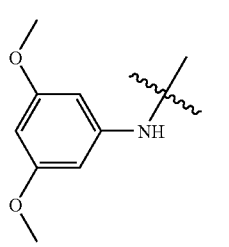 | $C_{29}H_{33}ClN_2O_3$ | 493.05 | 493.1 |
| 5b44 | 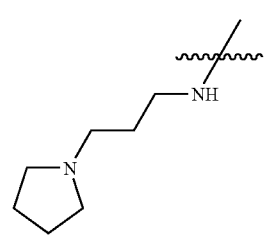 | $C_{28}H_{31}ClN_2O_3$ | 479.02 | 479.1 |
| 5b45 | 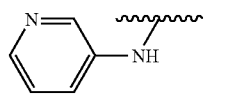 | $C_{27}H_{36}ClN_3O$ | 454.06 | 454.1 |
| 5b46 | 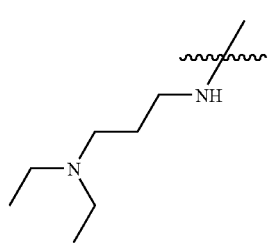 | $C_{25}H_{26}ClN_3O$ | 419.96 | 420.1 |
| 5b47 | | $C_{27}H_{38}ClN_3O$ | 456.08 | 456.1 |

-continued
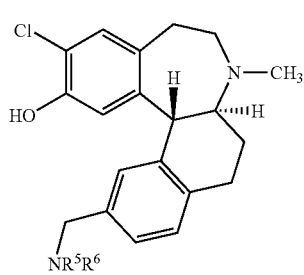
5b
| Cpd. # | NR⁵R⁶ | Mol. Formula | Mol. Wt. | Obs. Mass (M + 1)⁺ |
|---|---|---|---|---|
| 5b48 | 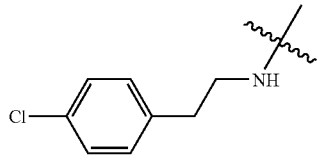 | $C_{28}H_{30}Cl_2N_2O$ | 481.47 | 481.1 |
| 5b49 | 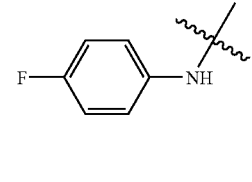 | $C_{26}H_{26}ClFN_2O$ | 436.96 | 437.1 |
| 5b50 | 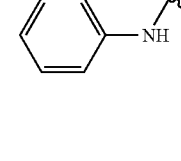 | $C_{26}H_{26}Cl_2N_2O$ | 453.42 | 453.1 |
| 5b51 | 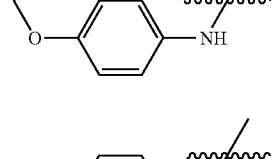 | $C_{28}H_{29}ClN_2O_3$ | 477.01 | 477.1 |
| 5b52 | 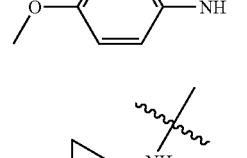 | $C_{27}H_{29}ClN_2O_2$ | 449.00 | 449.1 |
| 5b53 | 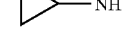 | $C_{23}H_{27}ClN_2O$ | 382.94 | 383.1 |

The following compounds can also be prepared using analogous methods:
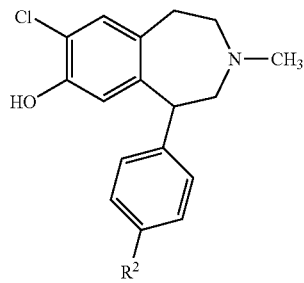
5c
| Cpd. # | R² | Molecular Formula | Mol. Wt. | Obs. Mass (M + 1)⁺ |
|---|---|---|---|---|
| 5c1 | H₃C-O-C₆H₄-NH-CH₂- | $C_{25}H_{27}ClN_2O_2$ | 422.9 | 423 |
| 5c2 | benzo[1,3]dioxol-5-ylmethyl-piperazinyl-CH₂- | $C_{30}H_{34}ClN_3O_3$ | 520.1 | 520 |
| 5c3 | PhNH-CH₂- | $C_{24}H_{25}ClN_2O$ | 392.9 | 393 |
| 5c4 | 4-Cl-C₆H₄-NH-CH₂- | $C_{24}H_{24}Cl_2N_2O$ | 427.4 | 427 |
| 5c5 | 1,2,3,4-tetrahydroisoquinolin-2-yl-CH₂- | $C_{27}H_{29}ClN_2O$ | 433.0 | 433 |
| 5c6 | 1-ethyl-pyrrolidin-2-ylmethyl-NH-CH₂- | $C_{25}H_{34}ClN_3O$ | 428.0 | 428 |
| 5c7 | 2-Cl-6-F-C₆H₃-CH₂-NH-CH₂- | $C_{25}H_{25}Cl_2FN_2O$ | 459.4 | 460 |

-continued
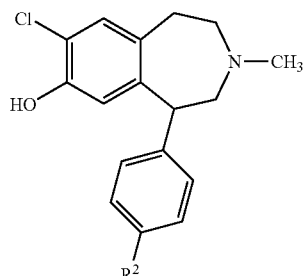
5c
| Cpd. # | R² | Molecular Formula | Mol. Wt. | Obs. Mass (M + 1)⁺ |
|---|---|---|---|---|
| 5c8 | N-benzyl-N-phenethyl-aminomethyl | $C_{33}H_{35}ClN_2O$ | 511.1 | 511 |
| 5c9 | piperidin-1-ylmethyl | $C_{23}H_{29}ClN_2O$ | 385.0 | 385 |
| 5c10 | (indan-5-ylamino)methyl | $C_{27}H_{29}ClN_2O$ | 433.0 | 433 |
| 5c11 | (2-methylbut-3-yn-2-ylamino)methyl | $C_{23}H_{27}ClN_2O$ | 382.9 | 383 |
| 5c12 | [benzyl(2-hydroxyethyl)amino]methyl | $C_{27}H_{31}ClN_2O_2$ | 451.0 | 451 |
| 5c13 | [1-(4-nitrophenyl)ethylamino]methyl | $C_{26}H_{28}ClN_3O_3$ | 466.0 | 466 |
| 5c14 | [ethyl(pyridin-4-ylmethyl)amino]methyl | $C_{26}H_{30}ClN_3O$ | 436.0 | 436 |

-continued

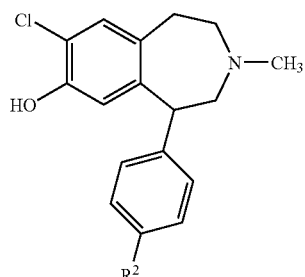

5c

| Cpd. # | R² | Molecular Formula | Mol. Wt. | Obs. Mass (M + 1)⁺ |
|---|---|---|---|---|
| 5c15 | (2,5-dimethylpiperazin-1-yl)methyl | C₂₄H₃₂ClN₃O | 414.0 | 414 |
| 5c16 | (1-cyclohexylethylamino)methyl | C₂₆H₃₅ClN₂O | 427.0 | 427 |
| 5c17 | (N-methyl-N-phenethylamino)methyl | C₂₇H₃₁ClN₂O | 435.0 | 435 |
| 5c18 | (cyclobutylamino)methyl | C₂₂H₂₇ClN₂O | 370.9 | 371 |
| 5c19 | (2-phenylpropan-2-ylamino)methyl | C₂₇H₃₁ClN₂O | 435.0 | 435 |
| 5c20 | (3,3-diphenylpropylamino)methyl | C₃₃H₃₅ClN₂O | 511.1 | 511 |
| 5c21 | (benzo[d][1,3]dioxol-5-ylamino)methyl | C₂₅H₂₅ClN₂O₃ | 436.9 | 437 |

-continued
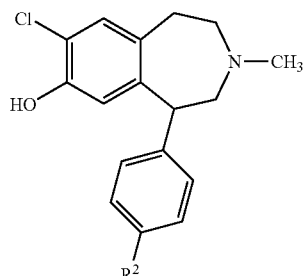
5c
| Cpd. # | R² | Molecular Formula | Mol. Wt. | Obs. Mass (M + 1)⁺ |
|---|---|---|---|---|
| 5c22 | | $C_{27}H_{31}ClN_2O$ | 435.0 | 435 |
| 5c23 | | $C_{30}H_{35}ClN_2O$ | 475.1 | 475 |
| 5c24 | | $C_{30}H_{31}ClN_2O$ | 471.0 | 471 |
| 5c25 | | $C_{28}H_{31}ClN_2O$ | 447.0 | 447 |
| 5c26 | | $C_{27}H_{31}ClN_2O$ | 435.0 | 435 |
| 5c27 | | $C_{27}H_{31}ClN_2O_3$ | 467.0 | 467 |

-continued
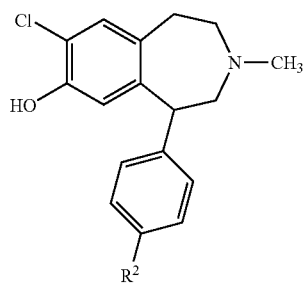
5c
| Cpd. # | R² | Molecular Formula | Mol. Wt. | Obs. Mass (M + 1)⁺ |
|---|---|---|---|---|
| 5c28 | | C₂₇H₂₉ClN₂O | 433.0 | 433 |
| 5c29 | | C₂₇H₃₁ClN₂O₂ | 451.0 | 451 |
| 5c30 | | C₂₇H₃₁ClN₂O | 435.0 | 435 |
| 5c31 | | C₂₇H₃₁ClN₂O₂ | 451.0 | 451 |
| 5c32 | | C₂₄H₃₁ClN₂O | 399.0 | 399 |
| 5c33 | | C₂₆H₂₉ClN₂O₂ | 437.0 | 437 |
| 5c34 | | C₂₆H₂₉ClN₂O | 421.0 | 421 |
| 5c35 | | C₂₅H₂₅Cl₃N₂O | 475.9 | 476 |

-continued
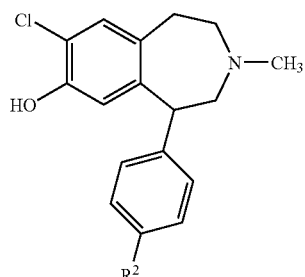
5c
| Cpd. # | R² | Molecular Formula | Mol. Wt. | Obs. Mass (M + 1)⁺ |
|---|---|---|---|---|
| 5c36 | 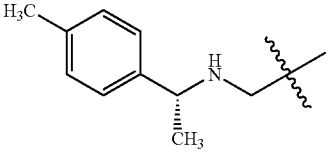 | C₂₇H₃₁ClN₂O | 435.0 | 435 |
| 5c37 | 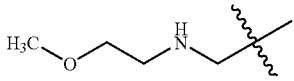 | C₂₁H₂₇ClN₂O₂ | 374.9 | 375 |
| 5c38 | 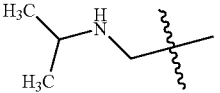 | C₂₁H₂₇ClN₂O | 358.9 | 359 |
| 5c39 | 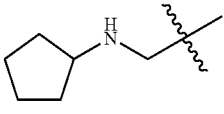 | C₂₃H₂₉ClN₂O | 385.0 | 385 |
| 5c40 | 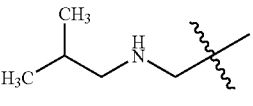 | C₂₂H₂₉ClN₂O | 372.9 | 373 |
| 5c41 | 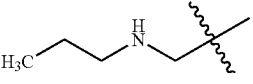 | C₂₁H₂₇ClN₂O | 358.9 | 359 |
| 5c42 | 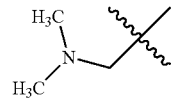 | C₂₀H₂₅ClN₂O | 344.9 | 345 |

Method 6

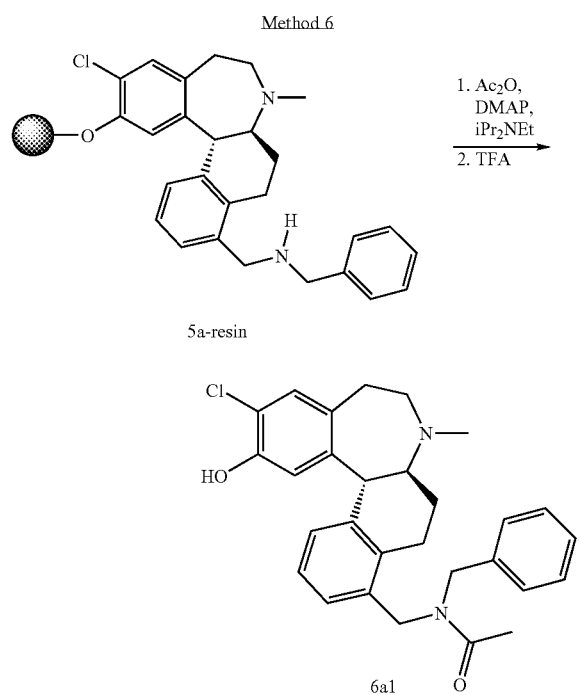

To a preconditioned mixture of 31 mg of 5a attached to resin (0.62 mmol/g) in 1.2 mL of anhydrous dichloromethane was added 0.020 mL (0.11 mmol) I—Pr$_2$Net, 2 mg (0.016 mmol) dimethylaminopyridine (DMAP), and 0.020 mL (0.21 mmol) of acetic anhydride. The reaction was agitated for 20 hours at ambient temperature. The liquid was drained, and the resin was washed with three times with methanol, three times with THF, and three times with dichloromethane. The product was cleaved from the solid support by treatment of the resin with 3% TFA in dichloromethane (1 mL). The liquid was drained, and the resin was washed with three times with dichloromethane. The combined filtrates were concentrated to dryness to provide 0.005 g of 6a1 as a solid: LCMS: m/z calcd for $C_{29}H_{32}ClN_2O_2^+$ (M+1)$^+$=475.2; obsvd m/z=475.3.

The following compounds can be prepared by analogous methods:

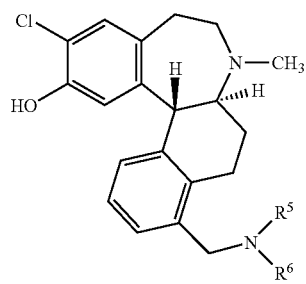

6a

| Cpd. # | R$^6$ | R$^5$ | Mol. Formula | Mol. Wt. | Obs. Mass (M + 1)$^+$ |
|---|---|---|---|---|---|
| 6a2 | –CH$_2$CH$_2$–C$_6$H$_5$ | –C(O)CH$_3$ | $C_{30}H_{33}ClN_2O_2$ | 489.1 | 489 |
| 6a3 | –CH$_2$–C$_6$H$_4$–F | –C(O)CH$_3$ | $C_{29}H_{30}ClFN_2O_2$ | 493.0 | 493.1 |
| 6a4 | –CH$_2$–cyclohexyl | –C(O)CH(CH$_3$)$_2$ | $C_{30}H_{39}ClN_2O_2$ | 495.1 | 495.27 |

-continued
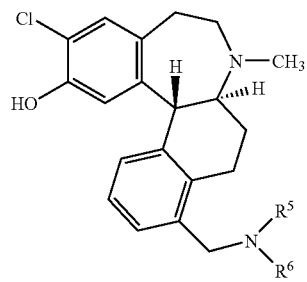
| Cpd. # | R6 | R5 | Mol. Formula | Mol. Wt. | Obs. Mass (M + 1)+ |
|---|---|---|---|---|---|
| 6a5 | phenyl | benzoyl | $C_{33}H_{31}ClN_2O_2$ | 523.1 | 523.29 |
| 6a6 | phenyl | acetyl | $C_{28}H_{29}ClN_2O_2$ | 461.0 | 461.25 |
| 6a7 | cyclopropylmethyl | acetyl | $C_{26}H_{31}ClN_2O_2$ | 439.0 | 439.24 |
| 6a8 | cyclohexyl | acetyl | $C_{28}H_{35}ClN_2O_2$ | 467.1 | 467.26 |
| 6a9 | propyl | acetyl | $C_{25}H_{31}ClN_2O_2$ | 427.0 | 427.23 |
| 6a10 | phenyl | isobutyryl | $C_{30}H_{33}ClN_2O_2$ | 489.1 | 489.27 |
| 6a11 | cyclopropyl | benzoyl | $C_{30}H_{31}ClN_2O_2$ | 487.0 | 487.27 |

-continued
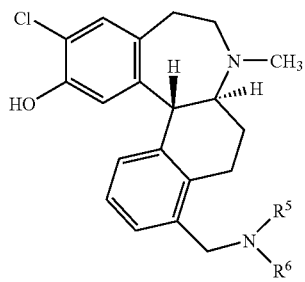
6a
| Cpd. # | R6 | R5 | Mol. Formula | Mol. Wt. | Obs. Mass (M + 1)+ |
|---|---|---|---|---|---|
| 6a12 | benzyl | benzoyl | $C_{34}H_{33}ClN_2O_2$ | 537.1 | 537.3 |
| 6a13 | cyclohexylmethyl | benzoyl | $C_{33}H_{37}ClN_2O_2$ | 529.1 | 529.29 |
| 6a14 | n-propyl | benzoyl | $C_{30}H_{33}ClN_2O_2$ | 489.1 | 489.27 |
| 6a15 | n-propyl | isobutyryl | $C_{27}H_{35}ClN_2O_2$ | 455.0 | 455.25 |
| 6a16 | cyclopropylmethyl | isobutyryl | $C_{28}H_{35}ClN_2O_2$ | 467.1 | 467.26 |
| 6a17 | cyclopropyl | isobutyryl | $C_{27}H_{33}ClN_2O_2$ | 453.0 | 453.25 |

-continued
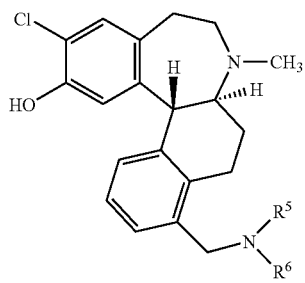
6a
| Cpd. # | R⁶ | R⁵ | Mol. Formula | Mol. Wt. | Obs. Mass (M + 1)⁺ |
|---|---|---|---|---|---|
| 6a18 | benzyl | isopropyl ketone | $C_{31}H_{35}ClN_2O_2$ | 503.1 | 503.28 |
| 6a19 | cyclopropyl | methyl ketone | $C_{25}H_{29}ClN_2O_2$ | 425.0 | 425.23 |
| 6a20 | cyclopropylmethyl | phenyl ketone | $C_{31}H_{33}ClN_2O_2$ | 501.1 | 501.28 |
| 6a21 | cyclobutyl | methyl ketone | $C_{26}H_{31}ClN_2O_2$ | 439.0 | 439.1 |
| 6a22 | 4-fluorobenzyl | methyl ketone | $C_{28}H_{28}ClFN_2O_2$ | 479.0 | 479.1 |

The following compounds were prepared from regioisomeric starting materials:
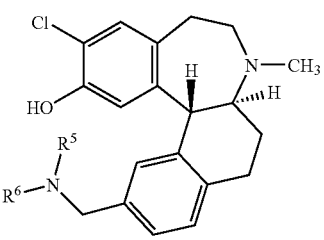
6b
| Cpd. # | R⁶ | R⁵ | Mol. Formula | Mol. Wt. | Obs. Mass (M + 1)⁺ |
|---|---|---|---|---|---|
| 6b1 | benzyl | benzoyl | $C_{34}H_{33}ClN_2O_2$ | 537.1 | 537.3 |
| 6b2 | cyclopropylmethyl | isobutyryl | $C_{27}H_{33}ClN_2O_2$ | 453.0 | 453.3 |
| 6b3 | benzyl | acetyl | $C_{29}H_{31}ClN_2O_2$ | 475.0 | 475.3 |
| 6b4 | cyclopropylmethyl | isobutyryl | $C_{28}H_{35}ClN_2O_2$ | 467.1 | 467.3 |
| 6b5 | phenyl | isobutyryl | $C_{30}H_{33}ClN_2O_2$ | 489.1 | 489.3 |
| 6b6 | cyclohexyl | isobutyryl | $C_{30}H39ClN_2O_2$ | 495.1 | 495.3 |
| 6b7 | phenyl | acetyl | $C_{28}H_{29}ClN_2O_2$ | 461.0 | 461.3 |

-continued
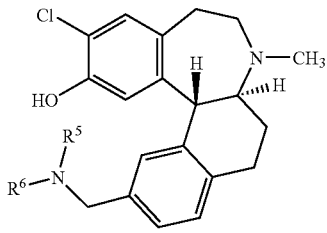
6b
| Cpd. # | R⁶ | R⁵ | Mol. Formula | Mol. Wt. | Obs. Mass (M + 1)⁺ |
|---|---|---|---|---|---|
| 6b8 | cyclopropylmethyl | acetyl | $C_{26}H_{31}ClN_2O_2$ | 439.0 | 439.2 |
| 6b9 | cyclopropyl | acetyl | $C_{25}H_{29}ClN_2O_2$ | 425.0 | 425.2 |
| 6b10 | benzyl | isobutyryl | $C_{31}H_{35}ClN_2O_2$ | 503.1 | 503.3 |
| 6b11 | cyclopropyl | benzoyl | $C_{30}H_{31}ClN_2O_2$ | 487.0 | 487.3 |
| 6b12 | cyclohexyl | acetyl | $C_{28}H_{35}ClN_2O_2$ | 467.1 | 467.3 |
| 6b13 | propyl | acetyl | $C_{25}H_{31}ClN_2O_2$ | 427.0 | 427.2 |
| 6b14 | cyclohexyl | benzoyl | $C_{33}H_{37}ClN_2O_2$ | 529.1 | 529.3 |

-continued
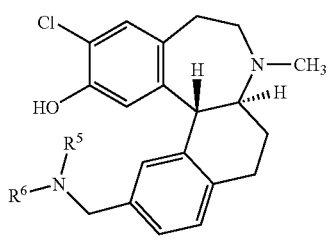
6b
| Cpd. # | R⁶ | R⁵ | Mol. Formula | Mol. Wt. | Obs. Mass (M + 1)⁺ |
|---|---|---|---|---|---|
| 6b15 | phenyl | benzoyl | $C_{33}H_{31}ClN_2O_2$ | 523.1 | 523.3 |
| 6b16 | cyclopropylmethyl | benzoyl | $C_{31}H_{33}ClN_2O_2$ | 501.1 | 501.3 |
| 6b17 | propyl | benzoyl | $C_{30}H_{33}ClN_2O_2$ | 489.1 | 489.3 |
| 6b18 | propyl | isobutyryl | $C_{27}H_{35}ClN_2O_2$ | 455.0 | 455.3 |

The following compounds were prepared analogously from bicyclic starting materials:
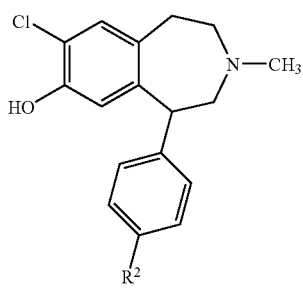
6c
| Cpd. # | R² | Mol. Formula | Mol. Wt. | Obs. Mass (M + 1)⁺ |
|---|---|---|---|---|
| 6c1 | 2,4-difluoro-N-benzylbenzamide | $C_{32}H_{29}ClF_2N_2O_2$ | 547.1 | 547 |
| 6c2 | N-benzylacetamide | $C_{27}H_{29}ClN_2O_2$ | 449.0 | 449 |
| 6c3 | 4-methyl-N-cyclohexylbenzamide | $C_{32}H_{37}ClN_2O_2$ | 517.1 | 517 |
| 6c4 | 4-trifluoromethoxy-N-benzylbenzamide | $C_{33}H_{30}ClF_3N_2O_3$ | 595.1 | 595 |
| 6c5 | N-benzylfuran-2-carboxamide | $C_{30}H_{29}ClN_2O_3$ | 501.0 | 501 |

-continued
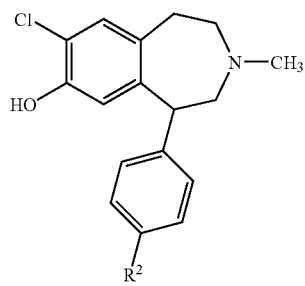
6c
| Cpd. # | R² | Mol. Formula | Mol. Wt. | Obs. Mass (M + 1)⁺ |
|---|---|---|---|---|
| 6c6 | cyclohexyl-N(COCH₃)-CH₂- | $C_{26}H_{33}ClN_2O_2$ | 441.0 | 441 |
| 6c7 | benzyl-N(CO-CH(Et)₂)-CH₂- | $C_{31}H_{37}ClN_2O_2$ | 505.1 | 505 |
| 6c8 | benzyl-N(CO-cyclohexyl)-CH₂- | $C_{32}H_{37}ClN_2O_2$ | 517.1 | 517 |
| 6c9 | n-Pr-N(COCH₃)-CH₂- | $C_{23}H_{29}ClN_2O_2$ | 401.0 | 401 |
| 6c10 | (4-F₃CO-C₆H₄)-CO-N(n-Pr)-CH₂- | $C_{29}H_{30}ClF_3N_2O_3$ | 547.0 | 547 |
| 6c11 | (3-Cl-C₆H₄)-CO-N(n-Pr)-CH₂- | $C_{28}H_{30}Cl_2N_2O_2$ | 497.5 | 497 |

-continued
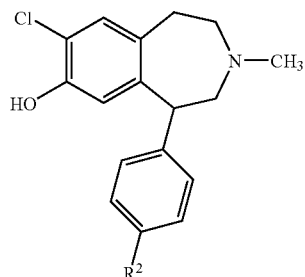
6c
| Cpd. # | R² | Mol. Formula | Mol. Wt. | Obs. Mass (M + 1)⁺ |
|---|---|---|---|---|
| 6c12 | (4-methylbenzamide, N-propyl) | $C_{29}H_{33}ClN_2O_2$ | 477.1 | 477 |
| 6c13 | (2,4-difluorobenzamide, N-propyl) | $C_{28}H_{29}ClF_2N_2O_2$ | 499.0 | 499 |
| 6c14 | (furan-2-carboxamide, N-cyclohexyl) | $C_{29}H_{33}ClN_2O_3$ | 493.1 | 493 |
| 6c15 | (cyclohexanecarboxamide, N-propyl) | $C_{28}H_{37}ClN_2O_2$ | 469.1 | 469 |
| 6c16 | (furan-2-carboxamide, N-propyl) | $C_{26}H_{29}ClN_2O_3$ | 453.0 | 453 |
| 6c17 | (cyclobutanecarboxamide, N-benzyl) | $C_{30}H_{33}ClN_2O_2$ | 489.1 | 489 |

-continued
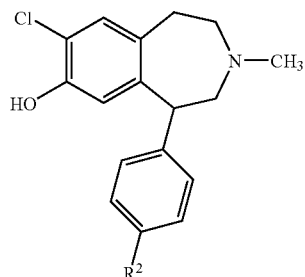
6c
| Cpd. # | R² | Mol. Formula | Mol. Wt. | Obs. Mass (M + 1)⁺ |
|---|---|---|---|---|
| 6c18 | 3-Cl-C₆H₄-C(O)-N(cyclohexyl)-CH₂- | $C_{31}H_{34}Cl_2N_2O_2$ | 537.5 | 537 |
| 6c19 | 2,4-F₂-C₆H₃-C(O)-N(cyclohexyl)-CH₂- | $C_{31}H_{33}ClF_2N_2O_2$ | 539.1 | 539 |
| 6c20 | 4-F₃CO-C₆H₄-C(O)-N(cyclohexyl)-CH₂- | $C_{32}H_{34}ClF_3N_2O_3$ | 587.1 | 587 |
| 6c21 | 3-Cl-C₆H₄-C(O)-N(benzyl)-CH₂- | $C_{32}H_{30}Cl_2N_2O_2$ | 545.5 | 545 |
| 6c22 | 4-H₃C-C₆H₄-C(O)-N(benzyl)-CH₂- | $C_{33}H_{33}ClN_2O_2$ | 525.1 | 525 |

-continued
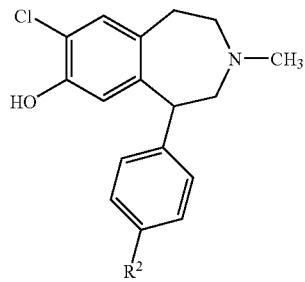
6c
| Cpd. # | R² | Mol. Formula | Mol. Wt. | Obs. Mass (M + 1)⁺ |
|---|---|---|---|---|
| 6c23 | | $C_{31}H_{41}ClN_2O_2$ | 509.1 | 509 |
| 6c24 | | $C_{27}H_{37}ClN_2O_2$ | 457.1 | 457 |
| 6c25 | | $C_{30}H_{41}ClN_2O_2$ | 497.1 | 497 |
| 6c26 | | $C_{24}H_{29}ClN_2O_2$ | 413.0 | 413 |
| 6c27 | | $C_{29}H_{31}ClN_2O_2$ | 475.0 | 475 |
| 6c28 | | $C_{31}H_{35}ClN_2O_2$ | 503 | 503 |

Method 7

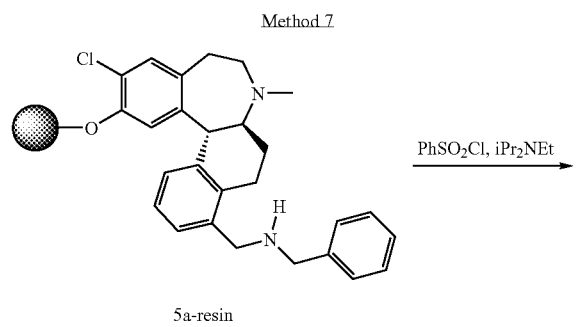

To a preconditioned mixture of 31 mg of 5a attached to resin (0.62 mmol/g) in 1.2 mL of anhydrous dichloromethane was added 0.017 mL (0.098 mmol) of I—Pr$_2$NEt followed by 0.012 mL (0.098 mmol) of benzenesulfonylchloride. The reaction was agitated for 20 hours at ambient temperature. The liquid was drained and the resin was washed with three times each with methanol, THF, and dichloromethane. The product was cleaved from the solid support by treatment of the resin with 3% TFA in dichloromethane (1 mL). The liquid was drained and the resin was washed three times with dichloromethane. The combined filtrates were concentrated to dryness to provide 0.004 g of 7a1 as a tan solid: LCMS: m/z calcd for $C_{33}H_{34}ClN_2O_3S^+$ (M+1)$^+$=573.2; obsvd m/z=573.3.

The following compounds can be prepared analogously:

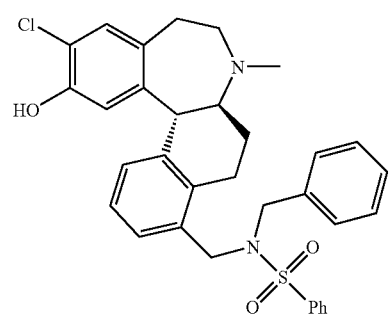

| Cpd. # | R$^5$ | R$^6$ | Mol. Formula | Mol. Wt. | Obs. Mass (M + 1)$^+$ |
|---|---|---|---|---|---|
| 7a2 | O=S(=O)CH$_3$ | cyclopropylmethyl | $C_{25}H_{31}ClN_2O_3S$ | 475.1 | 475.3 |
| 7a3 | O=S(=O)Ph | n-butyl | $C_{29}H_{33}ClN_2O_3S$ | 525.1 | 525.3 |
| 7a4 | O=S(=O)Ph | cyclopropylmethyl | $C_{30}H_{33}ClN_2O_3S$ | 537.1 | 537.3 |

-continued
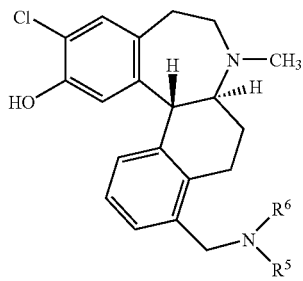
| Cpd. # | R⁵ | R⁶ | Mol. Formula | Mol. Wt. | Obs. Mass (M + 1)⁺ |
|---|---|---|---|---|---|
| 7a5 | phenylsulfonyl | cyclopropyl | $C_{29}H_{31}ClN_2O_3S$ | 523.1 | 523.3 |
| 7a6 | methylsulfonyl | n-pentyl | $C_{24}H_{31}ClN_2O_3S$ | 463.0 | 463.3 |
| 7a7 | methylsulfonyl | cyclopropyl | $C_{24}H_{29}ClN_2O_3S$ | 461.0 | 461.3 |
| 7a8 | phenylsulfonyl | cyclobutylmethyl | $C_{30}H_{33}ClN_2O_3S$ | 537.1 | 537.1 |
| 7a9 | methylsulfonyl | benzyl | $C_{28}H_{31}ClN_2O_3S$ | 511.1 | 511.3 |
| 7a10 | methylsulfonyl | cyclohexyl | $C_{27}H_{35}ClN_2O_3S$ | 503.1 | 503.3 |
| 7a11 | phenylsulfonyl | cyclohexyl | $C_{32}H_{37}ClN_2O_3S$ | 565.2 | 565.3 |

The following compounds can be prepared analogously with regioisomeric starting materials:
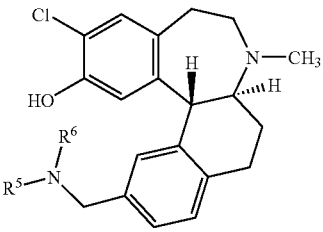
7b
| Cpd. # | R⁵ | R⁶ | Mol. Formula | Mol. Wt. | Obs. Mass (M + 1)⁺ |
|---|---|---|---|---|---|
| 7b1 | –S(O)₂CH₃ | –CH₂-cyclopropyl | $C_{25}H_{31}ClN_2O_3S$ | 475.1 | 475.3 |
| 7b2 | –S(O)₂Ph | –CH₂Ph | $C_{33}H_{33}ClN_2O_3S$ | 573.2 | 573.3 |
| 7b3 | –S(O)₂CH₃ | cyclopropyl | $C_{24}H_{29}ClN_2O_3S$ | 461.0 | 461.3 |
| 7b4 | –S(O)₂Ph | –CH₂-cyclopropyl | $C_{30}H_{33}ClN_2O_3S$ | 537.1 | 537.3 |
| 7b5 | –S(O)₂Ph | cyclohexyl | $C_{32}H_{37}ClN_2O_3S$ | 565.2 | 565.3 |
| 7b6 | –S(O)₂Ph | cyclopropyl | $C_{29}H_{31}ClN_2O_3S$ | 523.1 | 523.3 |
| 7b7 | –S(O)₂CH₃ | –CH₂Ph | $C_{28}H_{31}ClN_2O_3S$ | 511.1 | 511.3 |

-continued
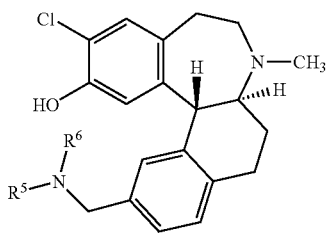
7b
| Cpd. # | R⁵ | R⁶ | Mol. Formula | Mol. Wt. | Obs. Mass (M + 1)⁺ |
|---|---|---|---|---|---|
| 7b8 | 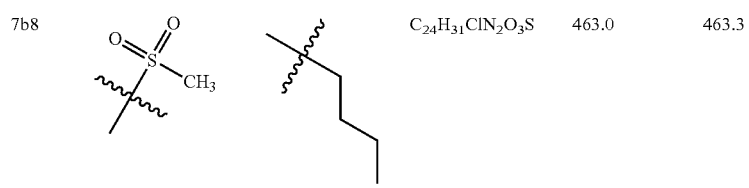 | | $C_{24}H_{31}ClN_2O_3S$ | 463.0 | 463.3 |
| 7b9 | 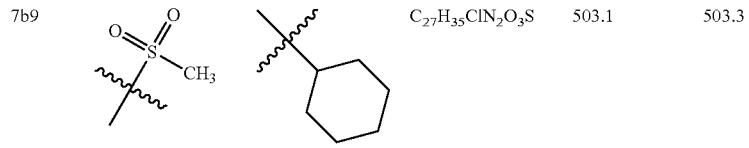 | | $C_{27}H_{35}ClN_2O_3S$ | 503.1 | 503.3 |
| 7b10 | 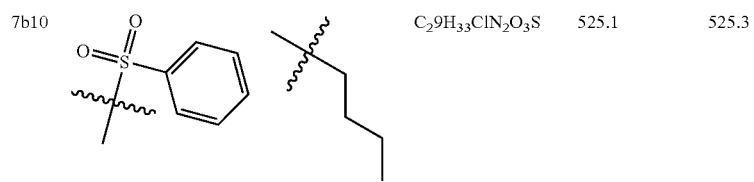 | | $C_{29}H_{33}ClN_2O_3S$ | 525.1 | 525.3 |
| 7b11 | 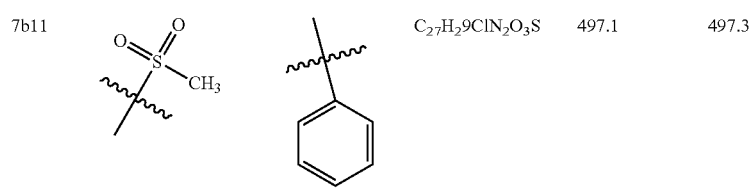 | | $C_{27}H_{29}ClN_2O_3S$ | 497.1 | 497.3 |

The following compounds can be prepared analogously with regioisomeric starting materials:
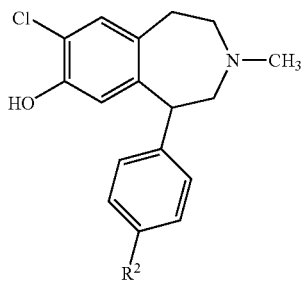
7c
| Cpd. # | R² | Mol. Formula | Mol. Wt. | Obs. Mass (M + 1)⁺ |
|---|---|---|---|---|
| 7c1 | | $C_{27}H_{31}ClN_2O_3S$ | 499.077 | 499 |
| 7c2 | | $C_{31}H_{31}ClN_2O_3S$ | 547.121 | 547 |
| 7c3 | | $C_{30}H_{35}ClN_2O_3S$ | 539.142 | 539 |
| 7c4 | | $C_{27}H_{30}BrClN_2O_3S$ | 577.973 | 578 |
| 7c5 | | $C_{31}H_{30}BrClN_2O_3S$ | 626.017 | 626 |

-continued
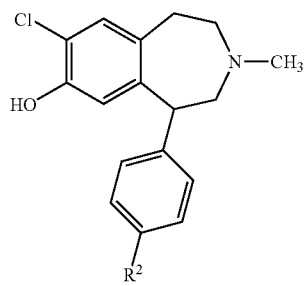
7c
| Cpd. # | R² | Mol. Formula | Mol. Wt. | Obs. Mass (M + 1)⁺ |
|---|---|---|---|---|
| 7c6 | N-cyclohexyl-N-(4-bromophenylsulfonyl) | $C_{30}H_{34}BrClN_2O_3S$ | 618.038 | 618 |
| 7c7 | N-benzyl-2-fluorophenylsulfonyl | $C_{31}H_{30}ClFN_2O_3S$ | 565.112 | 565 |
| 7c8 | 4-MeO-phenylsulfonyl, N-n-Pr | $C_{28}H_{33}ClN_2O_4S$ | 529.103 | 529 |
| 7c9 | 3-CF₃-phenylsulfonyl, N-cyclohexyl | $C_{31}H_{34}ClF_3N_2O_3S$ | 607.14 | 607 |
| 7c10 | 2-F-phenylsulfonyl, N-cyclohexyl | $C_{30}H_{34}ClFN_2O_3S$ | 557.133 | 557 |
| 7c11 | 3-CF₃-phenylsulfonyl, N-n-Pr | $C_{28}H_{30}ClF_3N_2O_3S$ | 567.075 | 567 |

-continued
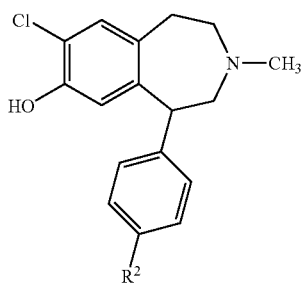
7c
| Cpd. # | R² | Mol. Formula | Mol. Wt. | Obs. Mass (M + 1)⁺ |
|---|---|---|---|---|
| 7c12 | 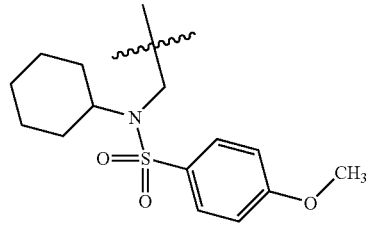 | $C_{31}H_{37}ClN_2O_4S$ | 569.169 | 69 |
| 7c13 | 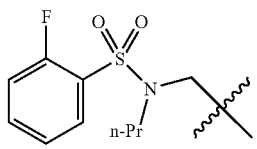 | $C_{27}H_{30}ClFN_2O_3S$ | 517.067 | 517 |
| 7c14 | 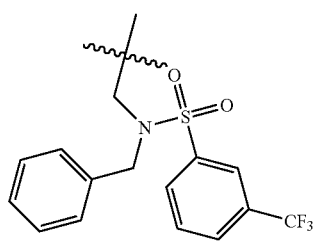 | $C_{32}H_{30}ClF_3N_2O_3S$ | 615.12 | 615 |
| 7c15 | 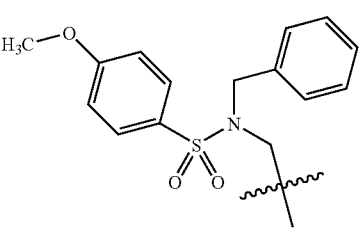 | $C_{32}H_{33}ClN_2O_4S$ | 577.148 | 577 |

-continued
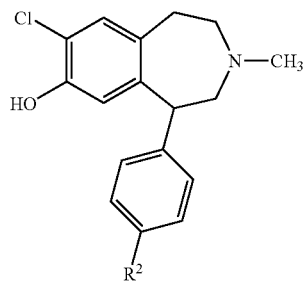
7c
| Cpd. # | R² | Mol. Formula | Mol. Wt. | Obs. Mass (M + 1)⁺ |
|---|---|---|---|---|
| 7c16 | 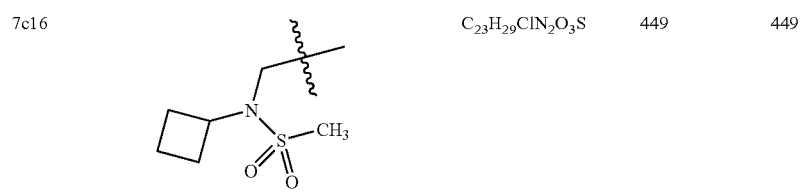 | $C_{23}H_{29}ClN_2O_3S$ | 449 | 449 |
| 7c17 | 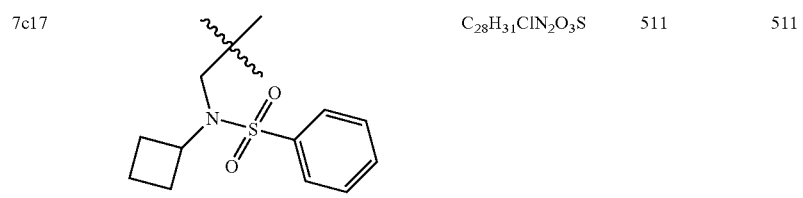 | $C_{28}H_{31}ClN_2O_3S$ | 511 | 511 |
| 7c18 | 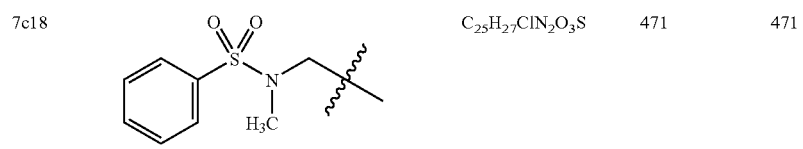 | $C_{25}H_{27}ClN_2O_3S$ | 471 | 471 |
| 7c19 | 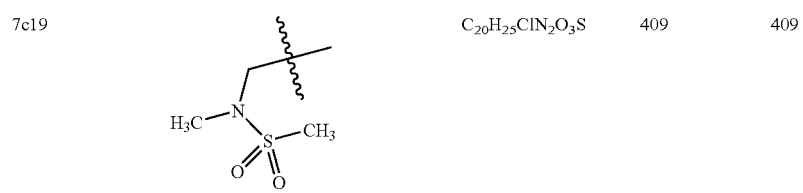 | $C_{20}H_{25}ClN_2O_3S$ | 409 | 409 |

Method 8

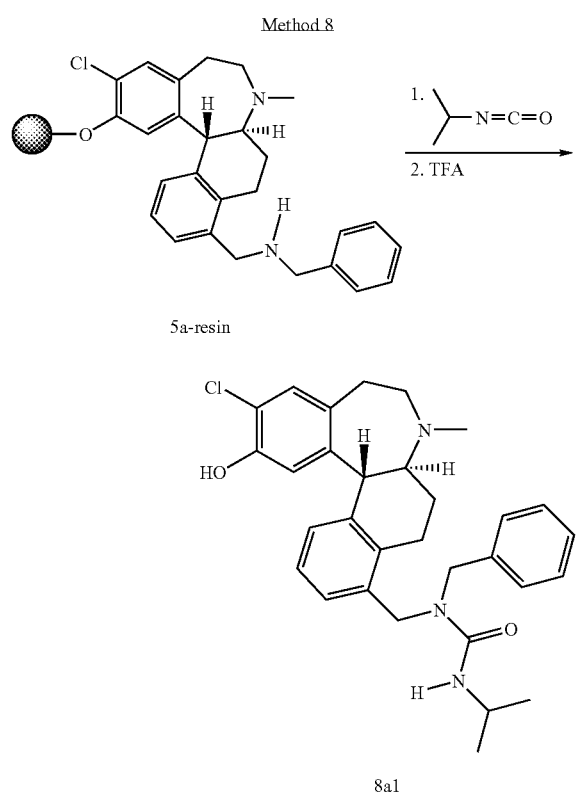

To a preconditioned mixture of 31 mg of 5a attached to resin (0.62 mmol/g) in 1.1 mL of anhydrous dichloromethane (2 mL) was added 0.010 mL (0.10 mmol) of isopropyl isocyante. The reaction was agitated for 20 hours at ambient temperature. The liquid was drained, and the resin was washed three times each with methanol, THF (3×), and dichloromethane. The product was cleaved from the solid support by treatment of the resin with 3% TFA in dichloromethane (1 mL). The liquid was drained, and the resin was washed three times with dichloromethane. The combined filtrates were concentrated to dryness to provide 0.004 g of 8a1 as a tan solid: LCMS: m/z calcd for $C_{31}H_{37}ClN_3O_2^+$ (M+1)$^+$= 518.25; m/z obsvd=518.30.

The following compounds can be prepared analogously:

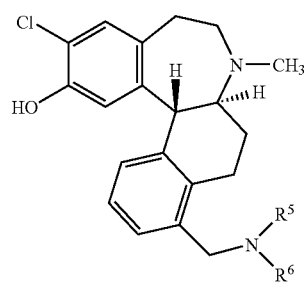

8a

| Cpd. # | R$^6$ | R$^5$ | Mol. Formula | Mol. Wt. | Obs. Mass (M + 1)$^+$ |
|---|---|---|---|---|---|
| 8a2 | (phenethyl) | (isopropyl-NH-C(O)-) | $C_{31}H_{36}ClN_3O_2$ | 518.1 | 518.0 |
| 8a3 | (4-fluorobenzyl) | (isopropyl-NH-C(O)-) | $C_{30}H_{33}ClFN_3O_2$ | 522.1 | 522.1 |

-continued
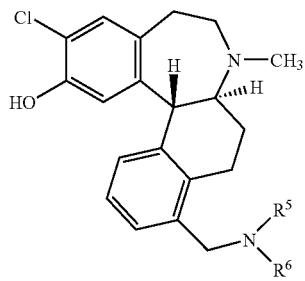
8a
| Cpd. # | R6 | R5 | Mol. Formula | Mol. Wt. | Obs. Mass (M + 1)+ |
|---|---|---|---|---|---|
| 8a4 | cyclopropylmethyl | isopropyl-NH-C(O)-C(CH3)2- | $C_{28}H_{36}ClN_3O_2$ | 482.1 | 482.3 |
| 8a5 | cyclopropylmethyl | PhNH-C(O)-C(CH3)2- | $C_{31}H_{34}ClN_3O_2$ | 516.1 | 516.3 |
| 8a6 | cyclohexylmethyl | PhNH-C(O)-C(CH3)2- | $C_{33}H_{38}ClN_3O_2$ | 544.1 | 544.3 |
| 8a7 | cyclopropyl | PhNH-C(O)-C(CH3)2- | $C_{30}H_{32}ClN_3O_2$ | 502.1 | 502.3 |
| 8a8 | n-butyl | PhNH-C(O)-C(CH3)2- | $C_{30}H_{34}ClN_3O_2$ | 504.1 | 504.3 |
| 8a9 | cyclopropyl | isopropyl-NH-C(O)-C(CH3)2- | $C_{27}H_{34}ClN_3O_2$ | 468.0 | 468.3 |
| 8a10 | benzyl | PhNH-C(O)-C(CH3)2- | $C_{33}H_{32}ClN_3O_2$ | 538.1 | 538.3 |

-continued
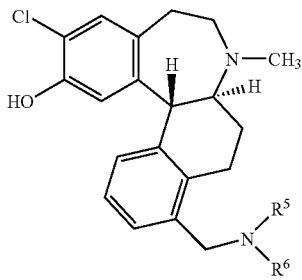
8a
| Cpd. # | R6 | R5 | Mol. Formula | Mol. Wt. | Obs. Mass (M + 1)+ |
|---|---|---|---|---|---|
| 8a11 | n-butyl | isopropyl-NH-C(=O)-C(CH3)2- | $C_{27}H_{36}ClN_3O_2$ | 470.1 | 470.3 |
| 8a12 | benzyl | Ph-NH-C(=O)-C(CH3)2- | $C_{34}H_{34}ClN_3O_2$ | 552.1 | 552.3 |
| 8a13 | cyclohexylmethyl | isopropyl-NH-C(=O)-C(CH3)2- | $C_{30}H_{40}ClN_3O_2$ | 510.1 | 510.3 |
The following compounds can be prepared analogously with regioisomeric starting materials:
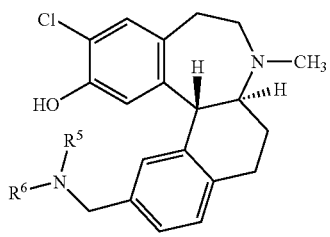
8b
| Cpd. # | R6 | R5 | Mol. Formula | Mol. Wt. | Obs. Mass (M + 1)+ |
|---|---|---|---|---|---|
| 8b1 | cyclopropylmethyl | isopropyl-NH-C(=O)-C(CH3)2- | $C_{28}H_{36}ClN_3O_2$ | 482.1 | 482.3 |

-continued

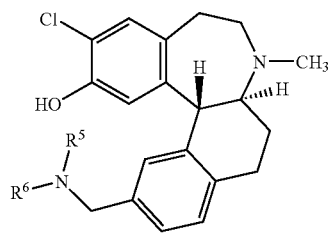

8b

| Cpd. # | R⁶ | R⁵ | Mol. Formula | Mol. Wt. | Obs. Mass (M + 1)⁺ |
|---|---|---|---|---|---|
| 8b2 | cyclopropylmethyl | -C(=O)NH-phenyl with gem-dimethyl | $C_{31}H_{34}ClN_3O_2$ | 516.1 | 516.3 |
| 8b3 | benzyl | -C(=O)NH-phenyl with gem-dimethyl | $C_{34}H_{34}ClN_3O_2$ | 552.1 | 552.3 |
| 8b4 | cyclopropyl | -C(=O)NH-phenyl with gem-dimethyl | $C_{30}H_{32}ClN_3O_2$ | 502.1 | 502.3 |
| 8b5 | benzyl | -C(=O)NH-iPr with gem-dimethyl | $C_{31}H_{36}ClN_3O_2$ | 518.1 | 518.3 |
| 8b6 | cyclopropylmethyl | -C(=O)NH-iPr with gem-dimethyl | $C_{27}H_{34}ClN_3O_2$ | 468.0 | 468.3 |
| 8b7 | cyclohexylmethyl | -C(=O)NH-phenyl with gem-dimethyl | $C_{33}H_{38}ClN_3O_2$ | 544.1 | 544.3 |
| 8b8 | phenyl | -C(=O)NH-phenyl with gem-dimethyl | $C_{33}H_{32}ClN_3O_2$ | 538.1 | 538.3 |
| 8b9 | n-butyl | -C(=O)NH-phenyl with gem-dimethyl | $C_{30}H_{34}ClN_3O_2$ | 504.1 | 504.3 |

-continued
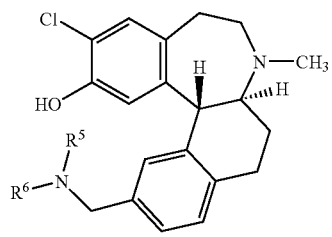
8b
| Cpd. # | R⁶ | R⁵ | Mol. Formula | Mol. Wt. | Obs. Mass (M + 1)⁺ |
|---|---|---|---|---|---|
| 8b10 | (n-butyl) | (isopropyl-NH-C(O)-C(CH$_3$)$_2$-) | $C_{27}H_{36}ClN_3O_2$ | 470.1 | 470.3 |
| 8b11 | (phenyl) | (isopropyl-NH-C(O)-C(CH$_3$)$_2$-) | $C_{30}H_{34}ClN_3O_2$ | 504.1 | 504.3 |
| 8b12 | (cyclohexyl) | (isopropyl-NH-C(O)-C(CH$_3$)$_2$-) | $C_{30}H_{40}ClN_3O_2$ | 510.1 | 510.3 |
The following compounds can be prepared analogously with regioisomeric starting materials:
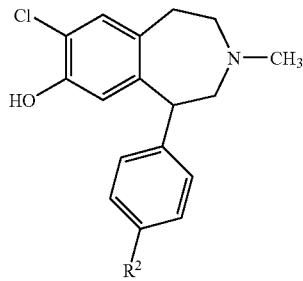
8c
| Cpd. # | R² | Mol. Formula | Mol. Wt. | Obs. Mass (M + 1)⁺ |
|---|---|---|---|---|
| 8c1 | (PhCH$_2$-NH-C(O)-N(CH$_2$Ph)-CH$_2$-) | $C_{33}H_{34}ClN_3O_2$ | 540.1 | 540 |

-continued
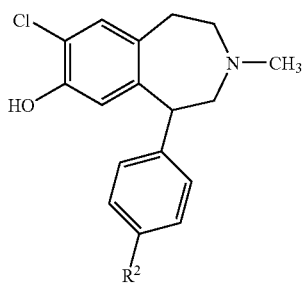
8c
| Cpd. # | R² | Mol. Formula | Mol. Wt. | Obs. Mass (M + 1)⁺ |
|---|---|---|---|---|
| 8c2 | MeO-C₆H₄-NH-C(O)-N(n-Pr)- | $C_{29}H_{34}ClN_3O_3$ | 508.1 | 508 |
| 8c3 | (R)-PhCH(CH₃)-NH-C(O)-N(n-Pr)- | $C_{30}H_{36}ClN_3O_2$ | 506.1 | 506 |
| 8c4 | 3-MeC₆H₄-NH-C(O)-N(n-Pr)- | $C_{29}H_{34}ClN_3O_2$ | 492.1 | 492 |
| 8c5 | MeNH-C(O)-N(n-Pr)- | $C_{23}H_{30}ClN_3O_2$ | 416.0 | 416 |
| 8c6 | Cyclohexyl-N(C(O)NHMe)- | $C_{26}H_{34}ClN_3O_2$ | 456.0 | 456 |
| 8c7 | Bn-N(C(O)NHMe)- | $C_{27}H_{30}ClN_3O_2$ | 464.0 | 464 |

-continued
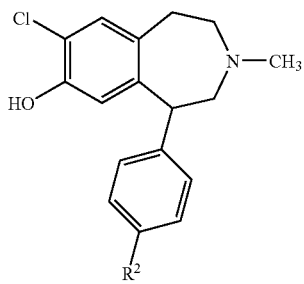
8c
| Cpd. # | R² | Mol. Formula | Mol. Wt. | Obs. Mass (M + 1)⁺ |
|---|---|---|---|---|
| 8c8 | H₃C-C₆H₄-CH₂-NH-C(O)-N(CH₂CH₂CH₃)- | $C_{30}H_{36}ClN_3O_2$ | 506.1 | 506 |
| 8c9 | cyclohexyl-N(-)-C(O)-NH-C₆H₄-OMe | $C_{32}H_{38}ClN_3O_3$ | 548.1 | 548 |
| 8c10 | (2-CH₃-C₆H₄)-NH-C(O)-N(n-Pr)- | $C_{29}H_{34}ClN_3O_2$ | 492.1 | 492 |
| 8c11 | H₃C-CH₂-NH-C(O)-N(CH₂C₆H₅)- | $C_{28}H_{32}ClN_3O_2$ | 478.0 | 478 |
| 8c12 | (CH₃)₂CH-NH-C(O)-N(CH₂C₆H₅)- | $C_{29}H_{34}ClN_3O_2$ | 492.1 | 492 |
| 8c13 | cyclohexyl-N(-)-C(O)-NH-CH₂CH₃ | $C_{27}H_{36}ClN_3O_2$ | 470.1 | 470 |

-continued
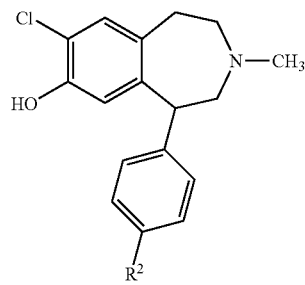
8c
| Cpd. # | R² | Mol. Formula | Mol. Wt. | Obs. Mass (M + 1)⁺ |
|---|---|---|---|---|
| 8c14 | | $C_{28}H_{38}ClN_3O_2$ | 484.1 | 484 |
| 8c15 | | $C_{32}H_{38}ClN_3O_2$ | 532.1 | 532 |
| 8c16 | | $C_{33}H_{40}ClN_3O_2$ | 546.2 | 546 |
| 8c17 | | $C_{32}H_{38}ClN_3O_2$ | 532.1 | 532 |
| 8c18 | | $C_{24}H_{32}ClN_3O_2$ | 430.0 | 430 |

-continued
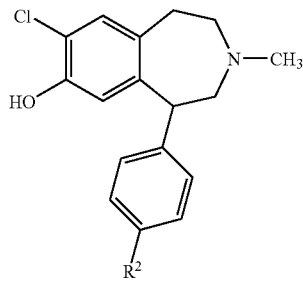
8c
| Cpd. # | R² | Mol. Formula | Mol. Wt. | Obs. Mass (M + 1)⁺ |
|---|---|---|---|---|
| 8c19 | 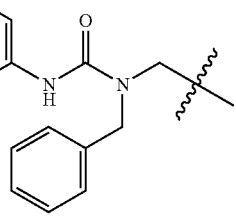 | $C_{33}H_{34}ClN_3O_3$ | 556.1 | 556 |
| 8c20 | 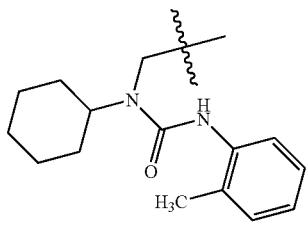 | $C_{32}H_{38}ClN_3O_2$ | 532.1 | 532 |
| 8c21 | 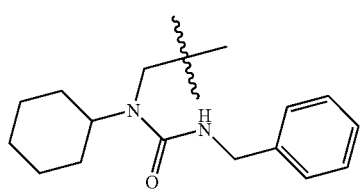 | $C_{32}H_{38}ClN_3O_2$ | 532.1 | 532 |
| 8c22 | 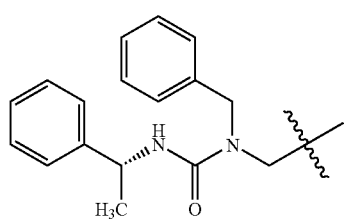 | $C_{34}H_{36}ClN_3O_2$ | 554.1 | 554 |
| 8c23 | 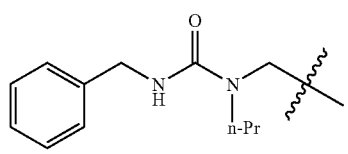 | $C_{29}H_{34}ClN_3O_2$ | 492.1 | 492 |

-continued
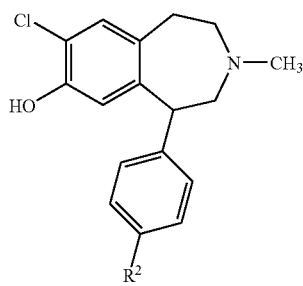
8c
| Cpd. # | R² | Mol. Formula | Mol. Wt. | Obs. Mass (M + 1)⁺ |
|---|---|---|---|---|
| 8c24 |  | $C_{33}H_{34}ClN_3O_2$ | 540.1 | 540 |
| 8c25 |  | $C_{34}H_{36}ClN_3O_2$ | 554.1 | 554 |
| 8c26 |  | $C_{33}H_{34}ClN_3O_2$ | 540.1 | 540 |
| 8c27 |  | $C_{25}H_{34}ClN_3O_2$ | 444.0 | 444 |
| 8c28 |  | $C_{31}H_{42}ClN_3O_2$ | 524.2 | 524 |
| 8c29 |  | $C_{28}H_{38}ClN_3O_2$ | 484.1 | 484 |

-continued
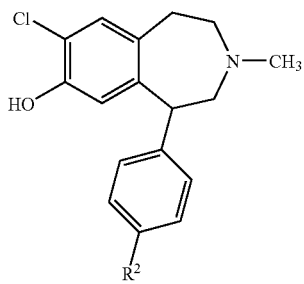
8c
| Cpd. # | R² | Mol. Formula | Mol. Wt. | Obs. Mass (M + 1)⁺ |
|---|---|---|---|---|
| 8c30 | | $C_{33}H_{40}ClN_3O_2$ | 546.2 | 546 |
| 8c31 | | $C_{25}H_{32}ClN_3O_2$ | 442.0 | 442 |
| 8c32 | | $C_{29}H_{32}ClN_3O_2$ | 490.0 | 490 |
| 8c33 | | $C_{28}H_{32}ClN_3O_2$ | 478 | 478 |
| 8c34 | | $C_{31}H_{36}ClN_3O_2$ | 518 | 518 |

Method 9

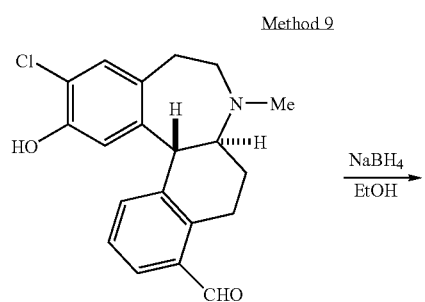

4a

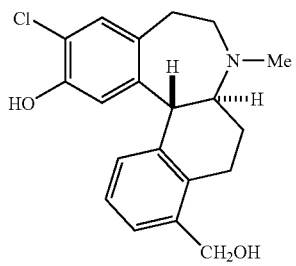

9

Compound 4a (0.025 g, 0.073 mmol) was dissolved in methanol and treated with NaBH$_4$ (10 mg, excess) at room temperature. The reaction mixture was stirred for 30 minutes and quenched by the addition of water. The mixture was extracted with dichloromethane and the combined organic layers were dried over sodium sulfate. The solvent was evaporated in vacuo and the product was isolated by preparative TLC using 15% methanol in dichloromethane as eluent to give 0.019 g of 9 as a foam. ES MS: calcd for $C_{20}H_{23}ClNO_2{}^+$ = 344.1; found=344.1 (M+1)$^+$

Method 10

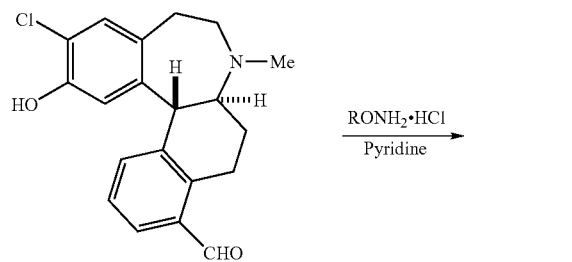

10a

Compound 4a (0.67 g, 1.96 mmol) was dissolved in 5 mL of pyridine and treated with hydroxylamine hydrochloride (0.2 g, 2.87 mmol). The mixture was heated at 70° C. for 4 hours. The solvent was removed in vacuo and the product was isolated by silica gel column chromatography eluting with 3-10% MeOH in dichloromethane. The oxime, 10a, was isolated in 90% yield as a solid. ES MS: m/z calcd for $C_{20}H_{22}ClN_2O_2{}^+$=357.1; found m/z=357.1 (M+1)$^+$.

The following compounds can be prepared by analogous methods:

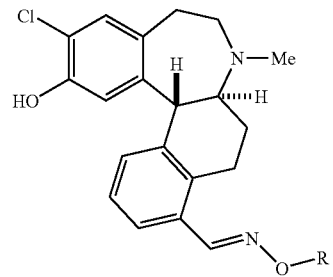

| Cpd. # | R$^4$ | Analytical data |
|---|---|---|
| 10b | —CH$_3$ | ES MS: calcd for $C_{21}H_{24}ClN_2O_2{}^+$ = 371.1; found = 371.1 (M + 1)$^+$ |
| 10c | —CH$_2$CH$_3$ | ES MS: calcd for $C_{22}H_{26}ClN_2O_2{}^+$ = 385.1; found = 385.1 (M + 1)$^+$ |
| 10d | —CH$_2$Ph | ES MS: calcd for $C_{27}H_{28}ClN_2O_2{}^+$ = 447.1; found = 447.1 (M + 1)$^+$ |
| 10e | —Ph | ES MS: calcd for $C_{26}H_{26}ClN_2O_2{}^+$ = 433.1; found = 433.1 (M + 1)$^+$ |

The following compound could be made analogously:

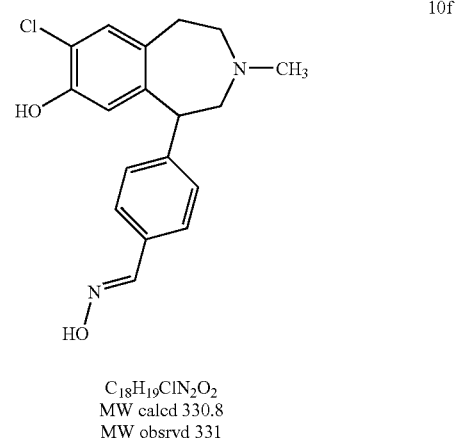

10f $C_{18}H_{19}ClN_2O_2$
MW calcd 330.8
MW obsrvd 331

Methods 11 and 12

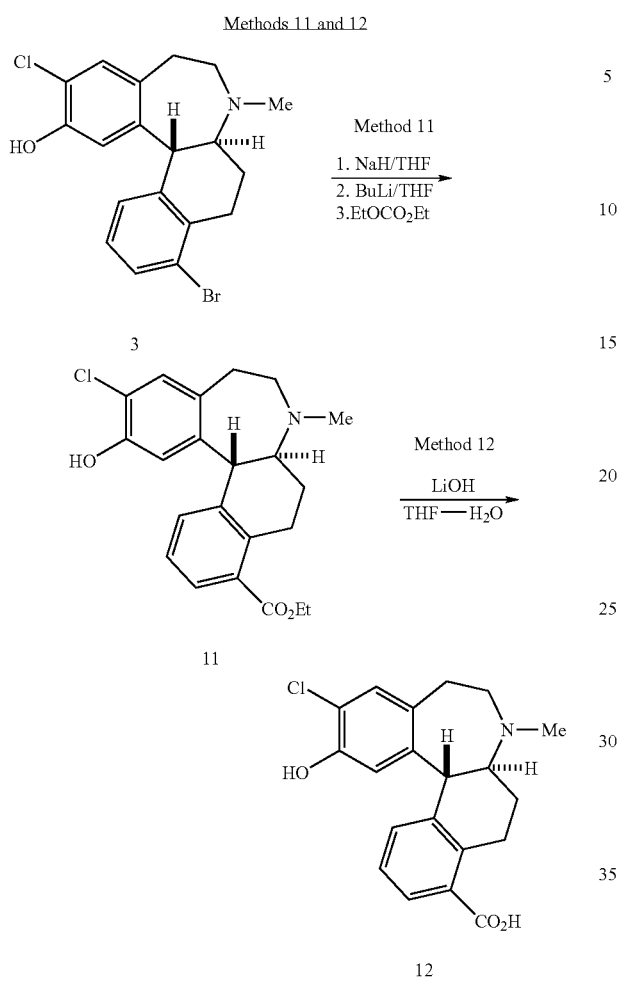

The following compound could be made analogously:

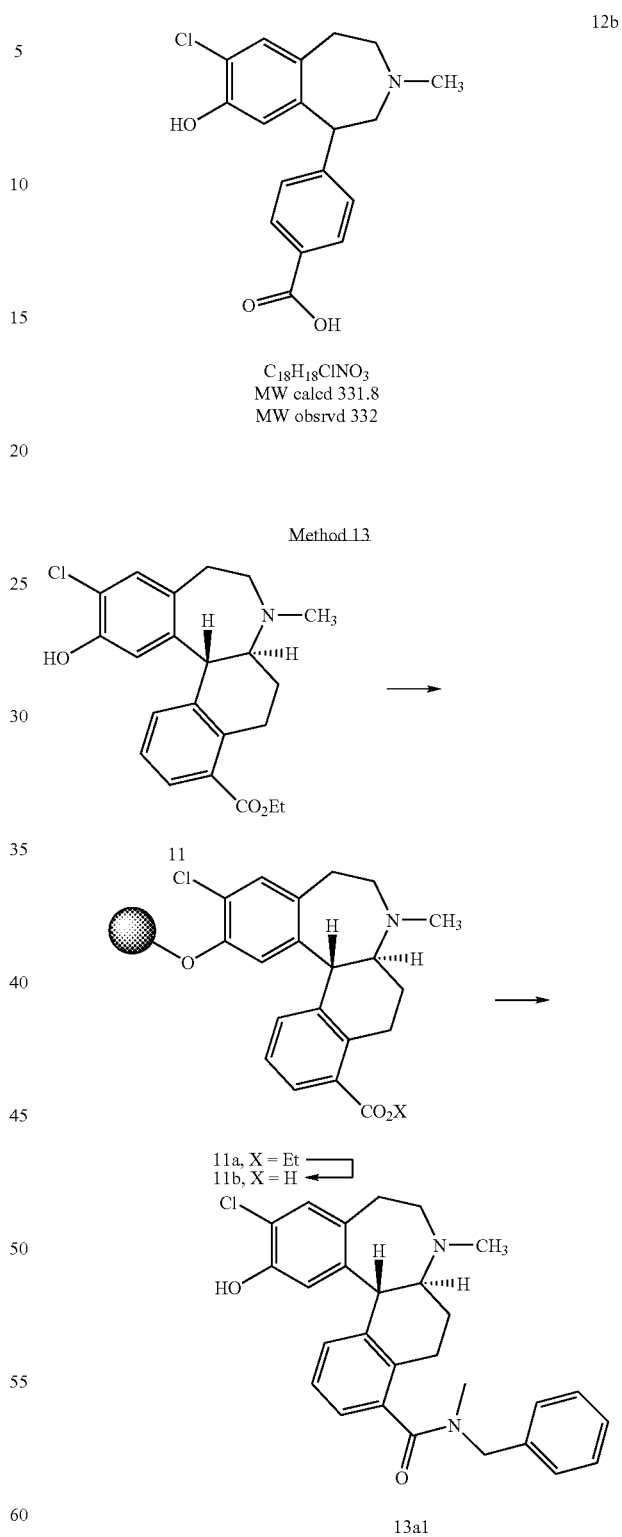

$C_{18}H_{18}ClNO_3$
MW calcd 331.8
MW obsrvd 332

Compound 3a (1.16 g, 2.95 mmol) was dissolved in 100 mL of THF and cooled to −78° C. under an atmosphere of nitrogen. Sodium hydride (65% in mineral oil, 0.2 g, 6 mmol) was added and stirred at that temperature for 30 minutes. n-BuLi (4.72 mL, 2.5M in hexanes, 4 eq) was added dropwise and stirred at −78° C. for 15 minutes. Diethylcarbonate (2 mL in 5 mL of THF) was added dropwise and the mixture was stirred for 30 minutes. The reaction was quenched by the addition of saturated aqueous NH$_4$Cl solution and extracted with dichloromethane. The organic layer was concentrated in vacuo and the crude ester residue used directly for the next step.

The crude ester 11 (1.0 g, 2.6 mmol) was dissolved in THF—H$_2$O (9:1, 100 mL) and treated with LiOH (0.5 g, 4.5 eq). The reaction mixture was heated at 70° C. for 2 hours. The solvent was removed in vacuo and the residue was redissolved in 25 mL of methanol. The mixture was neutralized with dilute aqueous hydrochloric acid. The solvent was removed in vacuo and the contents were directly charged onto a silica gel column. The product was isolated by gradient elution using 5% methanol progressing to 2N ammonia in methanol to give after concentration 0.7 g of the acid, 12, as a solid. ES MS: m/z calcd for $C_{20}H_{21}ClNO_3{}^+$=358.1; found m/z=358.1 (M+1)$^+$.

To a slurry of pre-swelled 2-chlorotrityl resin (2 eq, 1.0 g, 1.6 mmol/g) in 10 mL of dichloromethane was added 11 (1 eq) and diisopropylethylamine (DIEA) (8 eq). The resin was shaken overnight followed by sequential washings with 10% DIEA in methanol, dichloromethane, methanol, and THF.

The resin was then dried in vacuo. Resin 11a was hydrolyzed with 0.5 N tetrabutylammonium hydroxide in THF overnight followed by sequential washings with DMF, dichloromethane, THF and methanol to give resin-bound acid 11b.

To a slurry of pre-swelled resin-bound acid 11b in NMP (0.05 g, 0.64 mmol/g) was added HATU (5 eq) and HOAT (5 eq) and the mixture was shaken for 10 min before N-methylbenzylamine (5 eq) was added. The mixture was agitated for 3 h, the solution was drained, and the resin washed with NMP followed by a recharge of the reagents. The final mixture was shaken overnight followed by sequential washing with DMF, THF, dichloromethane and methanol. The resin was cleaved with 2% TFA in dichloromethane to give 0.084 g of the desired product 13a1. RP-LC MS: m/z calcd for $C_{28}H_{30}ClN_2O_2^+$=461.2; found m/z=461.3 (M+1)$^+$.

With the same method, the following compounds can also be synthesized.

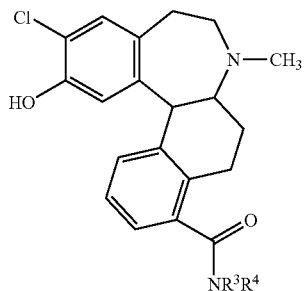

-continued
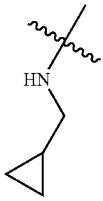
| Cpd. # | NR³R⁴ | Mol. Formula | Mol. Wt. | Obs. Mass (M + 1)⁺ |
|---|---|---|---|---|
| 13a9 | 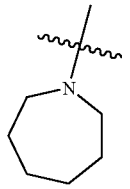 | $C_{24}H_{27}ClN_2O_2$ | 410.95 | 412.2 |
| 13a10 | 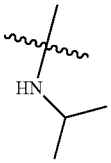 | $C_{26}H_{31}ClN_2O_2$ | 439.00 | 439.2 |
| 13a11 | 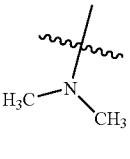 | $C_{23}H_{27}ClN_2O_2$ | 398.94 | 400.2 |
| 13a12 | 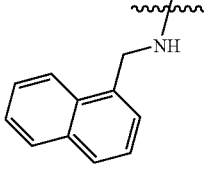 | $C_{22}H_{25}ClN_2O_2$ | 384.91 | 386.2 |
| 13a13 | 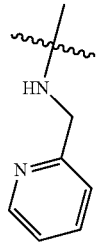 | $C_{31}H_{29}ClN_2O_2$ | 497.04 | 497.3 |
-continued
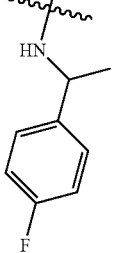
| Cpd. # | NR³R⁴ | Mol. Formula | Mol. Wt. | Obs. Mass (M + 1)⁺ |
|---|---|---|---|---|
| 13a14 | 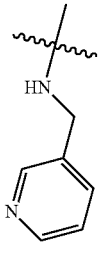 | $C_{26}H_{26}ClN_3O_2$ | 447.97 | 448.3 |
| 13a15 | 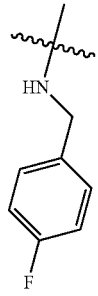 | $C_{28}H_{28}ClFN_2O_2$ | 479.00 | 479.3 |
| 13a16 | | $C_{26}H_{26}ClN_3O_2$ | 447.97 | 448.3 |
| 13a17 | | $C_{27}H_{26}ClFN_2O_2$ | 464.97 | 465.3 |

-continued
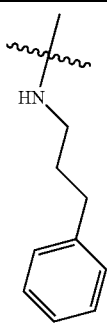
| Cpd. # | NR³R⁴ | Mol. Formula | Mol. Wt. | Obs. Mass (M + 1)⁺ |
|---|---|---|---|---|
| 13a18 | HN-CH₂CH₂CH₂-Ph | $C_{29}H_{31}ClN_2O_2$ | 475.04 | 475.3 |
| 13a19 | HN-CH₂-(4-pyridyl) | $C_{26}H_{26}ClN_3O_2$ | 447.97 | 448.3 |
| 13a20 | HN-CH₂CH₂-(2-pyridyl) | $C_{27}H_{28}ClN_3O_2$ | 462.00 | 462.3 |
-continued
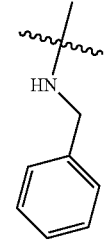
| Cpd. # | NR³R⁴ | Mol. Formula | Mol. Wt. | Obs. Mass (M + 1)⁺ |
|---|---|---|---|---|
| 13a21 | HN-CH₂-Ph | $C_{27}H_{27}ClN_2O_2$ | 446.98 | 447.3 |
| 13a22 | N(CH₃)-Ph | $C_{27}H_{27}ClN_2O_2$ | 446.98 | 447.2 |
| 13a23 | HN-Ph | $C_{26}H_{25}ClN_2O_2$ | 432.95 | 433.2 |
| 13a24 | HN-CH₃ | $C_{21}H_{23}ClN_2O_2$ | 370.88 | 371.2 |

Using the same method starting with compound 32 the following compounds can also be synthesized.
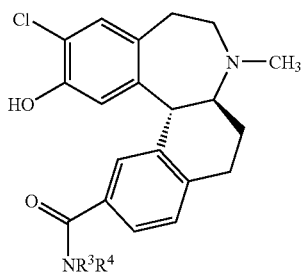
| Cpd. # | NR³R⁴ | Mol. Formula | Mol. Wt. | Obs. Mass (M + 1)⁺ |
|---|---|---|---|---|
| 13c1 | piperidinyl | $C_{25}H_{29}ClN_2O_2$ | 424.98 | 425.1 |
| 13c2 | tetrahydronaphthyl-NH | $C_{30}H_{31}ClN_2O_2$ | 487.05 | 487.1 |
| 13c3 | benzyl-NH | $C_{27}H_{27}ClN_2O_2$ | 446.98 | 447.1 |
| 13c4 | cyclopentyl-NH | $C_{25}H_{29}ClN_2O_2$ | 424.98 | 425.10 |
| 13c5 | 3-chlorophenethyl-NH | $C_{28}H_{28}Cl_2N_2O_2$ | 495.45 | 495.1 |

-continued
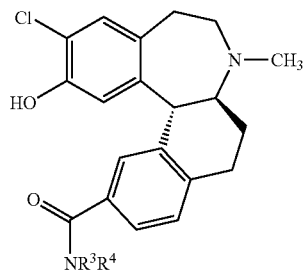
| Cpd. # | NR³R⁴ | Mol. Formula | Mol. Wt. | Obs. Mass (M + 1)⁺ |
|---|---|---|---|---|
| 13c6 | 2-chlorophenethylamino | $C_{28}H_{28}Cl_2N_2O_2$ | 495.45 | 495.1 |
| 13c7 | 4-phenylbutan-2-ylamino | $C_{30}H_{33}ClN_2O_2$ | 489.06 | 489.1 |
| 13c8 | 4-benzhydrylpiperazin-1-yl | $C_{37}H_{38}ClN_3O_2$ | 592.19 | 592.1 |
| 13c9 | cyclopropylmethylamino | $C_{24}H_{27}ClN_2O_2$ | 410.95 | 411.1 |
| 13c10 | thiophen-2-ylmethylamino | $C_{25}H_{25}ClN_2O_2S$ | 453.01 | 453.1 |
| 13c11 | sec-butylamino | $C_{24}H_{29}ClN_2O_2$ | 412.96 | 413.1 |

-continued
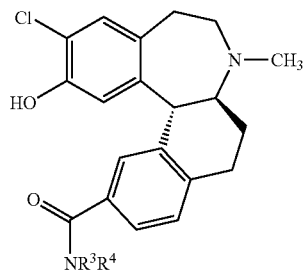
| Cpd. # | NR³R⁴ | Mol. Formula | Mol. Wt. | Obs. Mass (M + 1)⁺ |
|---|---|---|---|---|
| 13c12 | (tetrahydrofuran-2-ylmethyl)NH– | $C_{25}H_{29}ClN_2O_3$ | 440.97 | 441.1 |
| 13c13 | (2-phenylpropyl)NH– | $C_{29}H_{31}ClN_2O_2$ | 475.04 | 475.1 |
| 13c14 | (1-phenylethyl)NH– | $C_{28}H_{29}ClN_2O_2$ | 461.01 | 461.1 |
| 13c15 | cyclopropyl-NH– | $C_{23}H_{25}ClN_2O_2$ | 396.92 | 397.1 |
| 13c16 | (2-phenylethyl)NH– | $C_{28}H_{29}ClN_2O_2$ | 461.01 | 461.1 |
| 13c17 | (2-chlorobenzyl)NH– | $C_{27}H_{26}Cl_2N_2O_2$ | 481.43 | 481.1 |
| 13c18 | CH₃–NH– | $C_{21}H_{23}ClN_2O_2$ | 370.88 | 371.1 |

-continued
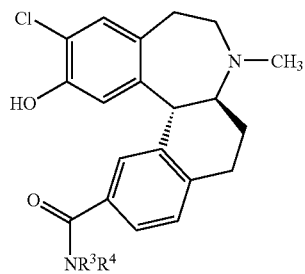
| Cpd. # | NR³R⁴ | Mol. Formula | Mol. Wt. | Obs. Mass (M + 1)⁺ |
|---|---|---|---|---|
| 13c19 | benzyl(methyl)amino | $C_{28}H_{29}ClN_2O_2$ | 461.01 | 461.1 |
| 13c20 | (1-phenylpropyl)amino | $C_{29}H_{31}ClN_2O_2$ | 475.04 | 475.1 |
| 13c21 | ethyl 4-aminopiperidine-1-carboxylate | $C_{28}H_{34}ClN_3O_4$ | 512.05 | 512.1 |
| 13c22 | (3-methylbutan-2-yl)amino | $C_{25}H_{31}ClN_2O_2$ | 426.99 | 427.1 |
| 13c23 | [1-(4-fluorophenyl)ethyl]amino | $C_{28}H_{28}ClFN_2O_2$ | 479.00 | 479.1 |

-continued
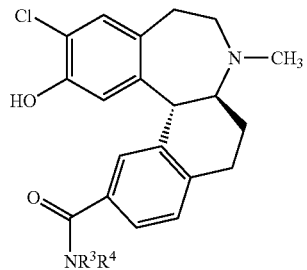
| Cpd. # | NR³R⁴ | Mol. Formula | Mol. Wt. | Obs. Mass (M + 1)⁺ |
|---|---|---|---|---|
| 13c24 | (1-benzylpiperidin-4-yl)amino | $C_{32}H_{36}ClN_3O_2$ | 530.12 | 530.1 |
| 13c25 | 4-acetyl-4-phenylpiperidin-1-yl | $C_{33}H_{35}ClN_2O_3$ | 543.11 | 543.1 |
| 13c26 | propylamino | $C_{23}H_{27}ClN_2O_2$ | 398.94 | 399.1 |
| 13c27 | 4-(pyridin-2-yl)piperazin-1-yl | $C_{29}H_{31}ClN_4O_2$ | 503.05 | 503.1 |
| 13c28 | morpholin-4-yl | $C_{24}H_{27}ClN_2O_3$ | 426.95 | 427.1 |

-continued
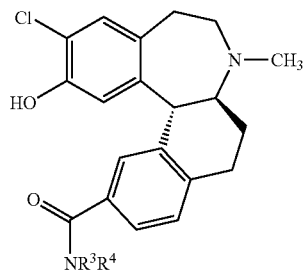
| Cpd. # | NR³R⁴ | Mol. Formula | Mol. Wt. | Obs. Mass (M + 1)⁺ |
|---|---|---|---|---|
| 13c29 | 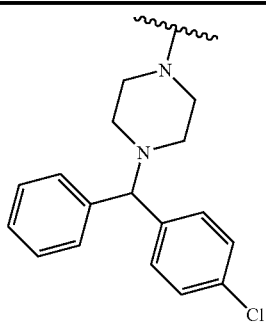 | $C_{37}H_{37}Cl_2N_3O_2$ | 626.63 | 626.2 |
| 13c30 | 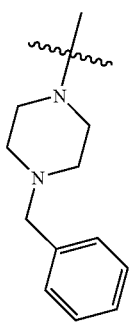 | $C_{31}H_{34}ClN_3O_2$ | 516.09 | 516.1 |
| 13c31 | 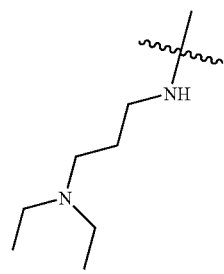 | $C_{27}H_{36}ClN_3O_2$ | 470.06 | 470.1 |
| 13c32 | 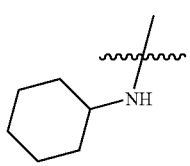 | $C_{26}H_{31}ClN_2O_2$ | 439.00 | 439.1 |

-continued
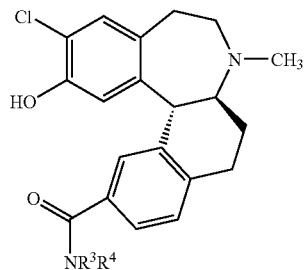
| Cpd. # | NR³R⁴ | Mol. Formula | Mol. Wt. | Obs. Mass (M + 1)⁺ |
|---|---|---|---|---|
| 13c33 | (2-((methylamino)methyl)-1-ethylpyrrolidine) | $C_{27}H_{34}ClN_3O_2$ | 468.04 | 468.1 |
| 13c34 | (dimethylamino) | $C_{22}H_{25}ClN_2O_2$ | 384.91 | 384.9 |
| 13c35 | (2,3-dihydro-1H-inden-5-ylamino) | $C_{29}H_{29}ClN_2O_2$ | 473.02 | 473.1 |
| 13c36 | (4-nitrobenzylamino) | $C_{27}H_{26}ClN_3O_4$ | 491.98 | 492.1 |
| 13c37 | (3-nitrobenzylamino) | $C_{27}H_{26}ClN_3O_4$ | 491.98 | 492.1 |

-continued
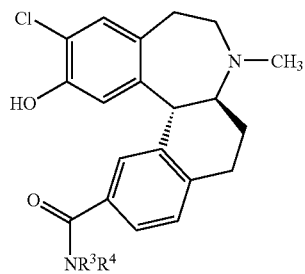
| Cpd. # | NR³R⁴ | Mol. Formula | Mol. Wt. | Obs. Mass (M + 1)⁺ |
|---|---|---|---|---|
| 13c38 | | $C_{32}H_{33}ClN_4O_3$ | 557.10 | 557.1 |
| 13c39 | | $C_{26}H_{26}ClN_3O_2$ | 447.97 | 448.1 |
| 13c40 | | $C_{27}H_{34}ClN_3O_2$ | 468.04 | 468.1 |
| 13c41 | | $C_{34}H_{33}ClN_2O_2$ | 537.11 | 537.1 |
| 13c42 | | $C_{28}H_{27}ClN_2O_4$ | 490.99 | 491.1 |

-continued
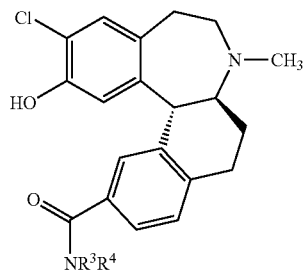
| Cpd. # | NR³R⁴ | Mol. Formula | Mol. Wt. | Obs. Mass (M + 1)⁺ |
|---|---|---|---|---|
| 13c43 | N-methylpiperazinyl | $C_{25}H_{30}ClN_3O_2$ | 439.99 | 440.1 |
| 13c44 | isopentylamino | $C_{25}H_{31}ClN_2O_2$ | 426.99 | 427.1 |
| 13c45 | 4-fluorobenzylamino | $C_{27}H_{26}ClFN_2O_2$ | 464.97 | 465.1 |
| 13c46 | 3-phenylpropylamino | $C_{29}H_{31}ClN_2O_2$ | 475.04 | 475.1 |
| 13c47 | 3,3-diphenylpropylamino | $C_{35}H_{35}ClN_2O_2$ | 551.13 | 551.1 |

-continued
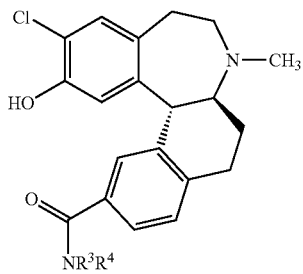
| Cpd. # | NR³R⁴ | Mol. Formula | Mol. Wt. | Obs. Mass (M + 1)⁺ |
|---|---|---|---|---|
| 13c48 | (1-naphth-2-yl-ethyl)amino | $C_{32}H_{31}ClN_2O_2$ | 511.07 | 511.1 |
| 13c49 | (indan-1-yl)amino | $C_{29}H_{29}ClN_2O_2$ | 473.02 | 473.1 |
| 13c50 | 1,2,3,4-tetrahydroisoquinolin-2-yl | $C_{29}H_{29}ClN_2O_2$ | 473.02 | 473.1 |
| 13c51 | (2-methylbenzyl)amino | $C_{28}H_{29}ClN_2O_2$ | 461.01 | 461.1 |
| 13c52 | (pyridin-3-ylmethyl)amino | $C_{26}H_{26}ClN_3O_2$ | 447.97 | 448.1 |

-continued
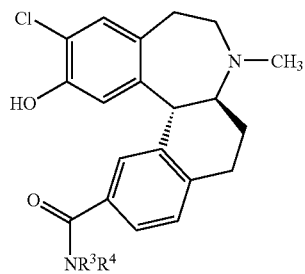
| Cpd. # | NR³R⁴ | Mol. Formula | Mol. Wt. | Obs. Mass (M + 1)⁺ |
|---|---|---|---|---|
| 13c53 |  | $C_{29}H_{31}ClN_2O_2$ | 475.04 | 475.1 |
| 13c54 |  | $C_{35}H_{35}ClN_2O_2$ | 551.13 | 551.1 |
| 13c55 |  | $C_{37}H_{36}ClF_2N_3O_2$ | 628.17 | 628.2 |
| 13c56 |  | $C_{27}H_{25}Cl_2FN_2O_2$ | 499.42 | 499.1 |
| 13c57 | 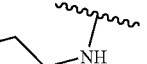 | $C_{27}H_{33}ClN_2O_2$ | 453.03 | 453.1 |

-continued
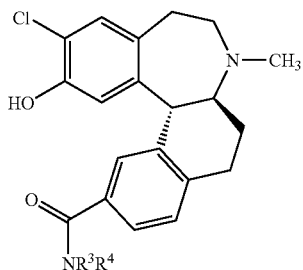
| Cpd. # | NR³R⁴ | Mol. Formula | Mol. Wt. | Obs. Mass (M + 1)⁺ |
|---|---|---|---|---|
| 13c58 | 3-(trifluoromethyl)benzyl-NH- | $C_{28}H_{26}ClF_3N_2O_2$ | 514.98 | 515.1 |
| 13c59 | furan-2-ylmethyl-NH- | $C_{25}H_{25}ClN_2O_3$ | 436.94 | 437.1 |
| 13c60 | 3-(pyrrolidin-1-yl)propyl-NH- | $C_{27}H_{34}ClN_3O_2$ | 468.04 | 468.1 |
| 13c61 | (4-chlorophenyl)(phenyl)methyl-NH- | $C_{33}H_{30}Cl_2N_2O_2$ | 557.53 | 557.1 |
| 13c62 | cycloheptyl-NH- | $C_{27}H_{33}ClN_2O_2$ | 453.03 | 453.1 |

-continued
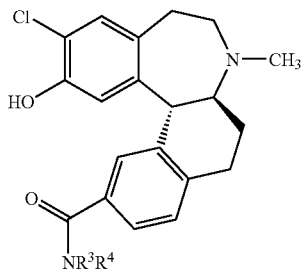
| Cpd. # | NR³R⁴ | Mol. Formula | Mol. Wt. | Obs. Mass (M + 1)⁺ |
|---|---|---|---|---|
| 13c63 | *4-(trifluoromethyl)benzyl-NH-* | $C_{28}H_{26}ClF_3N_2O_2$ | 514.98 | 515.1 |
| 13c64 | *3,4-dichlorobenzyl-NH-* | $C_{27}H_{25}Cl_3N_2O_2$ | 515.87 | 517.1 |
| 13c65 | *4-methoxyphenyl-NH-* | $C_{27}H_{27}ClN_2O_3$ | 462.98 | 463.1 |
| 13c66 | *naphthalen-1-ylmethyl-NH-* | $C_{31}H_{29}ClN_2O_2$ | 497.04 | 497.1 |
| 13c67 | *2-morpholinoethyl-NH-* | $C_{26}H_{32}ClN_3O_3$ | 470.02 | 470.1 |

-continued
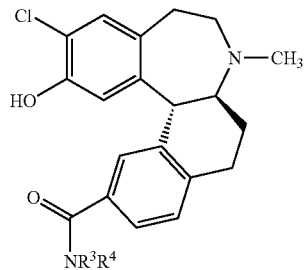
| Cpd. # | NR³R⁴ | Mol. Formula | Mol. Wt. | Obs. Mass (M + 1)⁺ |
|---|---|---|---|---|
| 13c68 | (2-pyridylethyl)NH- | $C_{27}H_{28}ClN_3O_2$ | 462.00 | 462.1 |
| 13c69 | (3-chlorobenzyl)NH- | $C_{27}H_{26}Cl_2N_2O_2$ | 481.43 | 481.1 |
Using the same method starting with compound 12b the following compounds can also be synthesized.
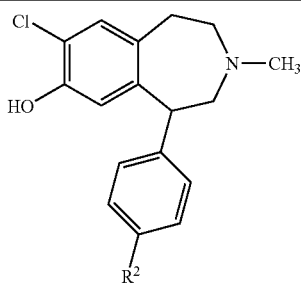
| Cpd. # | R² | Mol. Formula | Mol. Wt. | Obs. Mass (M + 1)⁺ |
|---|---|---|---|---|
| 13d1 | PhCH(CH₃)NHC(O)C(CH₃)₂- | $C_{26}H_{27}ClN_2O_2$ | 435.0 | 435 |
| 13d2 | PhCH₂NHC(O)C(CH₃)₂- | $C_{25}H_{25}ClN_2O_2$ | 420.9 | 421 |

-continued
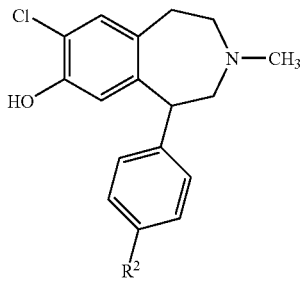
| Cpd. # | R² | Mol. Formula | Mol. Wt. | Obs. Mass (M + 1)⁺ |
|---|---|---|---|---|
| 13d3 | (4-methoxyphenyl)CH₂-C(=O)- | $C_{25}H_{25}ClN_2O_3$ | 436.9 | 437 |
| 13d4 | PhCH₂CH₂NH-C(=O)- | $C_{26}H_{27}ClN_2O_2$ | 435.0 | 435 |
| 13d5 | (4-Cl-C₆H₄)NH-C(=O)- | $C_{24}H_{22}Cl_2N_2O_2$ | 441.4 | 441 |
| 13d6 | (2-CH₃-C₆H₄)NH-C(=O)- | $C_{25}H_{25}ClN_2O_2$ | 420.9 | 421 |
| 13d7 | PhNH-C(=O)- | $C_{24}H_{23}ClN_2O_2$ | 406.9 | 407 |
| 13d8 | CH₃OCH₂CH₂NH-C(=O)- | $C_{21}H_{25}ClN_2O_3$ | 388.9 | 389 |
| 13d9 | cyclopropyl-CH₂-NH-C(=O)- | $C_{22}H_{25}ClN_2O_2$ | 384.9 | 385 |
| 13d10 | CH₃NH-C(=O)- | $C_{19}H_{21}ClN_2O_2$ | 344.8 | 345 |
| 13d11 | cyclobutyl-NH-C(=O)- | $C_{22}H_{25}ClN_2O_2$ | 384.9 | 385 |

-continued

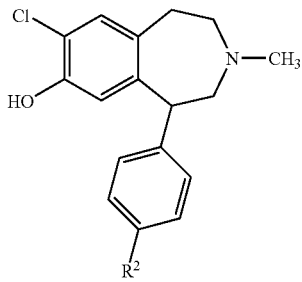

| Cpd. # | R² | Mol. Formula | Mol. Wt. | Obs. Mass (M + 1)⁺ |
| --- | --- | --- | --- | --- |
| 13d12 | cyclohexyl-NH-C(O)-C(CH₃)₂- | C₂₄H₂₉ClN₂O₂ | 413.0 | 413 |
| 13d13 | isobutyl-NH-C(O)-C(CH₃)₂- | C₂₂H₂₇ClN₂O₂ | 386.9 | 387 |
| 13d14 | isopropyl-NH-C(O)-C(CH₃)₂- | C₂₁H₂₅ClN₂O₂ | 372.9 | 373 |
| 13d15 | ethyl-NH-C(O)-C(CH₃)₂- | C₂₀H₂₃ClN₂O₂ | 358.9 | 359 |
| 13d16 | cyclopentyl-NH-C(O)-C(CH₃)₂- | C₂₃H₂₇ClN₂O₂ | 398.9 | 399 |
| 13d17 | n-propyl-NH-C(O)-C(CH₃)₂- | C₂₁H₂₅ClN₂O₂ | 372.9 | 373 |
| 13d18 | morpholinyl-C(O)-C(CH₃)₂- | C₂₂H₂₅ClN₂O₃ | 400.9 | 401 |
| 13d19 | piperidinyl-C(O)-C(CH₃)₂- | C₂₃H₂₇ClN₂O₂ | 398.9 | 399 |
| 13d20 | (CH₃)₂N-C(O)-C(CH₃)₂- | C₂₀H₂₃ClN₂O₂ | 358.9 | 359 |

Method 14

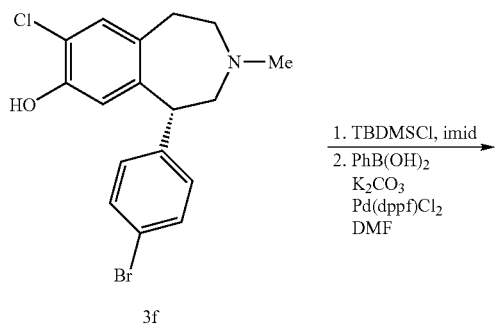

3f (1.2 g) was dissolved in 5 mL N-methylpyrrolidinone and 10 mL EtOAc followed by addition of imidazole (1.1 g, 5 eq) and t-BuMe$_2$SiCl (1.22 g, 2.5 eq). The mixture was stirred for 48 h. After washing with saturated NaHCO$_3$ and concentration, the resulting residue was purified by SiO$_2$ chromatography eluting with 100% dichloromethane progressing to MeOH:NH$_4$OH:dichloromethane=4:1:96) to provide 1.4 g the desired silylated intermediate: $^1$HNMR (CDCl$_3$) δ 0.00 (s, 6H) 0.90 (s, 9H) 2.38 (m, 1H) 2.40 (s, 3H) 2.70-3.10 (m, 5H) 4.20 (br s, 1H) 6.10 (s, 1H) 7.05 (d, 2H, J=8.3 Hz) 7.10 (s, 1H) 7.50 (d, 2H, J=8.3 Hz).

The TBDMS ether intermediate (50 mg) was mixed with phenylboronic acid (38 mg, 3 eq), K$_2$CO$_3$ (0.1 g, 7 eq), Pd(dppf)Cl$_2$ (7 mg, 0.08 eq) in 1 mL DMF. The mixture was then stirred at 70° C. for 12 h. Extraction with EtOAc and washing with saturated NaHCO$_3$ followed by flash chromatography (100% dichloromethane to MeOH:NH$_4$OH:dichloromethane=4:1:96) provided 30 mg of the desired biaryl product 14a: $^1$HNMR (CDCl$_3$) δ 2.38 (s, 3H) 2.30-2.40 (m, 1H) 2.70-2.90 (m, 3H) 3.00-3.10(m,2H) 4.22 (d, 1H, J=8.5 Hz) 6.40 (s, 1H) 7.10 (s, 1H) 7.20 (d, 2H, J=8.1 Hz) 7.35-7.60 (m, 7H).

The following products could be made using analogous techniques:

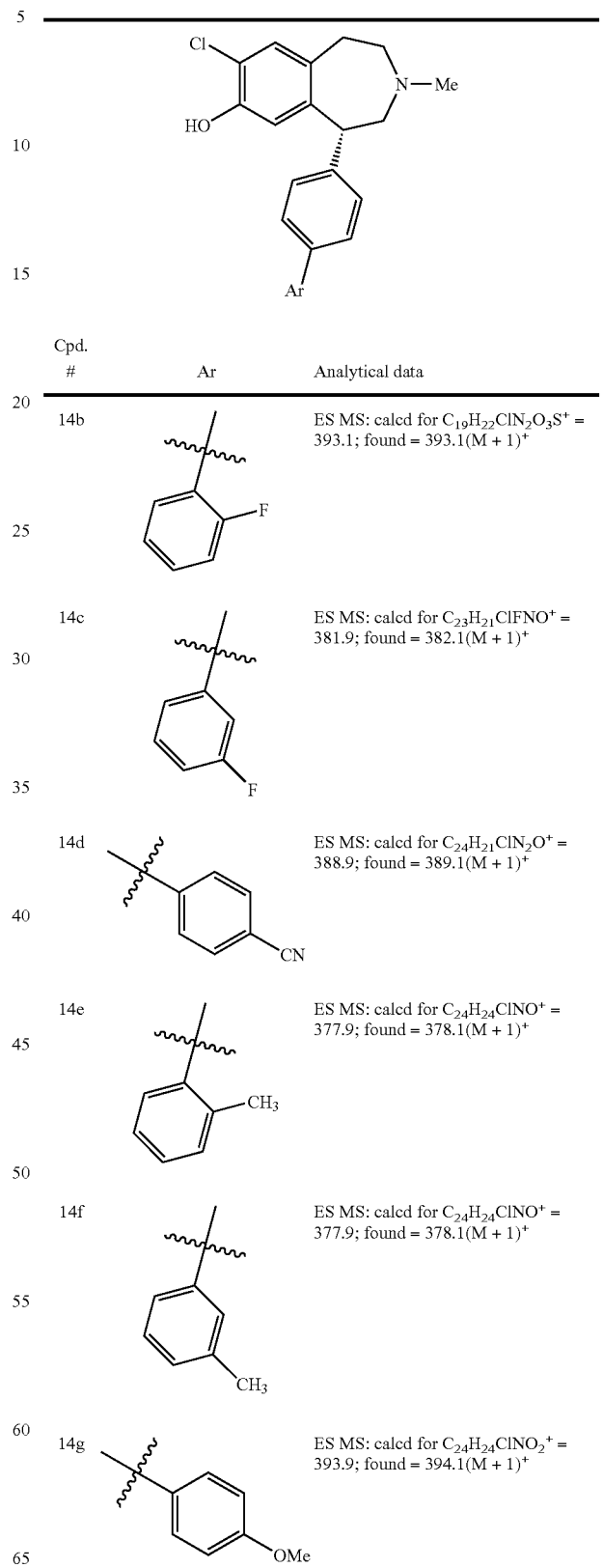

-continued

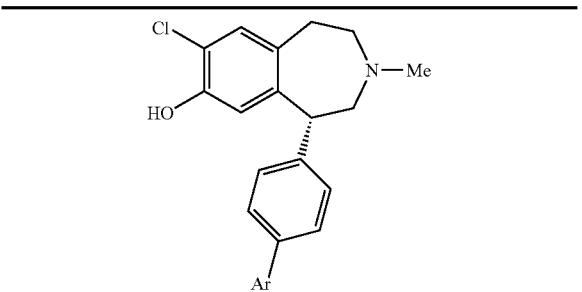

| Cpd. # | Ar | Analytical data |
|---|---|---|
| 14h | 2-thienyl | ES MS: calcd for $C_{21}H_{20}ClNOS^+$ = 369.9; found = 370.1(M + 1)$^+$ |
| 14i | 4-pyridyl | ES MS: calcd for $C_{22}H_{21}ClN_2O^+$ = 365.9; found = 365.1(M + 1)$^+$ |

The following products could be made using analogous techniques:

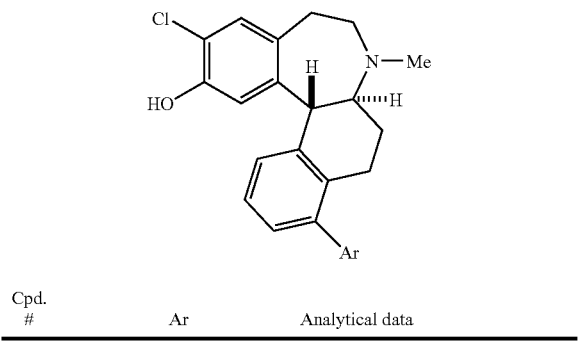

| Cpd. # | Ar | Analytical data |
|---|---|---|
| 14j | phenyl | ES MS: calcd for $C_{25}H_{25}ClNO^+$ = 390; found = 390(M + 1)$^+$ |
| 14k | 4-OMe-phenyl | ES MS: calcd for $C_{26}H_{27}ClNO_2^+$ = 420; found = 420(M + 1)$^+$ |
| 14l | 4-NMe$_2$-phenyl | ES MS: calcd for $C_{27}H_{30}ClN_2O^+$ = 433; found = 433(M + 1)$^+$ |

-continued

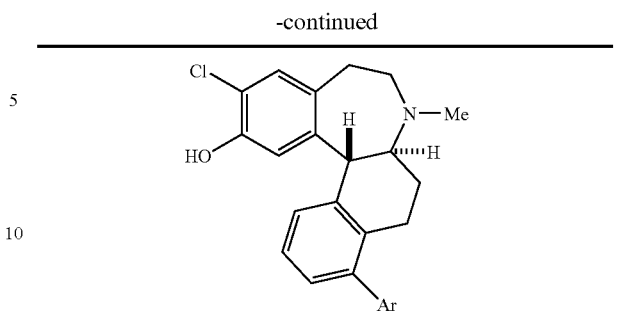

| Cpd. # | Ar | Analytical data |
|---|---|---|
| 14m | 5-indolyl | ES MS: calcd for $C_{27}H_{27}ClN_2O^+$ = 429; found = 429(M + 1)$^+$ |
| 14n | 3-F-phenyl | ES MS: calcd for $C_{25}H_{24}ClFNO^+$ = 408; found = 408(M + 1)$^+$ |
| 14o | 3,5-diF-phenyl | ES MS: calcd for $C_{25}H_{23}ClF_2NO^+$ = 426; found = 426(M + 1)$^+$ |
| 14p | 3-OCF$_3$-phenyl | ES MS: calcd for $C_{26}H_{24}ClF_3NO_2^+$ = 474; found = 474(M + 1)$^+$ |
| 14q | 4-CH$_2$OH-phenyl | ES MS: calcd for $C_{26}H_{27}ClNO_2^+$ = 420; found = 420(M + 1)$^+$ |
| 14r | 3-CN-phenyl | ES MS: calcd for $C_{26}H_{24}ClN_2O^+$ = 415; found = 415(M + 1)$^+$ |
| 14s | 3-NO$_2$-phenyl | ES MS: calcd for $C_{25}H_{24}ClN_2O_3^+$ = 435; found = 435(M + 1)$^+$ |
| 14t | 4-pyridyl | ES MS: calcd for $C_{24}H_{24}ClN_2O^+$ = 391; found = 391(M + 1)$^+$ |

-continued

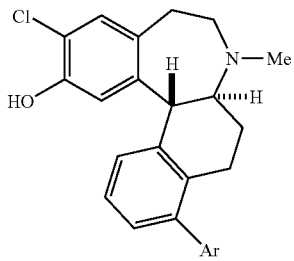

| Cpd. # | Ar | Analytical data |
|---|---|---|
| 14u | 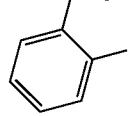 | ES MS: calcd for $C_{23}H_{23}ClNOS^+$ = 396; found = 396$(M + 1)^+$ |

The following example illustrates the analogous procedure for N-unsubstituted analogs:

3g

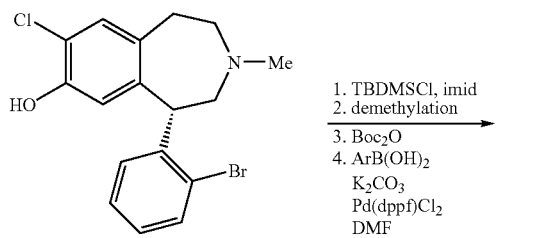

14v-14aa

The first protection step was carried out according to Method 14: $^1$HNMR (CDCl$_3$) δ 0.00 (s, 6H) 0.90 (s, 9H) 2.10 (m, 1H) 2.40 (s, 3H) 2.70 (m, 2H) 3.10 (m, 1H) 3.20 (m, 2H) 4.78 (d, 1H, J=8.8 Hz) 5.80 (s, 1H) 7.10 (s, 1H) 7.16-7.20 (m, 1H), 7.40 (m, 1H) 7.60 (dd, 2H, J=1.2, 8.0 Hz).

The TBS ether intermediate (1.5 g, 3.12 mmol, 1 eq) was treated with 1-chloroethyl chloroformate (1.78 g, 4 eq) in 15 mL dichloroethane at 90° C. for 3 h. The solvent was removed and 15 mL MeOH was introduced. The crude was stirred at 80° C. for 1 h. After cooling, the solvent was removed and dichloromethane was added. After washing with saturated NaHCO$_3$, 1.7 g of yellow solid was obtained. The solid was redissolved in 20 mL dichloromethane with Boc$_2$O (2.72 g, 4 eq) and Hünig's base (2.1 mL, 4 eq) and stirred for 2.5 h. After washing with saturated NaHCO$_3$, removal of solvent gave light brown syrup which was purified by chromatography over SiO$_2$ eluting with ethyl acetate:hexanes=5:95) to afford 1.4 g colorless syrup. $^1$HNMR (CDCl$_3$) δ 0.00 (s, 6H) 0.90 (s, 9H) 1.30 (s, 9H) 2.90 (m, 1H) 3.10 (m, 1H) 3.20 (m, 1H) 3.60 (m, 1H) 3.80 (m, 1H) 4.00 (m, 1H) 4.70 (br s, 1H) 6.10 (br s, 1H) 7.10-7.40(m, 4H) 7.60 (dd, 2H, J=1.2, 8.0 Hz).

The aryl coupling reaction was carried out according to the earlier description resulting in both N-Boc and O-TBS groups cleavage. The following compounds were prepared by this method:

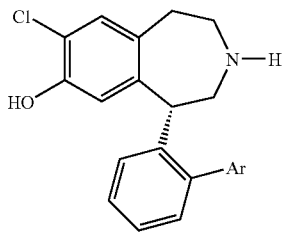

| Cpd. # | Ar | Analytical data |
|---|---|---|
| 14v | 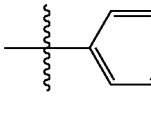 | ES MS: calcd for $C_{22}H_{19}ClFNO^+$ = 367.9; found = 368$(M + 1)^+$ |
| 14w | 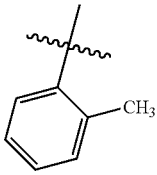 | ES MS: calcd for $C_{21}H_{19}ClN_2O^+$ = 350.9; found = 351$(M + 1)^+$ |
| 14x | 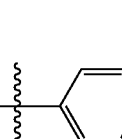 | ES MS: calcd for $C_{23}H_{22}ClNO^+$ = 363.9; found = 364$(M + 1)^+$ |
| 14y | 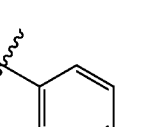 | ES MS: calcd for $C_{23}H_{22}ClNO^+$ = 363.9; found = 364$(M + 1)^+$ |
| 14z | 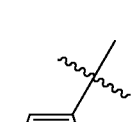 | ES MS: calcd for $C_{23}H_{22}ClNO_2^+$ = 379.9; found = 380$(M + 1)^+$ |
| 14aa | 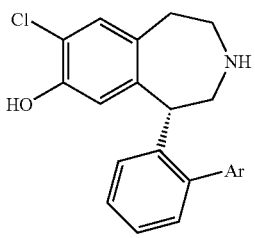 | ES MS: calcd for $C_{20}H_{18}ClNOS^+$ = 355.9; found = 356$(M + 1)^+$ |

Method 15

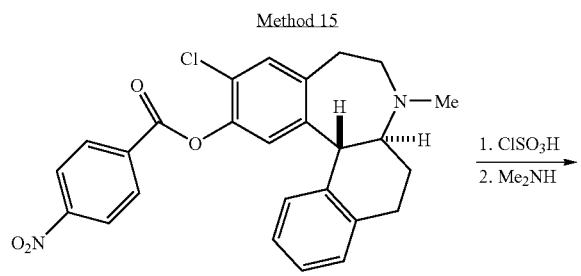

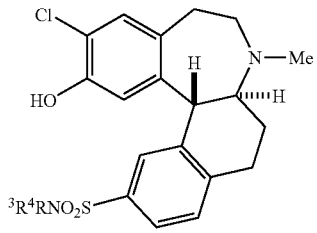

Compound 2a (0.1 g, 0.216 mmol) was dissolved in 2 mL of dichloromethane and cooled to 0° C. under nitrogen. Chlorosulfonic acid (neat, 1 mL, excess) was added dropwise over 10 minutes and stirred at 0° C. for 3 hours. The solvent was removed in vacuo to obtain an oil. The oil was redissolved in 2 mL of THF and treated with 1 mL of aqueous dimethylamine (40% solution) and stirred at room temperature overnight. The solvent was removed in vacuo and the product was purified by preparative TLC using 10% methanol in dichloromethane as eluent to give 0.048 g of 15a as a solid. ES MS: calcd for $C_{21}H_{26}ClN_2O_3S^+$=421.1; found=421.1 (M+1)$^+$.

The following compounds can be prepared by analogous chemistry:

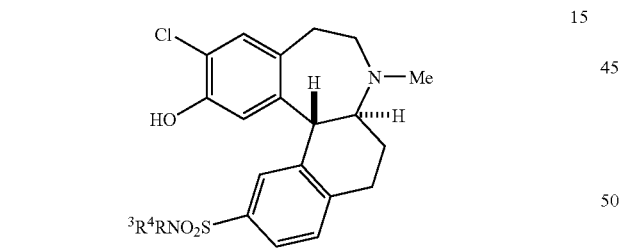

| Cpd. # | NR$^3$R$^4$ | Analytical data |
|---|---|---|
| 15b | —NH$_2$ | ES MS: calcd for $C_{19}H_{22}ClN_2O_3S^+$ = 393.1; found = 393.1(M + 1)$^+$ |
| 15c | —NHMe | ES MS: calcd for $C_{20}H_{24}ClN_2O_3S^+$ = 407.1; found = 407.1(M + 1)$^+$ |
| 15d | pyrrolidinyl | ES MS: calcd for $C_{23}H_{28}ClN_2O_3S^+$ = 447.1; found = 447.1(M + 1)$^+$ |
| 15e | piperidinyl | ES MS: calcd for $C_{24}H_{30}ClN_2O_3S^+$ = 462.1; found = 462.1(M + 1)$^+$ |
| 15f | N-methylpiperazinyl | ES MS: calcd for $C_{24}H_{31}ClN_3O_3S^+$ = 477.1; found = 477.1(M + 1)$^+$ |
| 15g | morpholinyl | ES MS: calcd for $C_{23}H_{28}ClN_2O_4S^+$ = 463.1; found = 463.1(M + 1)$^+$ |
| 15h | NHPh | ES MS: calcd for $C_{25}H_{26}ClN_2O_3S^+$ = 470.1; found = 470.1(M + 1)$^+$ |
| 15i | NH-(4-MePh) | ES MS: calcd for $C_{26}H_{28}ClN_2O_3S^+$ = 484.1; found = 484.1(M + 1)$^+$ |
| 15j | NH-(4-ClPh) | ES MS: calcd for $C_{26}H_{28}Cl_2N_2O_3S^+$ = 504.1; found = 504.1(M + 1)$^+$ |
| 15k | NH-(4-MeOPh) | ES MS: calcd for $C_{26}H_{28}ClN_2O_4S^+$ = 500.1; found = 500.1(M + 1)$^+$ |
| 15l | NHCH$_2$Ph | ES MS: calcd for $C_{26}H_{28}ClN_2O_3S^+$ = 484.1; found = 484.1(M + 1)$^+$ |
| 15m | NHCH$_2$-(4-MePh) | ES MS: calcd for $C_{27}H_{30}ClN_2O_3S^+$ = 498.1; found = 498.1(M + 1)$^+$ |
| 15n | NHCH$_2$-(4-BrPh) | ES MS: calcd for $C_{26}H_{27}BrClN_2O_3S^+$ = 562.1; found = 562.1(M + 1)$^+$ |

-continued

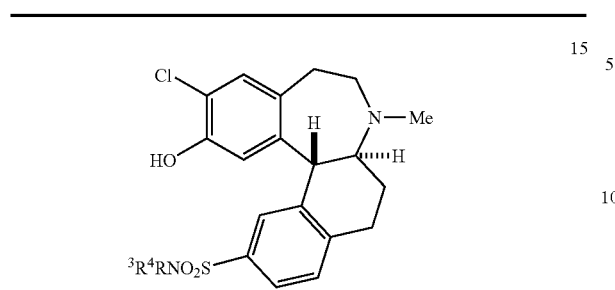

| Cpd. # | NR³R⁴ | Analytical data |
|---|---|---|
| 15o | (furfurylmethylamine structure) | ES MS: calcd for $C_{24}H_{26}ClN_2O_4S^+$ = 473.1; found = 473.1(M + 1)⁺ |
| 15p | (thienylmethylamine structure) | ES MS: calcd for $C_{24}H_{26}ClN_2O_3S_2^+$ = 490.1; found = 490.1(M + 1)⁺ |

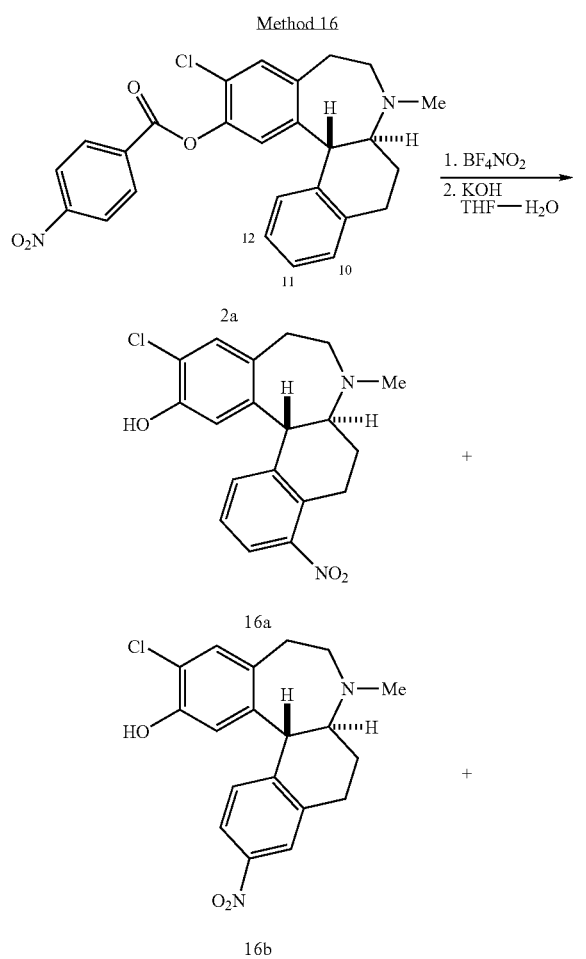

-continued (structure 16c)

Compound 2a (2.0 g, 4.32 mmol) was dissolved in 30 mL of acetonitrile, treated with BF₄NO₂ (1.6 g, 3 eq) at room temperature and stirred for 3 hours. The reaction was quenched by the addition of water and neutralized with saturated aqueous NaHCO₃ solution. The mixture was extracted with dichloromethane and dried over sodium sulfate. The solvent was removed in vacuo and the crude material was used as such for the next step. The crude mixture was redissolved in 40 mL of THF:H₂O (3:1,) and treated with LiOH (1 g in 40 mL water) and stirred at room temperature for 3 hours. The reaction mixture was neutralized with acetic acid and extracted with dichloromethane. The solvent was removed in vacuo and passed through a short pad of silica gel to remove the base line material. The products were isolated by HPLC using a silica gel column and eluting with 95% ethyl acetate/hexane containing 0.25% triethylamine.

16a (C10 isomer): 0.15 g, 10%. ES MS: m/z calcd for $C_{19}H_{20}ClN_2O_3^+$=359.1; found m/z=359.1 (M+1)⁺

16b (C11 isomer): 0.22 g, 14%. ES MS: m/z calcd for $C_{19}H_{20}ClN_2O_3^+$=359.1; found m/z=359.1 (M+1)⁺

16c (C12 isomer): 0.50 g, 32%. ES MS: m/z calcd for $C_{19}H_{20}ClN_2O_3^+$=359.1; found m/z=359.1 (M+1)⁺

Method 17.1

(structure 16c)

→ SnCl₂·2H₂O / EtOAc →

(structure 17c)

Compound 16c (0.05 g, 0.139 mmol) was dissolved in 10 mL of ethanol and 0.04 g of SnCl₂.2H₂O (0.156 mmol) was added. Acetic acid (3 drops) was added and the resulting mixture was heated under reflux for 2 hours. Water was added and the mixture was extracted with dichloromethane. The extract was dried over sodium sulfate and evaporated in vacuo. The product was isolated by preparative TLC using 5% MeOH in dichloromethane as eluent to give 0.03 g of aniline 17c. ES MS: m/z calcd for $C_{19}H_{22}ClN_2O^+$=329.1; found m/z=329.1 $(M+1)^+$.

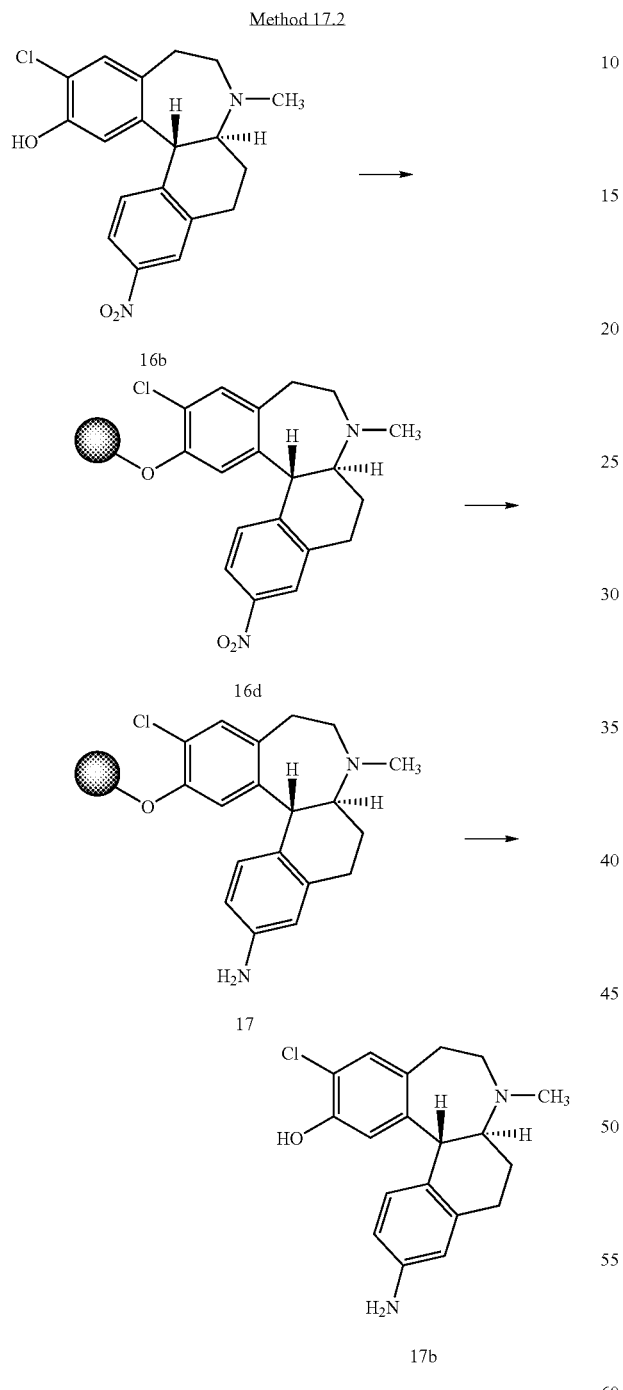

To a cartridge containing 1.84 g of Wang resin (1.0 mmol/g, 1 eq) pre-swelled in THF was added nitro compound 16b (1 eq) and triphenylphospine (2 eq) in 20 ml of THF followed by the addition of azodicarbonyldipiperidine (2 eq) in 10 ml of dichloromethane. After the mixture was agitated overnight, acetic acid (2 eq) was added and the final mixture was shaken for 2 more hours. The resin was sequentially washed with dichloromethane, THF and methanol, and dried in vacuo to give resin-bound 16d.

To the resin 16d suspended in DMF was added diisopropylethylamine (6 eq) and $SnCl_2.2H_2O$ (20 eq) under nitrogen. The mixture was agitated overnight followed by sequential washing with $H_2O$, EDTA (0.05M), DMF, dichloromethane, THF, and methanol. The product was cleaved from the resin (0.043 g) using 30% trifluoroacetic acid in dichloromethane to give 0.01 g of aniline 17b. ES MS: m/z calcd for $C_{19}H_{22}ClN_2O^+$=329.1; found m/z=329.1 $(M+1)^+$.

The C10 aniline isomer 17a can also be prepared by this method starting with nitro derivative 16a: 17a (C12 isomer): ES MS: m/z calcd for $C_{19}H_{22}ClN_2O^+$=329.1; found m/z=329.1 $(M+1)^+$.

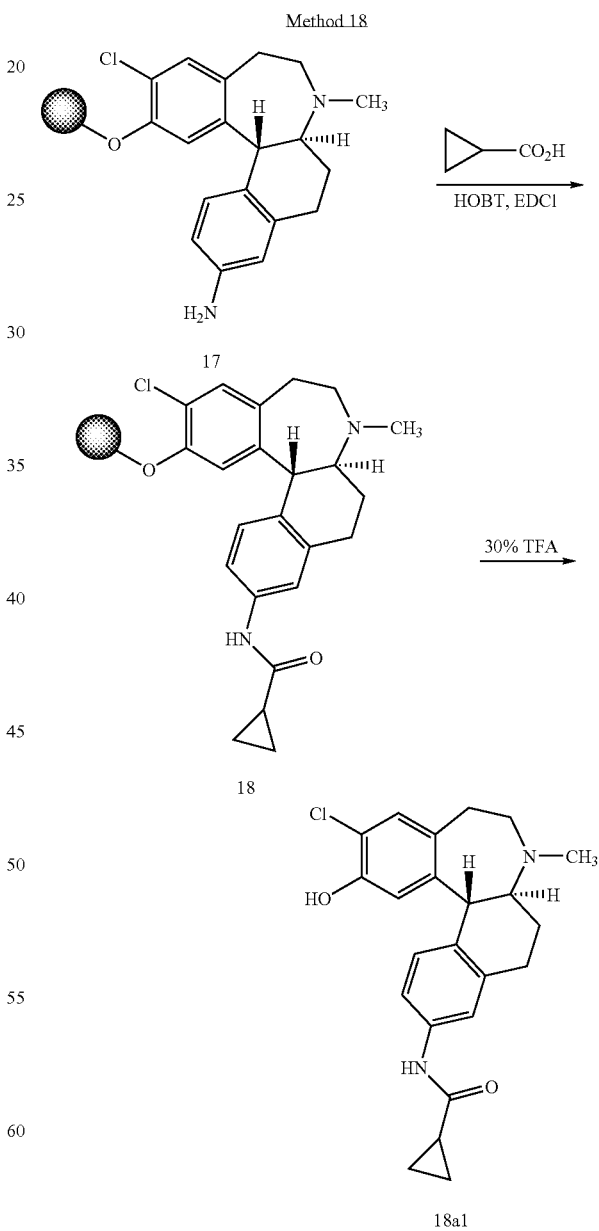

To 0.03 g of the resin-bound amine 17 (0.69 mmol/g) pre-swelled in DMF was added a solution of cyclopropane carboxylic acid (5 eq), HOBT (5 eq) and EDCl (5 eq) in DMF.

The mixture was agitated overnight and the resin washed with DMF, THF, dichloromethane and methanol. Cleavage with 30% trifluoroacetic acid in dichloromethane and formation of the HCl salt generated 0.0102 g of compound 18a1: RP-LC MS: m/z calcd for $C_{23}H_{26}ClN_2O_2{}^+=397.1$; found m/z=397.1 $(M+1)^+$.

The following compounds can be synthesized by the same method:

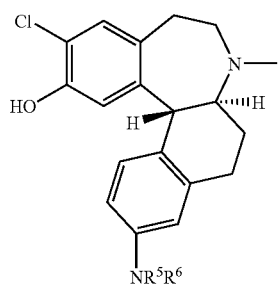

18a wherein $R^6$ is hydrogen:

| Cpd. # | $R^5$ | Mol. Formula | Mol. Wt. | Obs. Mass $(M + 1)^+$ |
|---|---|---|---|---|
| 18a2 | | $C_{24}H_{23}ClN_2O_2S$ | 438.98 | 439.1 |
| 18a3 | | $C_{24}H_{23}ClN_2O_3$ | 422.92 | 423.1 |
| 18a4 | | $C_{21}H_{23}ClN_2O_2$ | 370.88 | 371.1 |
| 18a5 | | $C_{27}H_{33}ClN_2O_2$ | 453.03 | 453.1 |
| 18a6 | | $C_{25}H_{29}ClN_2O_2$ | 424.98 | 425.1 |
| 18a7 | | $C_{24}H_{29}ClN_2O_2$ | 412.96 | 413.1 |
| 18a8 | | $C_{24}H_{27}ClN_2O_2$ | 410.95 | 411.1 |
| 18a9 | | $C_{24}H_{27}ClN_2O_3$ | 426.95 | 427.1 |
| 18a10 | | $C_{27}H_{27}ClN_2O_2$ | 446.98 | 447.1 |
| 18a11 | | $C_{25}H_{24}ClN_3O_2$ | 433.94 | 434.1 |
| 18a12 | | $C_{26}H_{25}ClN_2O_2$ | 432.95 | 433.1 |

-continued

| Cpd. # | R⁵ | Mol. Formula | Mol. Wt. | Obs. Mass (M + 1)⁺ |
|---|---|---|---|---|
| 18a13 | 4-methoxybenzoyl | $C_{27}H_{27}ClN_2O_3$ | 462.98 | 463.1 |
| 18a14 | 2-methoxybenzoyl | $C_{27}H_{27}ClN_2O_3$ | 462.98 | 463.1 |
| 18a15 | 1-naphthoyl | $C_{30}H_{27}ClN_2O_2$ | 483.02 | 483.1 |
| 18a16 | 2-methylbenzoyl | $C_{27}H_{27}ClN_2O_2$ | 446.98 | 447.1 |
| 18a17 | 3,4-dichlorobenzoyl | $C_{26}H_{23}Cl_3N_2O_2$ | 501.84 | 503.1 |
| 18a18 | 4-chlorobenzoyl | $C_{26}H_{24}Cl_2N_2O_2$ | 467.40 | 467.1 |

-continued

| Cpd. # | R⁵ | Mol. Formula | Mol. Wt. | Obs. Mass (M + 1)⁺ |
|---|---|---|---|---|
| 18a19 | isonicotinoyl | $C_{25}H_{24}ClN_3O_2$ | 433.94 | 434.1 |
| 18a20 | 2-naphthoyl | $C_{30}H_{27}ClN_2O_2$ | 483.02 | 483.1 |
| 18a21 | 4-(trifluoromethyl)benzoyl | $C_{27}H_{24}ClF_3N_2O_2$ | 500.95 | 501.1 |
| 18a22 | 5-methylisoxazole-3-carbonyl | $C_{24}H_{24}ClN_3O_3$ | 437.93 | 438.1 |
| 18a23 | picolinoyl | $C_{25}H_{24}ClN_3O_2$ | 433.94 | 434.1 |
| 18a24 | biphenyl-4-carbonyl | $C_{32}H_{29}ClN_2O_2$ | 509.05 | 509.1 |

The following compounds can also be prepared using this method starting with the regioisomeric resin bound amines 17:

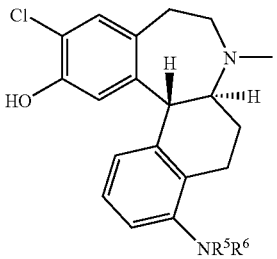
18b wherein $R^6$ is hydrogen:

| Cpd. # | $R^5$ | Mol. Formula | Mol. Wt. | Obs. Mass (M + 1)+ |
|---|---|---|---|---|
| 18b1 | (3,4-dichlorobenzoyl) | $C_{26}H_{23}Cl_3N_2O_2$ | 501.84 | 502.1 |
| 18b2 | (2-thienylcarbonyl) | $C_{24}H_{23}ClN_2O_2S$ | 438.98 | 439.1 |
| 18b3 | (2-furoyl) | $C_{24}H_{23}ClN_2O_3$ | 422.92 | 423.1 |
| 18b4 | (acetyl) | $C_{21}H_{23}ClN_2O_2$ | 370.88 | 371.1 |
| 18b5 | (cyclohexylacetyl) | $C_{27}H_{33}ClN_2O_2$ | 453.03 | 453.1 |
| 18b6 | (cyclopropylcarbonyl) | $C_{23}H_{25}ClN_2O_2$ | 396.92 | 397.1 |
| 18b7 | (cyclopentylcarbonyl) | $C_{25}H_{29}ClN_2O_2$ | 424.98 | 425.1 |
| 18b8 | (cyclopropylacetyl) | $C_{24}H_{27}ClN_2O_2$ | 410.95 | 411.1 |
| 18b9 | (tetrahydrofuran-2-ylcarbonyl) | $C_{24}H_{27}ClN_2O_3$ | 426.95 | 427.1 |
| 18b10 | (phenylacetyl) | $C_{27}H_{27}ClN_2O_2$ | 446.98 | 447.1 |
| 18b11 | (pyridin-3-ylcarbonyl) | $C_{25}H_{24}ClN_3O_2$ | 433.94 | 434.1 |
| 18b12 | (isobutylcarbonyl) | $C_{24}H_{29}ClN_2O_2$ | 412.96 | 413.1 |

-continued

| Cpd. # | R⁵ | Mol. Formula | Mol. Wt. | Obs. Mass (M + 1)⁺ |
|---|---|---|---|---|
| 18b13 | (benzoyl) | $C_{26}H_{25}ClN_2O_2$ | 432.95 | 433.1 |
| 18b14 | (4-methoxybenzoyl) | $C_{27}H_{27}ClN_2O_3$ | 462.98 | 463.1 |
| 18b15 | (1-naphthoyl) | $C_{30}H_{27}ClN_2O_2$ | 483.02 | 483.1 |
| 18b16 | (2-methylbenzoyl) | $C_{27}H_{27}ClN_2O_2$ | 446.98 | 447.1 |
| 18b17 | (4-chlorobenzoyl) | $C_{26}H_{24}Cl_2N_2O_2$ | 467.40 | 468.1 |
| 18b18 | (isonicotinoyl) | $C_{25}H_{24}ClN_3O_2$ | 433.94 | 434.1 |
| 18b19 | (2-naphthoyl) | $C_{30}H_{27}ClN_2O_2$ | 483.02 | 483.1 |
| 18b20 | (4-trifluoromethylbenzoyl) | $C_{27}H_{24}ClF_3N_2O_2$ | 500.95 | 501.1 |
| 18b21 | (5-methylisoxazole-3-carbonyl) | $C_{24}H_{24}ClN_3O_3$ | 437.93 | 438.1 |
| 18b22 | (picolinoyl) | $C_{25}H_{24}ClN_3O_2$ | 433.94 | 434.1 |
| 18b23 | (biphenyl-4-carbonyl) | $C_{32}H_{29}ClN_2O_2$ | 509.05 | 509.1 |
| 18b24 | (2-methoxybenzoyl) | $C_{27}H_{27}ClN_2O_3$ | 462.98 | 463.1 |

The following compounds can also be prepared using this method starting with the regioisomeric resin bound amine 17:

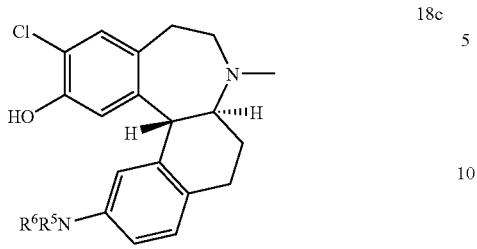

18c wherein $R^6$ is hydrogen:

| Cpd. # | $R^5$ | Mol. Formula | Mol. Wt. | Obs. Mass $(M+1)^+$ |
|---|---|---|---|---|
| 18c1 | phenyl ketone | $C_{26}H_{25}ClN_2O_2$ | 432.95 | 433.1 |
| 18c2 | 4-nitrophenyl ketone | $C_{26}H_{24}ClN_3O_4$ | 477.95 | 478.1 |
| 18c3 | 3,5-bis(trifluoromethyl)phenyl ketone | $C_{28}H_{23}ClF_6N_2O_2$ | 568.95 | 569.1 |
| 18c4 | 4-methoxyphenyl ketone | $C_{27}H_{27}ClN_2O_3$ | 462.98 | 463.1 |
| 18c5 | 2-methoxyphenyl ketone | $C_{27}H_{27}ClN_2O_3$ | 462.98 | 463.1 |
| 18c6 | 3-(trifluoromethyl)phenyl ketone | $C_{27}H_{24}ClF_3N_2O_2$ | 500.95 | 501.1 |

-continued

| Cpd. # | R⁵ | Mol. Formula | Mol. Wt. | Obs. Mass (M + 1)⁺ |
|---|---|---|---|---|
| 18c7 | naphthalen-1-yl-C(O)- | $C_{30}H_{27}ClN_2O_2$ | 483.02 | 483.1 |
| 18c8 | 2-methylphenyl-C(O)- | $C_{27}H_{27}ClN_2O_2$ | 446.98 | 447.1 |
| 18c9 | 3,4-dichlorophenyl-C(O)- | $C_{26}H_{23}Cl_3N_2O_2$ | 501.84 | 503.1 |
| 18c10 | thiophen-2-yl-C(O)- | $C_{24}H_{23}ClN_2O_2S$ | 438.98 | 439.1 |
| 18c11 | 4-chlorophenyl-C(O)- | $C_{26}H_{24}Cl_2N_2O_2$ | 467.40 | 467.1 |
| 18c12 | pyridin-4-yl-C(O)- | $C_{25}H_{24}ClN_3O_2$ | 433.94 | 434.1 |
| 18c13 | naphthalen-2-yl-C(O)- | $C_{30}H_{27}ClN_2O_2$ | 483.02 | 483.1 |
| 18c14 | 4-(trifluoromethyl)phenyl-C(O)- | $C_{27}H_{24}ClF_3N_2O_2$ | 500.95 | 501.1 |

-continued

| Cpd. # | R⁵ | Mol. Formula | Mol. Wt. | Obs. Mass (M + 1)⁺ |
|---|---|---|---|---|
| 18c15 | 3,4,5-trimethoxybenzoyl | $C_{29}H_{31}ClN_2O_5$ | 523.03 | 523.1 |
| 18c16 | 5-methylisoxazole-3-carbonyl | $C_{24}H_{24}ClN_3O_3$ | 437.93 | 438.1 |
| 18c17 | 2-fluoro-4-(trifluoromethyl)benzoyl | $C_{27}H_{23}ClF_4N_2O_2$ | 518.94 | 519.1 |
| 18c18 | pyridine-2-carbonyl | $C_{25}H_{24}ClN_3O_2$ | 433.94 | 434.1 |
| 18c19 | 6-(trifluoromethyl)pyridine-3-carbonyl | $C_{26}H_{23}ClF_3N_3O_2$ | 501.94 | 502.1 |
| 18c20 | biphenyl-4-carbonyl | $C_{32}H_{29}ClN_2O_2$ | 509.05 | 509.1 |
| 18c21 | furan-2-carbonyl | $C_{24}H_{23}ClN_2O_3$ | 422.92 | 423.1 |
| 18c22 | acetyl | $C_{21}H_{23}ClN_2O_2$ | 370.88 | 371.1 |

-continued

| Cpd. # | R⁵ | Mol. Formula | Mol. Wt. | Obs. Mass (M + 1)⁺ |
|---|---|---|---|---|
| 18c23 | 4-(dimethylamino)benzoyl | $C_{28}H_{30}ClN_3O_2$ | 476.02 | 476.1 |
| 18c24 | 3-cyclohexylpropanoyl | $C_{28}H_{35}ClN_2O_2$ | 467.06 | 467.1 |
| 18c25 | 4-chloro-2-fluorobenzoyl | $C_{26}H_{23}Cl_2FN_2O_2$ | 485.39 | 485.1 |
| 18c26 | isoquinoline-1-carbonyl | $C_{29}H_{26}ClN_3O_2$ | 484.00 | 484.1 |
| 18c27 | pyrazine-2-carbonyl | $C_{24}H_{23}ClN_4O_2$ | 434.93 | 435.1 |
| 18c28 | trans-2-phenylcyclopropanecarbonyl | $C_{29}H_{29}ClN_2O_2$ | 473.02 | 473.1 |
| 18c29 | 4-cyanobenzoyl | $C_{27}H_{24}ClN_3O_2$ | 457.96 | 458.1 |
| 18c30 | 2,3-dihydrobenzo[b][1,4]dioxine-2-carbonyl | $C_{28}H_{27}ClN_2O_4$ | 490.99 | 491.1 |

-continued
| Cpd. # | R⁵ | Mol. Formula | Mol. Wt. | Obs. Mass (M + 1)⁺ |
|---|---|---|---|---|
| 18c31 | 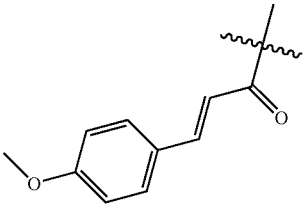 | $C_{29}H_{29}ClN_2O_3$ | 489.02 | 489.1 |
| 18c32 | 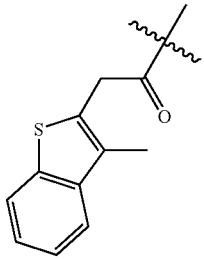 | $C_{30}H_{29}ClN_2O_2S$ | 517.10 | 517.1 |
| 18c33 | 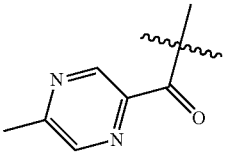 | $C_{25}H_{25}ClN_4O_2$ | 448.96 | 449.1 |
| 18c34 | 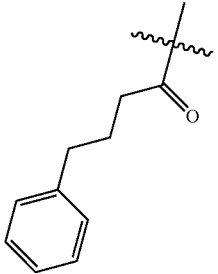 | $C_{29}H_{31}ClN_2O_2$ | 475.04 | 475.1 |
| 18c35 | 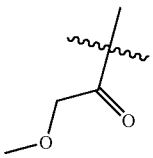 | $C_{22}H_{25}ClN_2O_3$ | 400.91 | 401.1 |
| 18c36 | 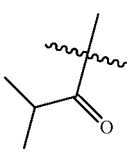 | $C_{23}H_{27}ClN_2O_2$ | 398.94 | 399.1 |
| 18c37 | 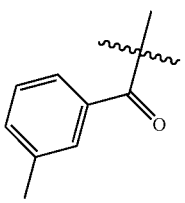 | $C_{27}H_{27}ClN_2O_2$ | 446.98 | 447.1 |

-continued
| Cpd. # | R⁵ | Mol. Formula | Mol. Wt. | Obs. Mass (M + 1)⁺ |
|---|---|---|---|---|
| 18c38 | 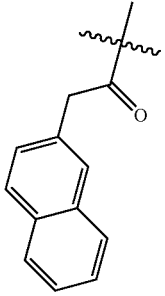 | $C_{31}H_{29}ClN_2O_2$ | 497.04 | 497.1 |
Method 19
The following compounds can be synthesized using similar chemistry starting with the regioisomeric resin-bound aniline 17.
wherein R⁶ is hydrogen:
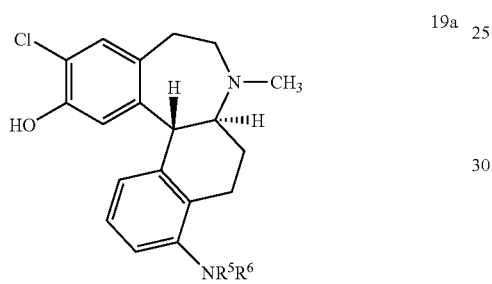
19a
| Cpd. # | R⁵ | Mol. Formula | Mol. Wt. | Obs. Mass (M + 1)⁺ |
|---|---|---|---|---|
| 19a1 | 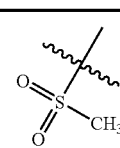 | $C_{20}H_{23}ClN_2O_3S$ | 406.9 | 408.1 |
| 19a2 | 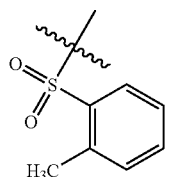 | $C_{26}H_{27}ClN_2O_3S$ | 483.0 | 484.1 |
| 19a3 | 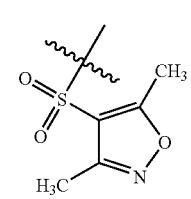 | $C_{24}H_{26}ClN_3O_4S$ | 488.0 | 489.1 |

-continued

| Cpd. # | R⁵ | Mol. Formula | Mol. Wt. | Obs. Mass (M + 1)⁺ |
|---|---|---|---|---|
| 19a4 | phenylsulfonyl | $C_{25}H_{25}ClN_2O_3S$ | 469.0 | 470.1 |
| 19a5 | ethylsulfonyl | $C_{21}H_{25}ClN_2O_3S$ | 421.0 | 422.1 |
| 19a6 | 4-fluorophenylsulfonyl | $C_{25}H_{24}ClFN_2O_3S$ | 487.0 | 488.1 |
| 19a7 | 4-methylphenylsulfonyl | $C_{26}H_{27}ClN_2O_3S$ | 483.0 | 484.1 |
| 19a8 | 4-acetamidophenylsulfonyl | $C_{27}H_{28}ClN_3O_4S$ | 526.1 | 436.1 |
| 19a9 | 2-chlorophenylsulfonyl | $C_{25}H_{24}Cl_2N_2O_3S$ | 503.5 | 505.1 |
| 19a10 | 2,3-dichlorophenylsulfonyl | $C_{25}H_{23}Cl_3N_2O_3S$ | 537.9 | 539.1 |
| 19a11 | 2,6-dichlorophenylsulfonyl | $C_{25}H_{23}Cl_3N_2O_3S$ | 537.9 | 539.1 |

-continued

| Cpd. # | R⁵ | Mol. Formula | Mol. Wt. | Obs. Mass (M + 1)⁺ |
|---|---|---|---|---|
| 19a12 | 2,4-dichlorophenylsulfonyl | $C_{25}H_{23}Cl_3N_2O_3S$ | 537.9 | 539.1 |
| 19a13 | 4-methoxyphenylsulfonyl | $C_{26}H_{27}ClN_2O_4S$ | 499.0 | 500.1 |
| 19a14 | 1-naphthylsulfonyl | $C_{29}H_{27}ClN_2O_3S$ | 519.1 | 520.1 |
| 19a15 | 2-(1-naphthyl)ethylsulfonyl | $C_{31}H_{31}ClN_2O_3S$ | 547.1 | 548.1 |
| 19a16 | 1-methylimidazol-4-ylsulfonyl | $C_{23}H_{25}ClN_4O_3S$ | 473.0 | 474.1 |
| 19a17 | 5-chloro-1,3-dimethylpyrazol-4-ylsulfonyl | $C_{24}H_{26}Cl_2N_4O_3S$ | 521.5 | 523.1 |
| 19a18 | propylsulfonyl | $C_{22}H_{27}ClN_2O_3S$ | 435.0 | 435.1 |

-continued

| Cpd. # | R⁵ | Mol. Formula | Mol. Wt. | Obs. Mass (M + 1)⁺ |
|---|---|---|---|---|
| 19a19 | isopropyl sulfonyl | $C_{22}H_{27}ClN_2O_3S$ | 435.0 | 436.1 |
| 19a20 | benzyl sulfonyl | $C_{26}H_{27}ClN_2O_3S$ | 483.0 | 484.1 |
| 19a21 | 5-chlorothiophene-2-sulfonyl | $C_{23}H_{22}Cl_2N_2O_3S_2$ | 509.5 | 511.1 |
| 19a22 | 3-cyanophenyl sulfonyl | $C_{26}H_{24}ClN_3O_3S$ | 494.0 | 495.1 |
| 19a23 | 4-chlorophenyl sulfonyl | $C_{25}H_{24}Cl_2N_2O_3S$ | 503.5 | 505.1 |
| 19a24 | 3,4-dichlorophenyl sulfonyl | $C_{25}H_{23}Cl_3N_2O_3S$ | 537.9 | 539.1 |
| 19a25 | 2,5-dichlorophenyl sulfonyl | $C_{25}H_{23}Cl_3N_2O_3S$ | 537.9 | 539.1 |

-continued

| Cpd. # | R⁵ | Mol. Formula | Mol. Wt. | Obs. Mass (M + 1)⁺ |
|---|---|---|---|---|
| 19a26 | 2-fluorophenylsulfonyl | $C_{25}H_{24}ClFN_2O_3S$ | 487.0 | 488.1 |
| 19a27 | naphthalen-2-ylsulfonyl | $C_{29}H_{27}ClN_2O_3S$ | 519.1 | 520.1 |
| 19a28 | 4-(trifluoromethyl)phenyl methylsulfonyl | $C_{26}H_{24}ClF_3N_2O_3S$ | 537.0 | 538.1 |
| 19a29 | 3-(trifluoromethyl)phenyl methylsulfonyl | $C_{26}H_{24}ClF_3N_2O_3S$ | 537.0 | 538.1 |
| 19a30 | benzo[c][1,2,5]oxadiazol-4-yl methylsulfonyl | $C_{25}H_{23}ClN_4O_4S$ | 511.0 | 512.1 |
| 19a31 | thiophen-2-ylmethylsulfonyl | $C_{23}H_{23}ClN_2O_3S_2$ | 475.0 | 476.1 |
| 19a32 | N,N-dimethylsulfamoyl | $C_{21}H_{26}ClN_3O_3S$ | 436 | 436.1 |

-continued
| Cpd. # | R⁵ | Mol. Formula | Mol. Wt. | Obs. Mass (M + 1)⁺ |
|---|---|---|---|---|
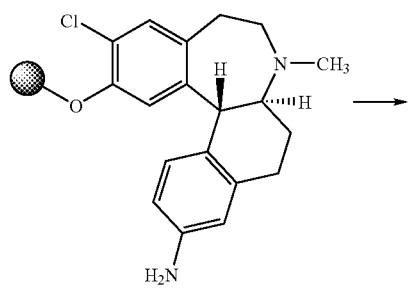
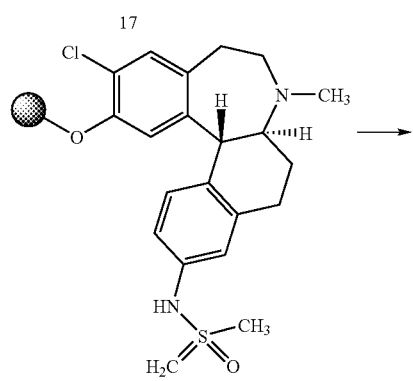
17
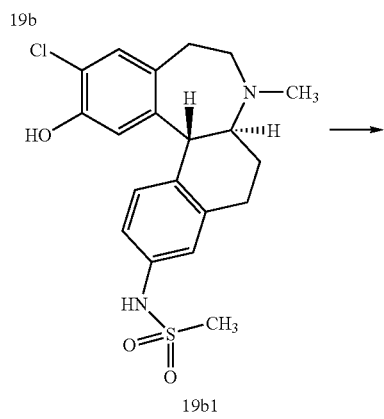
19b
19b1

To 0.03 g of the resin-bound aniline 17 (0.69 mmol/g) pre-swelled in pyridine was added 5 eq of methanesulfonyl-chloride. The mixture was agitated overnight and the resin 19b was washed with DMF, THF, dichloromethane and methanol. The product was cleaved from the resin with 30% TFA in dichloromethane to give compound 19b1. RP-LC MS: m/z calcd for $C_{20}H_{24}ClN_{20}O_3S^+$=407.1; found m/z=407.1 $(M+1)^+$.

The following compounds can be synthesized using related chemistry.

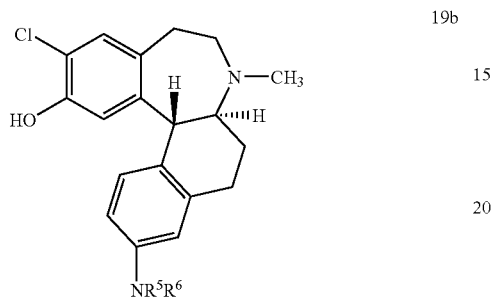

19b wherein $R^6$ is hydrogen:

| Cpd. # | $R^5$ | Mol. Formula | Mol. Wt. | Obs. Mass $(M + 1)^+$ |
|---|---|---|---|---|
| 19b2 | phenylsulfonyl | $C_{25}H_{25}ClN_2O_3S$ | 469.0 | 469.1 |
| 19b3 | 2-methylphenylsulfonyl | $C_{26}H_{27}ClN_2O_3S$ | 483.0 | 483.1 |
| 19b4 | 3,5-dimethylisoxazol-4-ylsulfonyl | $C_{24}H_{26}ClN_3O_4S$ | 488.0 | 488.1 |
| 19b5 | ethylsulfonyl | $C_{21}H_{25}ClN_2O_3S$ | 421.0 | 421.1 |
| 19b6 | 4-fluorophenylsulfonyl | $C_{25}H_{24}ClFN_2O_3S$ | 487.0 | 487.1 |

-continued

| Cpd. # | R⁵ | Mol. Formula | Mol. Wt. | Obs. Mass (M + 1)⁺ |
|---|---|---|---|---|
| 19b7 | 4-methylphenylsulfonyl | $C_{26}H_{27}ClN_2O_3S$ | 483.0 | 483.1 |
| 19b8 | 4-acetamidophenylsulfonyl | $C_{27}H_{28}ClN_3O_4S$ | 526.1 | 526.1 |
| 19b9 | 2-chlorophenylsulfonyl | $C_{25}H_{24}Cl_2N_2O_3S$ | 503.5 | 503.1 |
| 19b10 | 5-chlorothiophen-2-ylsulfonyl | $C_{23}H_{22}Cl_2N_2O_3S_2$ | 509.5 | 509.1 |
| 19b11 | 4-chlorophenylsulfonyl | $C_{25}H_{24}Cl_2N_2O_3S$ | 503.5 | 503.1 |
| 19b12 | 2,3-dichlorophenylsulfonyl | $C_{25}H_{23}Cl_3N_2O_3S$ | 537.9 | 539.1 |
| 19b13 | 2,6-dichlorophenylsulfonyl | $C_{25}H_{23}Cl_3N_2O_3S$ | 537.9 | 539.1 |

-continued

| Cpd. # | R⁵ | Mol. Formula | Mol. Wt. | Obs. Mass (M + 1)⁺ |
|---|---|---|---|---|
| 19b14 | (2,4-dichlorophenylsulfonyl) | $C_{25}H_{23}Cl_3N_2O_3S$ | 537.9 | 539.1 |
| 19b15 | (2,5-dichlorophenylsulfonyl) | $C_{25}H_{23}Cl_3N_2O_3S$ | 537.9 | 539.1 |
| 19b16 | (2-fluorophenylsulfonyl) | $C_{25}H_{24}ClFN_2O_3S$ | 487.0 | 487.1 |
| 19b17 | (4-methoxyphenylsulfonyl) | $C_{26}H_{27}ClN_2O_4S$ | 499.0 | 499.1 |
| 19b18 | (naphthalen-1-ylsulfonyl) | $C_{29}H_{27}ClN_2O_3S$ | 519.1 | 519.1 |
| 19b19 | (naphthalen-2-ylsulfonyl) | $C_{29}H_{27}ClN_2O_3S$ | 519.1 | 519.1 |
| 19b20 | (2-(naphthalen-1-yl)ethylsulfonyl) | $C_{31}H_{31}ClN_2O_3S$ | 547.1 | 547.1 |

-continued

| Cpd. # | R⁵ | Mol. Formula | Mol. Wt. | Obs. Mass (M + 1)⁺ |
|---|---|---|---|---|
| 19b21 | (1-methylimidazol-4-yl)sulfonyl | $C_{23}H_{25}ClN_4O_3S$ | 473.0 | 473.0 |
| 19b22 | (3-methyl-5-chloro-1-methylpyrazol-4-yl)sulfonyl | $C_{24}H_{26}Cl_2N_4O_3S$ | 521.5 | 521.5 |
| 19b23 | propylsulfonyl | $C_{22}H_{27}ClN_2O_3S$ | 435.0 | 435.0 |
| 19b24 | (3-cyanophenyl)sulfonyl | $C_{26}H_{24}ClN_3O_3S$ | 494.0 | 494.0 |
| 19b25 | (3,5-dichlorophenyl)sulfonyl | $C_{25}H_{23}Cl_3N_2O_3S$ | 537.9 | 537.9 |
| 19b26 | (3,4-dichlorophenyl)sulfonyl | $C_{25}H_{23}Cl_3N_2O_3S$ | 537.9 | 537.9 |

-continued

| Cpd. # | R⁵ | Mol. Formula | Mol. Wt. | Obs. Mass (M + 1)⁺ |
|---|---|---|---|---|
| 19b27 | 4-(trifluoromethyl)phenylsulfonyl | $C_{26}H_{24}ClF_3N_2O_3S$ | 537.0 | 537.0 |
| 19b28 | 3-(trifluoromethyl)phenylsulfonyl | $C_{26}H_{24}ClF_3N_2O_3S$ | 537.0 | 537.0 |
| 19b29 | benzo[c][1,2,5]oxadiazol-4-ylsulfonyl | $C_{25}H_{23}ClN_4O_4S$ | 511.0 | 511.0 |
| 19b30 | thiophen-2-ylsulfonyl | $C_{23}H_{23}ClN_2O_3S_2$ | 475.0 | 475.0 |
| 19b31 | benzylsulfonyl | $C_{26}H_{27}ClN_2O_3S$ | 483.0 | 483.0 |
| 19b32 | N,N-dimethylsulfamoyl | $C_{21}H_{26}ClN_3O_3S$ | 436 | 436.1 |

Method 20

The following compounds can be synthesized using similar methodology starting with the regioisomeric resin-bound aniline 17.

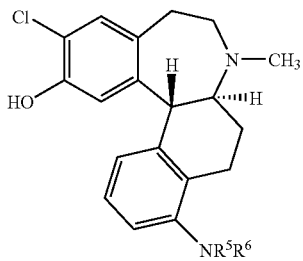

20a wherein $R^6$ is hydrogen and $R^5$ is $C(O)NR^3R^4$:

| Cpd. # | NR³R⁴ | Mol. Formula | Mol. Wt. | Obs. Mass (M + 1)⁺ |
|---|---|---|---|---|
| 20a1 | (3-chlorophenyl-NH) | C₂₆H₂₅Cl₂N₃O₂ | 482.4 | 484.1 |
| 20a2 | (benzyl-NH) | C₂₇H₂₈ClN₃O₂ | 462.0 | 463.1 |
| 20a3 | (4-chlorophenyl-NH) | C₂₆H₂₅Cl₂N₃O₂ | 482.4 | 484.1 |
| 20a4 | (2-chlorophenyl-NH) | C₂₆H₂₅Cl₂N₃O₂ | 482.4 | 484.1 |
| 20a5 | (ethyl-NH) | C₂₂H₂₆ClN₃O₂ | 399.9 | 401.1 |
| 20a6 | (morpholino) | C₂₄H₂₈ClN₃O₃ | 442.0 | 443.1 |
| 20a7 | (pyrrolidinyl) | C₂₄H₂₈ClN₃O₂ | 426.0 | 427.1 |
| 20a8 | (isopropyl-NH) | C₂₂H₂₆ClN₃O₂ | 399.9 | 401.1 |
| 20a9 | (cyclohexyl-NH) | C₂₆H₃₂ClN₃O₂ | 454.0 | 455.1 |
| 20a10 | (3-methoxyphenyl-NH) | C₂₇H₂₈ClN₃O₃ | 478.0 | 479.3 |
| 20a11 | (4-methoxyphenyl-NH) | C₂₇H₂₈ClN₃O₃ | 478.0 | 479.3 |

-continued

| Cpd. # | NR³R⁴ | Mol. Formula | Mol. Wt. | Obs. Mass (M + 1)⁺ |
|---|---|---|---|---|
| 20a12 | 3-cyanophenyl-NH- | $C_{27}H_{25}ClN_4O_2$ | 473.0 | 474.3 |
| 20a13 | 4-cyanophenyl-NH- | $C_{27}H_{25}ClN_4O_2$ | 473.0 | 474.3 |
| 20a14 | 3-fluorophenyl-NH- | $C_{26}H_{25}ClFN_3O_2$ | 466.0 | 467.3 |
| 20a15 | 2-fluorophenyl-NH- | $C_{26}H_{25}ClFN_3O_2$ | 466.0 | 467.3 |
| 20a16 | 4-fluorophenyl-NH- | $C_{26}H_{25}ClFN_3O_2$ | 466.0 | 467.3 |
| 20a17 | 4-acetylphenyl-NH- | $C_{28}H_{28}ClN_3O_3$ | 490.0 | 491.3 |

-continued

| Cpd. # | NR³R⁴ | Mol. Formula | Mol. Wt. | Obs. Mass (M + 1)⁺ |
|---|---|---|---|---|
| 20a18 | 2,5-dichlorophenyl-NH- | $C_{26}H_{24}Cl_3N_3O_2$ | 516.9 | 518.3 |
| 20a19 | 2,6-dichlorophenyl-NH- | $C_{26}H_{24}Cl_3N_3O_2$ | 516.9 | 518.3 |
| 20a20 | 2,3-dichlorophenyl-NH- | $C_{26}H_{24}Cl_3N_3O_2$ | 516.9 | 518.3 |
| 20a21 | 3,4-dichlorobenzyl-NH- | $C_{27}H_{26}Cl_3N_3O_2$ | 530.9 | 532.3 |
| 20a22 | naphthalen-1-yl-NH- | $C_{30}H_{28}ClN_3O_2$ | 498.0 | 499.3 |
| 20a23 | 3-(trifluoromethyl)phenyl-NH- | $C_{27}H_{25}ClF_3N_3O_2$ | 516.0 | 517.3 |

-continued
| Cpd. # | NR³R⁴ | Mol. Formula | Mol. Wt. | Obs. Mass (M + 1)⁺ |
|---|---|---|---|---|
| 20a24 | 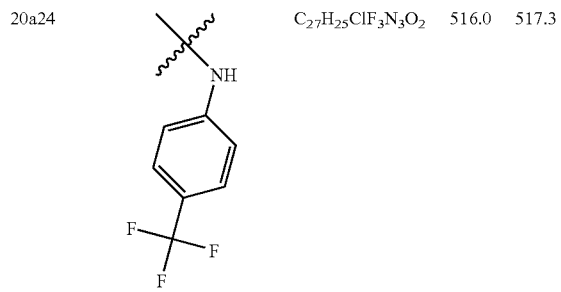 | $C_{27}H_{25}ClF_3N_3O_2$ | 516.0 | 517.3 |
| 20a25 | 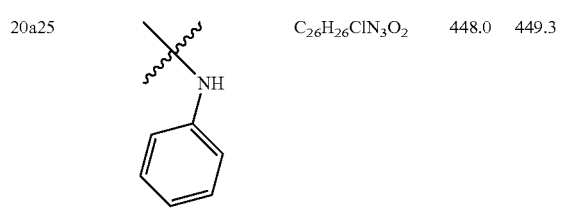 | $C_{26}H_{26}ClN_3O_2$ | 448.0 | 449.3 |
| 20a26 | 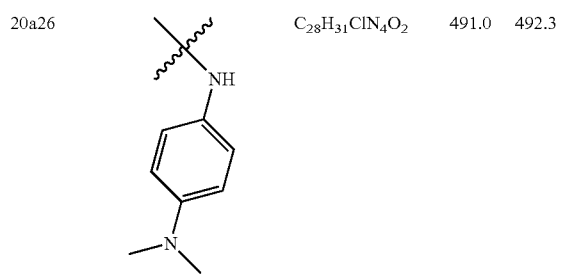 | $C_{28}H_{31}ClN_4O_2$ | 491.0 | 492.3 |
| 20a27 | 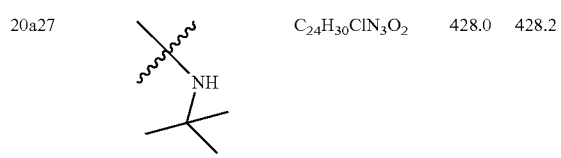 | $C_{24}H_{30}ClN_3O_2$ | 428.0 | 428.2 |
| 20a28 | 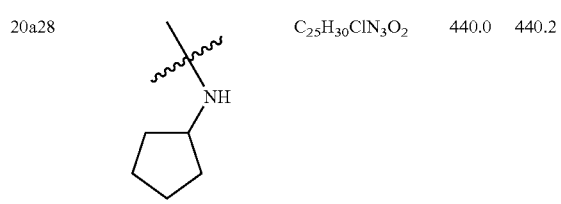 | $C_{25}H_{30}ClN_3O_2$ | 440.0 | 440.2 |
-continued
| Cpd. # | NR³R⁴ | Mol. Formula | Mol. Wt. | Obs. Mass (M + 1)⁺ |
|---|---|---|---|---|
| 20a29 | 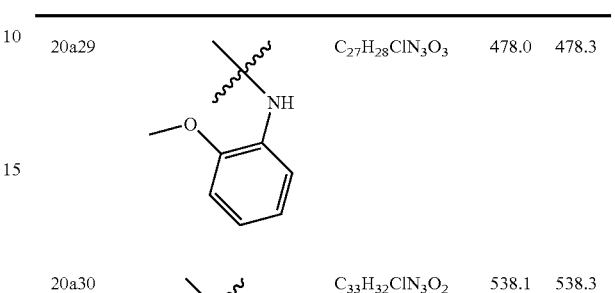 | $C_{27}H_{28}ClN_3O_3$ | 478.0 | 478.3 |
| 20a30 | 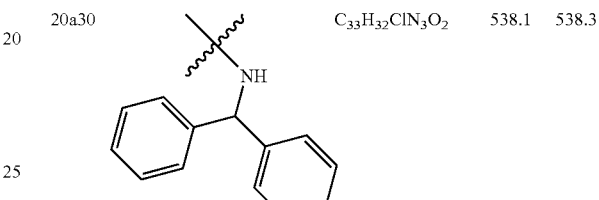 | $C_{33}H_{32}ClN_3O_2$ | 538.1 | 538.3 |
| 20a31 | 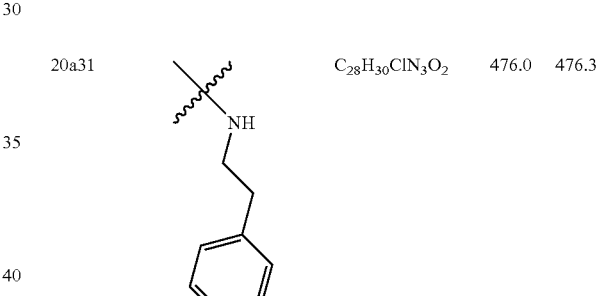 | $C_{28}H_{30}ClN_3O_2$ | 476.0 | 476.3 |
| 20a32 | 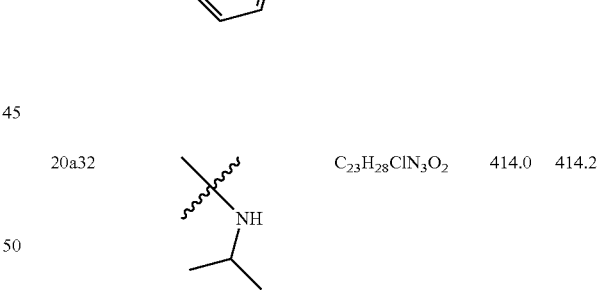 | $C_{23}H_{28}ClN_3O_2$ | 414.0 | 414.2 |
| 20a33 | 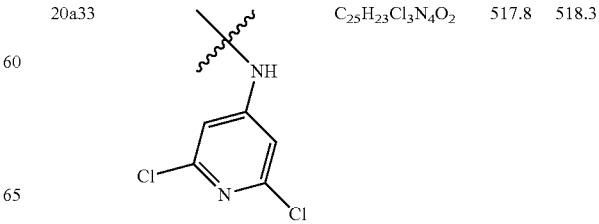 | $C_{25}H_{23}Cl_3N_4O_2$ | 517.8 | 518.3 |

-continued

| Cpd. # | NR³R⁴ | Mol. Formula | Mol. Wt. | Obs. Mass (M + 1)⁺ |
|---|---|---|---|---|

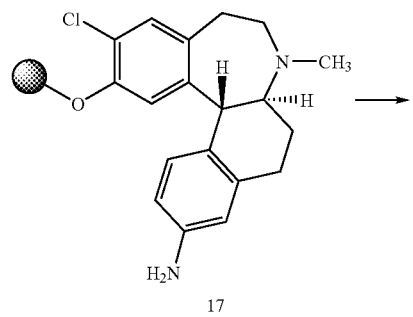

17

↓

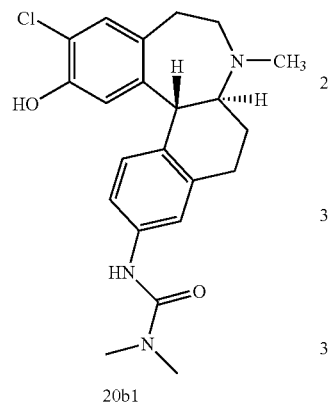

20b1

To 0.03 g of the resin-bound aniline 17 (0.69 mmol/g) pre-swelled in pyridine was added a solution of N,N'-dimethylaminocarbonylchloride (5 eq). The mixture was agitated overnight and the resin was washed with DMF, THF, dichloromethane and methanol. The product was cleaved from the resin with 30% TFA in dichloromethane to give compound 20b1. RP-LC MS: m/z calcd for $C_{22}H_{27}ClN_3O_2^+$=400.1; found m/z=400.1 (M+1)⁺.

The following compounds can be synthesized using similar methodology.

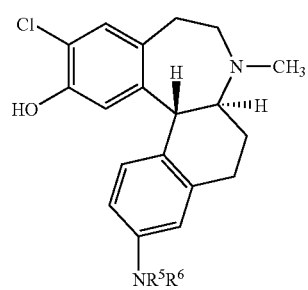

20b wherein R⁶ is hydrogen and R⁵ is C(O)NR³R⁴:

| Cpd. # | NR³R⁴ | Mol. Formula | Mol. Wt. | Obs. Mass (M + 1)⁺ |
|---|---|---|---|---|
| 20b2 | 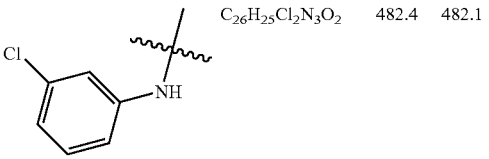 | C₂₆H₂₅Cl₂N₃O₂ | 482.4 | 482.1 |
| 20b3 | 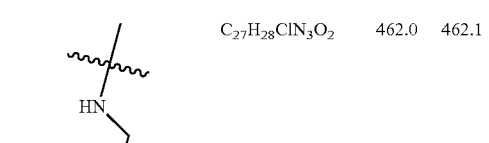 | C₂₇H₂₈ClN₃O₂ | 462.0 | 462.1 |
| 20b4 |  | C₂₆H₂₅Cl₂N₃O₂ | 482.4 | 482.1 |
| 20b5 | 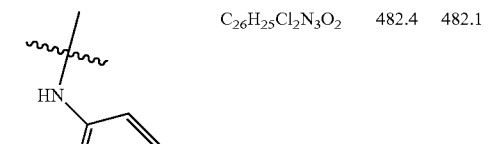 | C₂₆H₂₅Cl₂N₃O₂ | 482.4 | 482.1 |
| 20b6 | 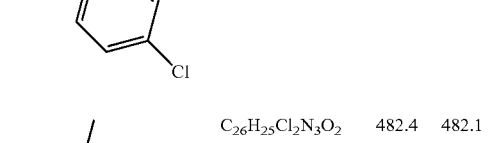 | C₂₂H₂₆ClN₃O₂ | 399.9 | 399.9 |
| 20b7 |  | C₂₄H₂₈ClN₃O₃ | 442.0 | 442.0 |
| 20b8 | 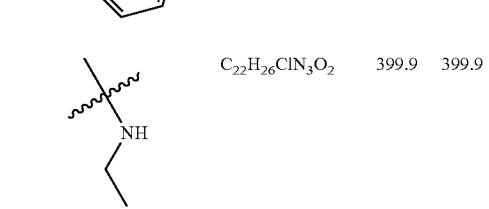 | C₂₄H₂₈ClN₃O₂ | 426.0 | 426.0 |

-continued

| Cpd. # | NR³R⁴ | Mol. Formula | Mol. Wt. | Obs. Mass (M + 1)⁺ |
|---|---|---|---|---|
| 20b9 | N(CH₃)(phenyl) | $C_{27}H_{28}ClN_3O_2$ | 462.0 | 462.0 |
| 20b10 | NH-cyclohexyl | $C_{26}H_{32}ClN_3O_2$ | 454.0 | 454.0 |
| 20b11 | NH-(2-methoxyphenyl) | $C_{27}H_{28}ClN_3O_3$ | 478.0 | 478.3 |
| 20b12 | NH-(3-methoxyphenyl) | $C_{27}H_{28}ClN_3O_3$ | 478.0 | 478.3 |
| 20b13 | NH-(4-methoxyphenyl) | $C_{27}H_{28}ClN_3O_3$ | 478.0 | 478.3 |
| 20b14 | NH-(3-cyanophenyl) | $C_{27}H_{25}ClN_4O_2$ | 473.0 | 473.3 |
| 20b15 | NH-(4-cyanophenyl) | $C_{27}H_{25}ClN_4O_2$ | 473.0 | 473.3 |
| 20b16 | NH-(3-fluorophenyl) | $C_{26}H_{25}ClFN_3O_2$ | 466.0 | 466.3 |
| 20b17 | NH-(2-fluorophenyl) | $C_{26}H_{25}ClFN_3O_2$ | 466.0 | 466.3 |
| 20b18 | NH-(4-fluorophenyl) | $C_{26}H_{25}ClFN_3O_2$ | 466.0 | 466.3 |
| 20b19 | NH-(4-acetylphenyl) | $C_{28}H_{28}ClN_3O_3$ | 490.0 | 490.3 |
| 20b20 | NH-(2,5-dichlorophenyl) | $C_{26}H_{24}Cl_3N_3O_2$ | 516.9 | 517.3 |

-continued

| Cpd. # | NR³R⁴ | Mol. Formula | Mol. Wt. | Obs. Mass (M + 1)⁺ |
|---|---|---|---|---|
| 20b21 | HN-(2,3-dichlorophenyl) | $C_{26}H_{24}Cl_3N_3O_2$ | 516.9 | 517.3 |
| 20b22 | HN-CH₂-(3,4-dichlorophenyl) | $C_{27}H_{26}Cl_3N_3O_2$ | 530.9 | 531.3 |
| 20b23 | HN-(1-naphthyl) | $C_{30}H_{28}ClN_3O_2$ | 498.0 | 498.3 |
| 20b24 | HN-(4-trifluoromethylphenyl) | $C_{27}H_{25}ClF_3N_3O_2$ | 516.0 | 516.3 |
| 20b25 | HN-phenyl | $C_{26}H_{26}ClN_3O_2$ | 448.0 | 448.3 |
| 20b26 | HN-(4-dimethylaminophenyl) | $C_{28}H_{31}ClN_4O_2$ | 491.0 | 491.3 |

-continued

| Cpd. # | NR³R⁴ | Mol. Formula | Mol. Wt. | Obs. Mass (M + 1)⁺ |
|---|---|---|---|---|
| 20b27 | NH-t-butyl | $C_{24}H_{30}ClN_3O_2$ | 428.0 | 428.2 |
| 20b28 | HN-cyclopentyl | $C_{25}H_{30}ClN_3O_2$ | 440.0 | 440.2 |
| 20b29 | HN-CH(phenyl)₂ | $C_{33}H_{32}ClN_3O_2$ | 538.1 | 538.3 |
| 20b30 | HN-(2,6-dichlorophenyl) | $C_{26}H_{24}Cl_3N_3O_2$ | 516.9 | 517.3 |
| 20b31 | HN-CH₂CH₂-phenyl | $C_{38}H_{30}ClN_3O_2$ | 476.0 | 476.23 |
| 20b32 | HN-(3-trifluoromethylphenyl) | $C_{27}H_{25}ClF_3N_3O_2$ | 516.0 | 516.3 |

-continued

| Cpd. # | NR³R⁴ | Mol. Formula | Mol. Wt. | Obs. Mass (M + 1)⁺ |
|---|---|---|---|---|
| 20b33 | | $C_{23}H_{28}ClN_3O_2$ | 414.0 | 414.2 |
| 20b34 | | $C_{25}H_{23}Cl_3N_4O_2$ | 517.8 | 518.3 |

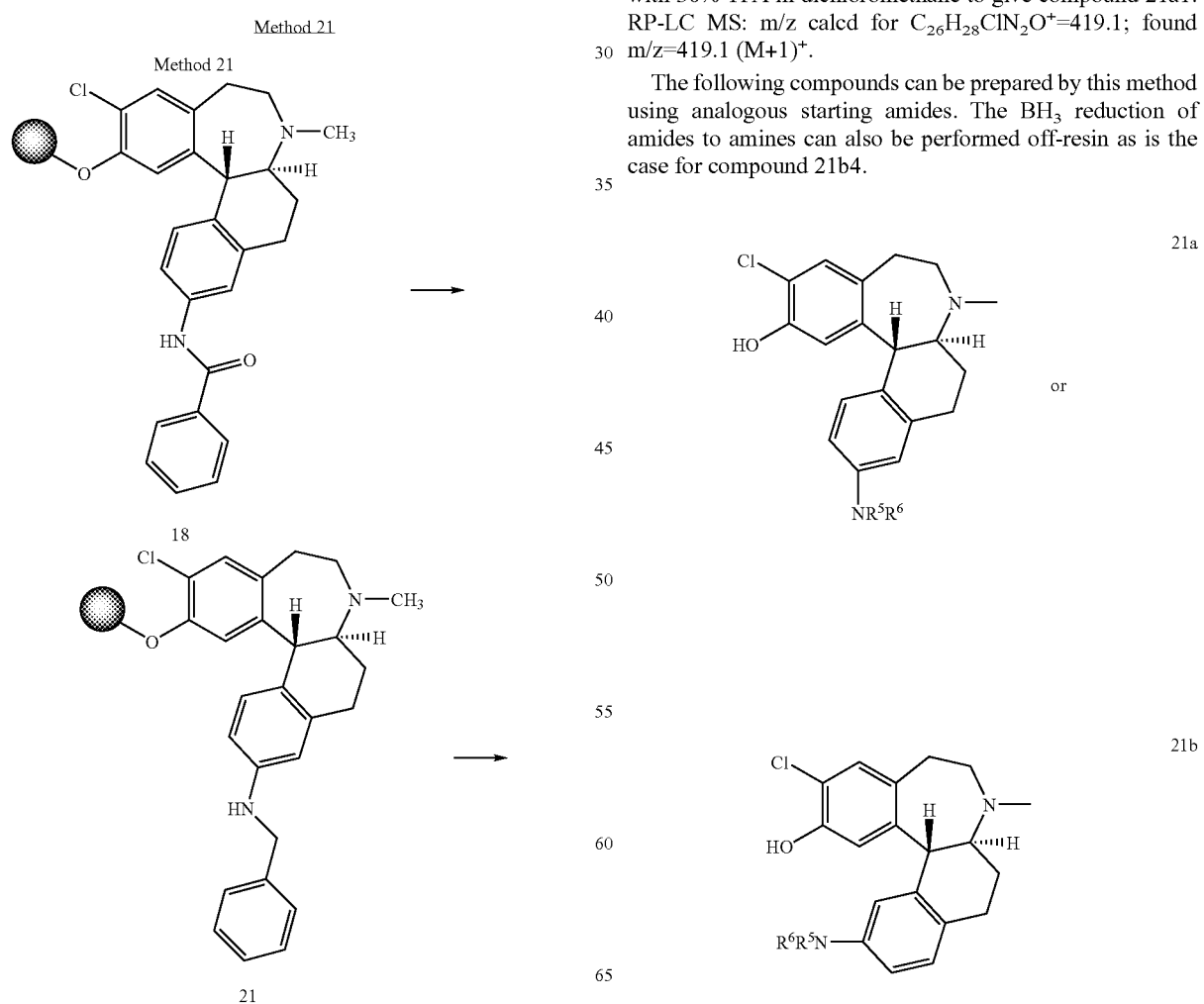

-continued

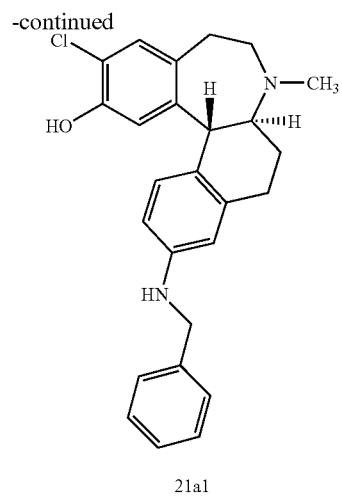

To 0.100 g of pre-swelled resin 18 (0.69 mmol/g) was added 4 mL of 2N $BH_3$ in THF and the mixture was agitated overnight. The resin was sequentially washed with methanol, 0.5 M NaOMe in methanol, dichloromethane, THF, and methanol. The product was cleaved from 0.050 g of the resin with 30% TFA in dichloromethane to give compound 21a1. RP-LC MS: m/z calcd for $C_{26}H_{28}ClN_2O^+$=419.1; found m/z=419.1 (M+1)⁺.

The following compounds can be prepared by this method using analogous starting amides. The $BH_3$ reduction of amides to amines can also be performed off-resin as is the case for compound 21b4.

wherein R⁶ is hydrogen:
| Cpd. # | NR⁵R⁶ | Mol. Formula | Mol. Wt. | Obs. Mass (M + 1)⁺ |
|---|---|---|---|---|
| 21a2 | 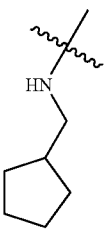 | $C_{25}H_{31}ClN_2O$ | 410.99 | 411.1 |
| 21a3 | 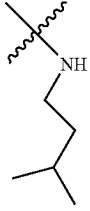 | $C_{24}H_{31}ClN_2O$ | 398.98 | 399.1 |
| 21b1 | 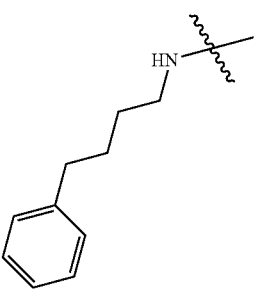 | $C_{29}H_{33}ClN_2O$ | 461.05 | 461.1 |
| 21b2 | 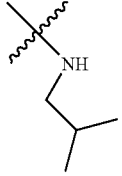 | $C_{23}H_{29}ClN_2O$ | 384.95 | 385.1 |
| 21b3 | 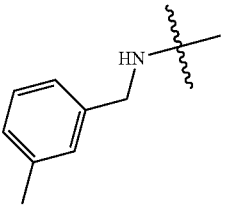 | $C_{27}H_{29}ClN_2O$ | 433.0 | 433.1 |
| 21b4 | 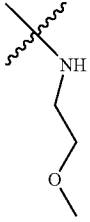 | $C_{22}H_{27}ClN_2O_2$ | 386.9 | 387.1 |

Method 22
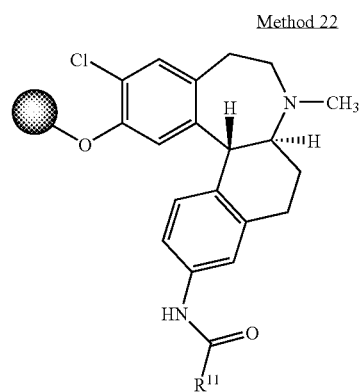
18
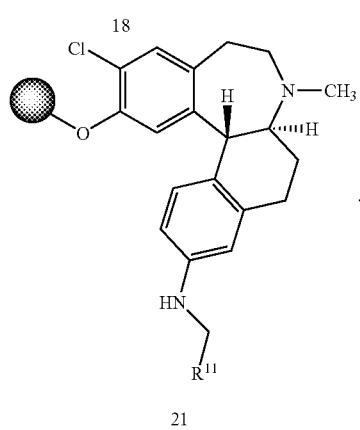
21
-continued
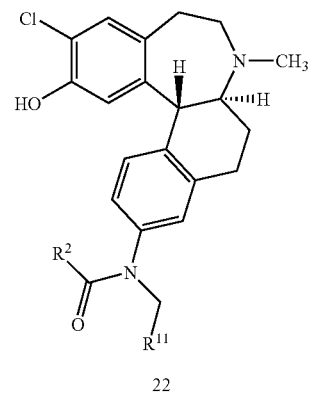
22
The following compounds were synthesized using method 18 starting with resin bound N-alkylanilines 21 generated from method 21.
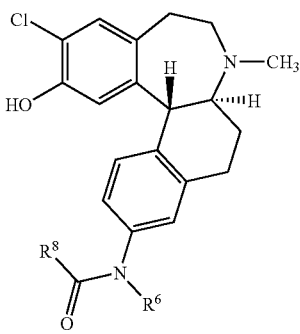
22a
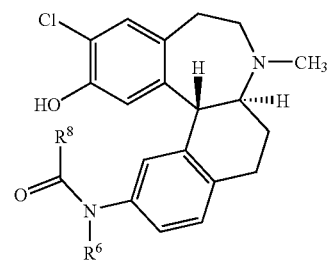
22b
| Cpd. # | R[8] | R[6] | Mol. Formula | Mol. Wt. | Ret. Time (min) | Obs. Mass (M + 1)[+] |
|---|---|---|---|---|---|---|
| 22a1 | 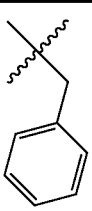 | $CH_2CH_3$ | $C_{28}H_{29}ClN_2O_2$ | 461.0 | 4.26 | 461.1 |

-continued
| | | | | | | |
|---|---|---|---|---|---|---|
| 22a2 |  | CH$_2$CH$_3$ | C$_{27}$H$_{33}$ClN$_2$O$_2$ | 453.0 | 4.31 | 453.1 |
| 22a3 |  | CH$_2$CH$_3$ | C$_{26}$H$_{33}$ClN$_2$O$_2$ | 441.0 | 4.31 | 441.1 |
| 22b1 | 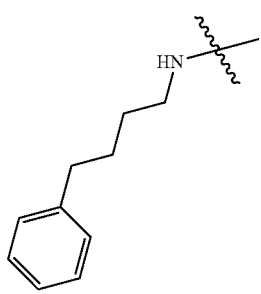 | CH$_2$CH$_3$ | C$_{31}$H$_{33}$ClN$_2$O$_2$ | 503.1 | 4.66 | 503.1 |
| 22b2 |  | CH$_2$CH$_3$ | C$_{24}$H$_{29}$ClN$_2$O$_3$ | 429.0 | 3.56 | 429.1 |
| 22b3 | 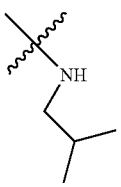 | CH$_2$CH$_3$ | C$_{25}$H$_{31}$ClN$_2$O$_2$ | 427.0 | 4.01 | 427.1 |
| 22b4 | 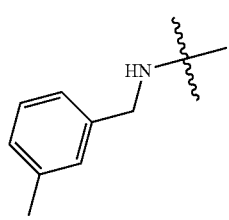 | CH$_2$CH$_3$ | C$_{29}$H$_{31}$ClN$_2$O$_2$ | 475.0 | 4.41 | 475.1 |

Method 23

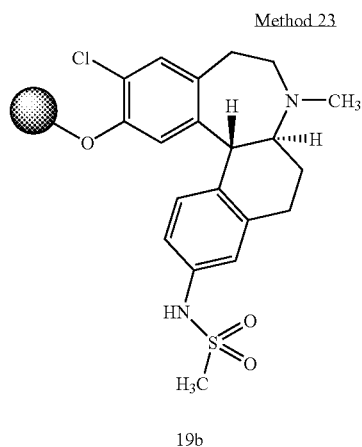

19b

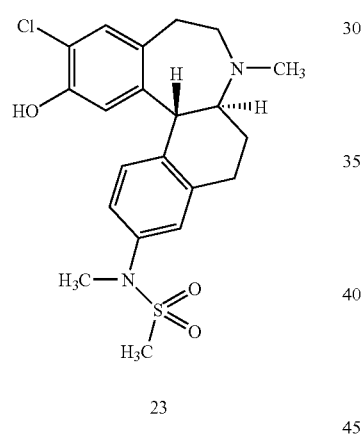

23

Method 24

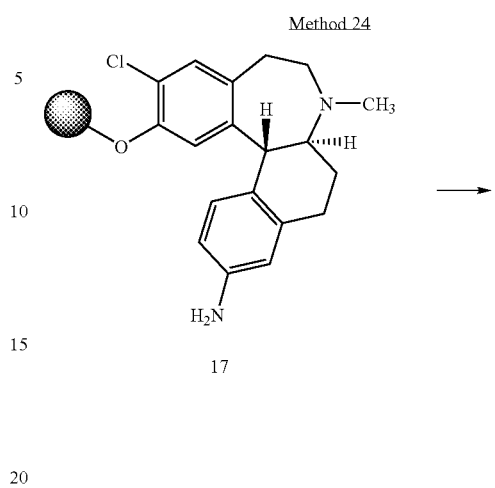

17

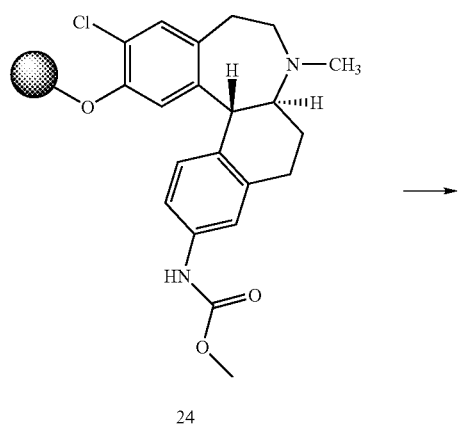

24

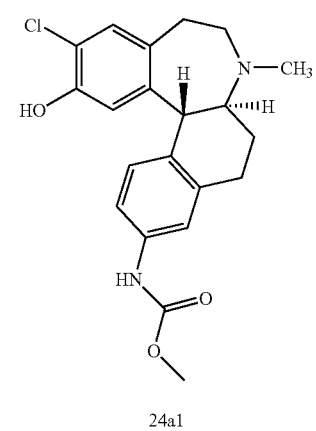

24a1

To a mixture of 0.21 g (0.7 mmol/g) of the sulfonylated resin 19b, 0.19 g (0.725 mmoL, 5 eq) of triphenylphosphine, 0.30 ml (10 eq) of anhydrous methanol in 6 mL of tetrahydrofuran was added a solution of 0.185 g (0.735 mmol, 5 eq.) of 1,1'-(azodicarbonyl)dipiperidine in 2 mL of dichloromethane. The reaction mixture was degassed with nitrogen and shaken overnight with heating at 70° C. The resin was filtered, and washed twice with 5% acetic acid (AcOH) in dichloromethane, each time shaking for 20 minutes. The resin was then washed consecutively with dichloromethane, THF and methanol (3 times each), and finally washed with twice with dichloromethane. The compound was cleaved with 30% trifluoroacetic acid in dichloromethane for 30 min. The product was isolated by preparative thin layer chromatography eluting with 5% methanol in dichloromethane containing 0.5% triethylamine) to give 0.006 g of 23. RP-LC MS: RT=3.16 min, m/z cacld for $C_{21}H_{26}ClN_2O_3S^+$=421.14 $(M+1)^+$, found m/z=421.1.

To 0.035 g of the resin-bound aniline 17 (0.69 mmol/g) pre-swelled in dichloromethane was added a solution of methychloroformate (5 eq) in dichloromethane. The mixture was agitated overnight and the resin washed sequentially with THF, dichloromethane and methanol. T he product was cleaved from the resin with 30% TFA in dichloromethane to give 4 mg of compound 24a1. RP-LC MS: m/z calcd for $C_{21}H_{24}ClN_2O_3^+$=387.1; found m/z=387.1 $(M+1)^+$.

The following compounds were synthesized using the same method.

| Cpd. # | R⁸ | Mol. Formula | Mol. Wt. | Obs. Mass (M + 1)⁺ |
|---|---|---|---|---|
| 24a2 | Et— | $C_{22}H_{25}ClN_2O_3$ | 400.9 | 400.9 |
| 24a3 | (4-methoxyphenyl) | $C_{27}H_{27}ClN_2O_4$ | 479.0 | 479.0 |
| 24a4 | PhCH₂— | $C_{27}H_{27}ClN_2O_3$ | 463.0 | 463.0 |
| 24a5 | n-Bu— | $C_{24}H_{29}ClN_2O_3$ | 429.0 | 429.1 |
| 24b1 | Et— | $C_{22}H_{25}ClN_2O_3$ | 400.9 | 402.1 |
| 24b2 | (4-methoxyphenyl) | $C_{27}H_{27}ClN_2O_4$ | 479.0 | 480.1 |

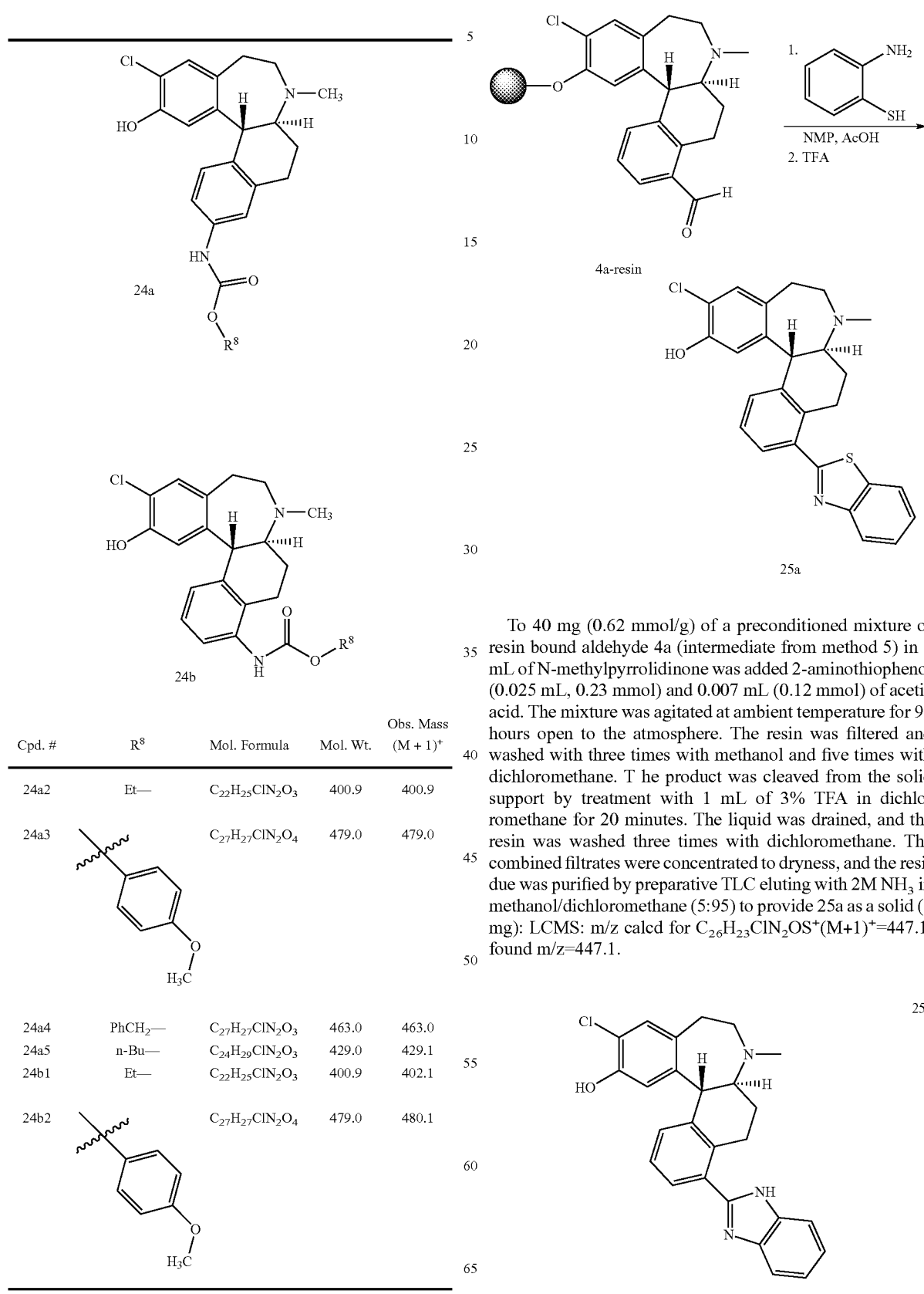

Method 25

4a-resin

25a

To 40 mg (0.62 mmol/g) of a preconditioned mixture of resin bound aldehyde 4a (intermediate from method 5) in 1 mL of N-methylpyrrolidinone was added 2-aminothiophenol (0.025 mL, 0.23 mmol) and 0.007 mL (0.12 mmol) of acetic acid. The mixture was agitated at ambient temperature for 96 hours open to the atmosphere. The resin was filtered and washed with three times with methanol and five times with dichloromethane. The product was cleaved from the solid support by treatment with 1 mL of 3% TFA in dichloromethane for 20 minutes. The liquid was drained, and the resin was washed three times with dichloromethane. The combined filtrates were concentrated to dryness, and the residue was purified by preparative TLC eluting with 2M $NH_3$ in methanol/dichloromethane (5:95) to provide 25a as a solid (6 mg): LCMS: m/z calcd for $C_{26}H_{23}ClN_2OS^+(M+1)^+=447.1$, found m/z=447.1.

25b

Compound 25b could also be prepared using similar methodology starting with 1,2-phenylenediamine: LCMS: m/z calcd for $C_{26}H_{23}ClN_3O^+$ (M+1)$^+$=430.7. found m/z=430.1.

Method 25.1

Analogously to method 25, the imidazole derivative 25c could be prepared from aldehyde 4a as follows:

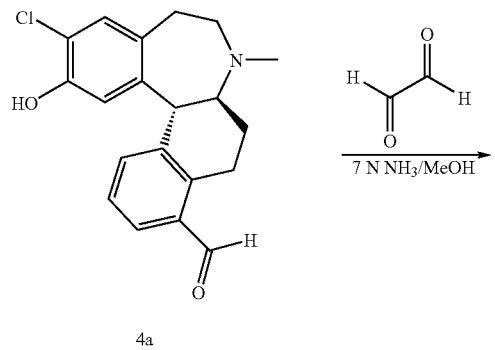

To a mixture of 60 mg (0.18 mmol) of aldehyde 4a and 0.070 mL of glyoxal (40% in H$_2$O, 0.48 mmol) cooled to 0° C. was added 1.6 mL (11.2 mmol) of 7N ammonia in methanol solution. The mixture was sealed and stirred at ambient temperature for 68 hours. The solvent was removed in vacuo and the dark residue was purified by preparative TLC eluting with 1% Et$_2$NH in methanol/dichloromethane (5:95) to provide 49 mg of 25c as a solid: LCMS: m/z calcd for $C_{22}H_{23}ClN_3O^+$ (M+1)$^+$=380.1; found m/z=380.1.

Method 26

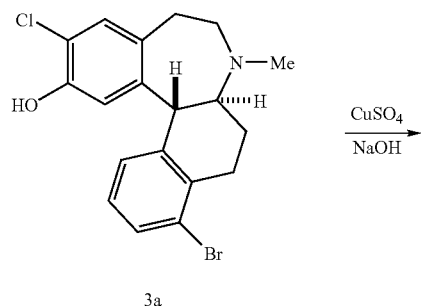

To a solution of NaOH (1 g) in 10 mL water was added CuSO$_4$ (0.5 g) and the resulting mixture was stirred for 15 minutes at room temperature. Compound 3a (0.1 g, 2.54 mmol) was added and the mixture was heated at 135° C. for 48 hours. The mixture was neutralized with 6N HCl and poured into a mixture of saturated NaHCO$_3$/dichloromethane. The mixture was extracted with dichloromethane and the organic layer was dried over sodium sulfate. The solvent was removed in vacuo and the product was isolated by preparative TLC using 10% methanol/dichloromethane as eluent to give 0.03 g of the desired phenol 26a: ES MS: m/z calcd for $C_{19}H_{20}ClNO_2{}^{30}$=330.1; found m/z=330.1 (M+1)$^+$.

Method 27

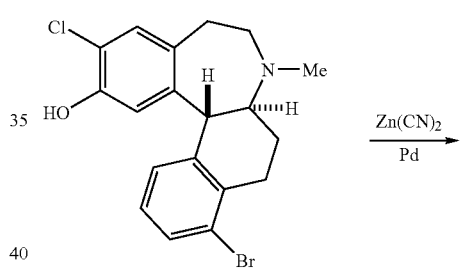

Compound 3a (1 g, 2.54 mmol) was mixed with Zn(CN)$_2$ (0.3 g, 2.56 mmol, 1 eq), Pd$_2$(dba)$_3$ (0.116 g, 5 mol %) and dppf (0.17 g, 12 mol %) in 10 mL of DMF. Water (100 μL) was added and the mixture was heated in a sealed tube for 12 hours. Ethyl acetate (200 mL) and 50 mL of water was added and the mixture was reextracted with ethyl acetate (200 mL). The combined organic layers were washed with water and brine, dried over sodium sulfate, and evaporated in vacuo. The product was purified by silica gel column chromatography using 10% MeOH in dichloromethane as eluent to give 0.76 g of the cyano compound, 27a. ES MS: m/z calcd for $C_{20}H_{20}ClN_2O^+$=339.1; found m/z=339.1 (M+1)$^+$.

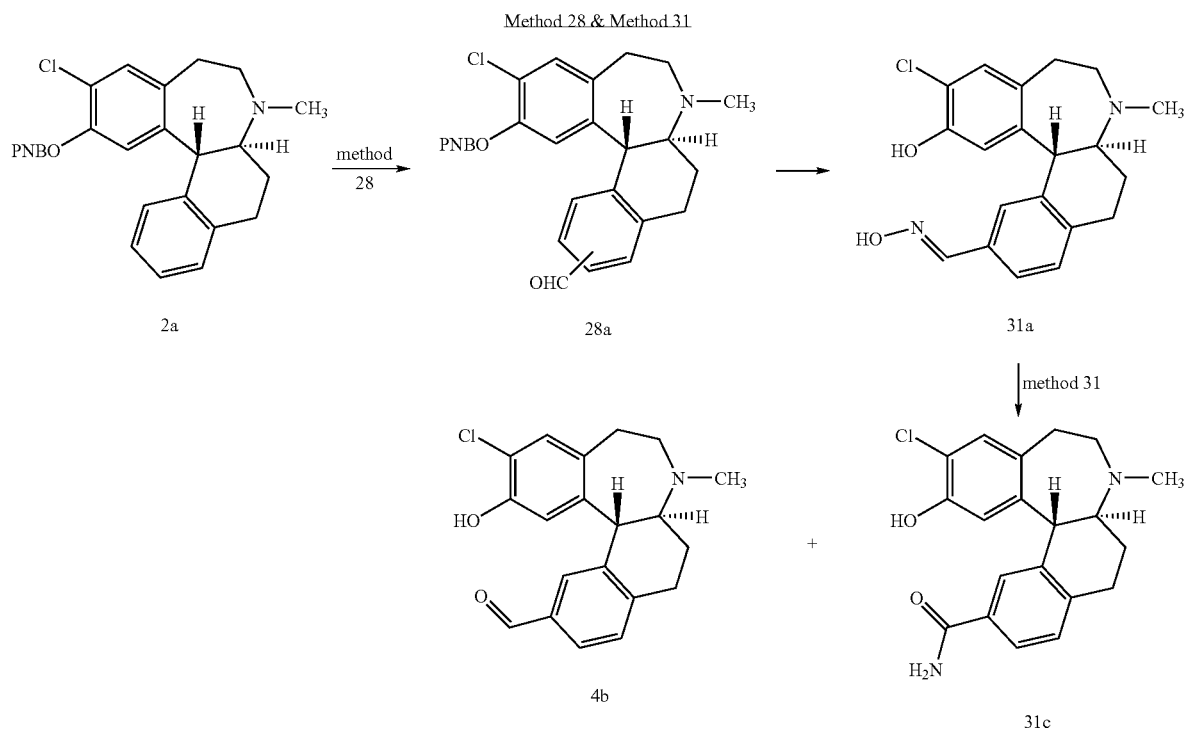

To a suspension of 1.1 of AlCl$_3$ (4.2 eq) in 20 ml of anhydrous dichloroethane (DCE) cooled to −15° C. was added 1 eq of 2a in 5 ml of DCE followed by 1,1-dichloromethylmethylether (4 eq). The reaction was warmed to room temperature and quenched with by addition of 2.0 g of tartaric acid. The mixture was diluted with water and extracted with dichloromethane. The combined organic layers were dried and evaporated to give 1.2 g of a mixture of regioisomeric aldehydes 28a in an approximate ratio 1:1:3 as the 10:11:12-isomers.

A solution of 0.5 g of 28a (1 mmol) and hydroxyamine hydrochloride (2 eq) in 5 ml of pyridine was heated under reflux for 30 min and the solvent was removed in vacuo. The residue was dissolved in dichloromethane and washed with saturated sodium bicarbonate solution. The organic layer was dried over sodium sulfate and the solvent was evaporated to give a solid. Recrystallization from methanol gave 200 mg of oxime 31a. RP-LC MS: calcd for $C_{20}H_{22}ClN_2O_2{}^+$=357.1; found=357.1 $(M+1)^+$.

A mixture of 500 mg of 31a (1 mmol) in aqueous Ti(III)Cl$_3$ (5 ml, 8.9% wt in 30% HCl) was stirred overnight under nitrogen. The mixture was poured into saturated sodium carbonate followed by extraction with dichloromethane. The combined organic layers were dried and the solvent evaporated to give a mixture of two products which was chromatographed over silica gel eluting to give 290 mg 4b and 150 mg of 31c: RP-LC MS: calcd for $C_{20}H_{22}ClN_2O_2{}^+$=357.1; found=357.1 $(M+1)^+$.

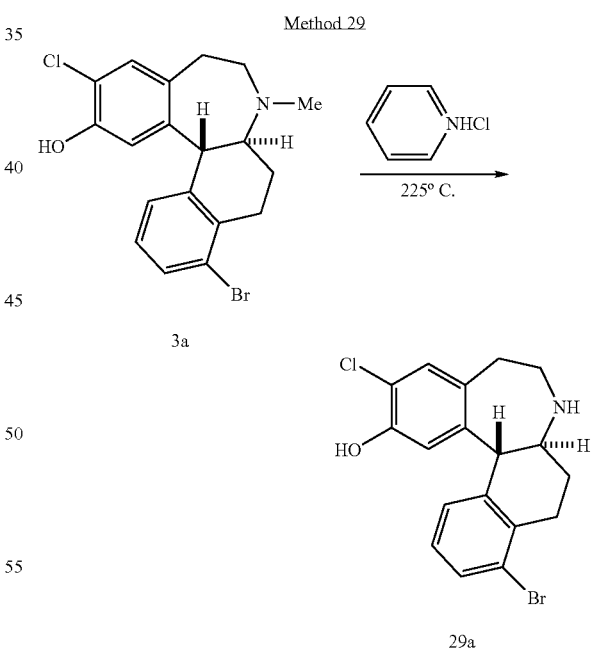

A mixture of pyridine (8.5 mL) and concentrated aqueous HCl (10 mL) was heated at 225° C. for 30 minutes and the water was removed by using a Dean-Stark apparatus. To this pyridine.HCl salt, compound 3a (0.1 g, 0.254 mmol) was added and heated at 225° C. for 16 hours. The reaction mixture was cooled to room temperature and carefully quenched by the addition of saturated NaHCO$_3$ solution (100 mL). The mixture was extracted with ethyl acetate and the organic layer was washed with brine. It was dried over sodium sulfate and the solvent was evaporated in vacuo. The compound was isolated by silica gel column chromatography using 3-10% MeOH in dichloromethane to give 0.05 g of the demethylated product 29a: ES MS: m/z calcd for $C_{18}H_{18}BrClNO^+$=380.1; found m/z=380.1 (M+1)$^+$.

The following compounds can also be prepared by this method:

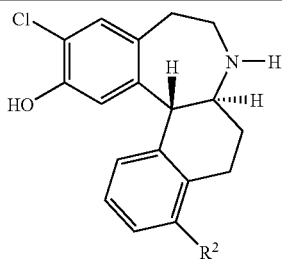

| Cpd. # | R$^2$ | Analytical data |
|---|---|---|
| 29b | —CN | ES MS: calcd for $C_{19}H_{18}ClN_2O^+$ = 325.1; found = 325.1 (M + 1)$^+$ |
| 29c | 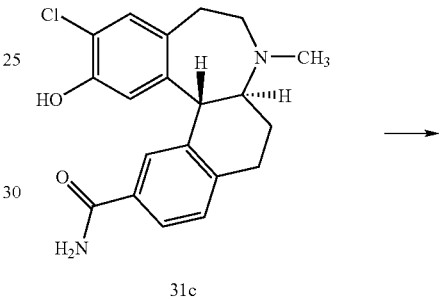 | ES MS: calcd for $C_{23}H_{22}ClN_2O^+$ = 377.1; found = 377.1 (M + 1)$^+$ |

Method 30

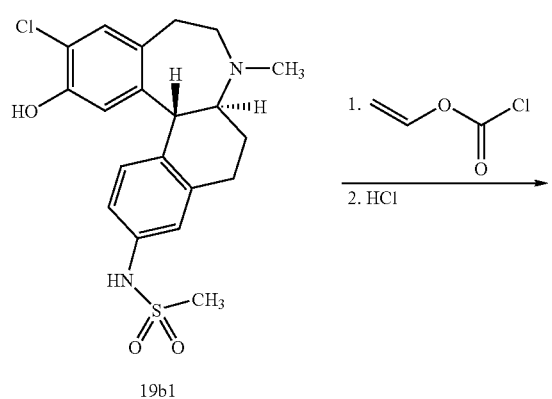

To a suspension of 0.116 g (0.25 mmol) of the hydrochloric acid salt of 19b1 and 0.214 g (1.0 mmol) proton sponge in 5 mL of dichloromethane was added 0.12 g (1.13 mmol) of vinyl chloroformate and the mixture was heated overnight at reflux. The intermediate was isolated by silica gel preparative thin layer chromatography eluting with 10% methanol in dichloromethane containing 0.5% triethylamine. The isolated material was dissolved in 2N hydrochloric acid in methanol and heated under reflux overnight. The solvent was removed in vacuo and the resulting solid was redissolved in water. The pH was adjusted to ~7 with sodium bicarbonate, and the mixture was extracted with ethyl acetate. Concentration and purification by silica gel preparative thin layer chromatography eluting with 5% methanol in dichloromethane containing 0.5% triethylamine gave 2 mg of benzazepine 30a: RP-LC MS: m/z calcd for $C_{19}H_{22}ClN_2O_3S^+$=393.1; found m/z=393.1 (M+1)$^+$.

Method 32

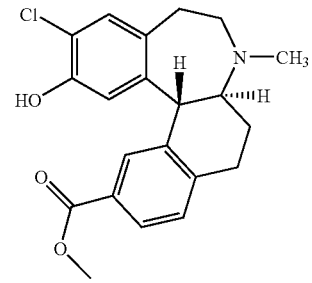

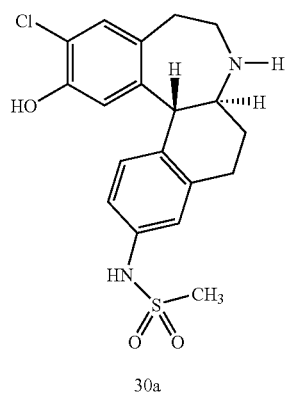

A solution of 1.0 g of amide 31c was heated under reflux in 2N HCl for 2 h. The solvent was removed in vacuo and the residue was dissolved in methanol. After addition of 0.50 ml of concentrated sulfuric acid, the solution was heated under reflux overnight. The solvent was evaporated in vacuo. The residue was dissolved in dichloromethane and washed with concentrated sodium bicarbonate solution. The organic layer was dried over sodium sulfate and the solvent was evaporated to give 0.9 gram of 32: RP-LC MS: m/z calcd for $C_{21}H_{23}ClNO_3^+$=372.1; found m/z=372.1 (M+1)$^+$.

Method 33

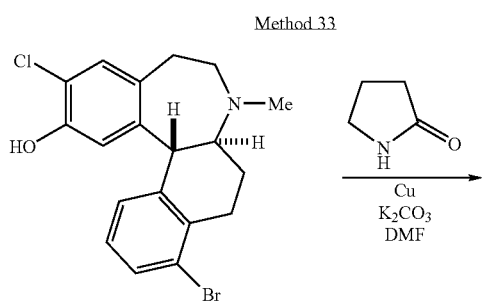

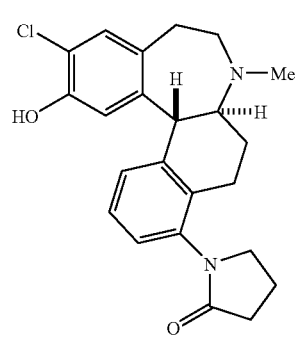

To 0.15 g (0.381 mmol) the bromo compound 3a dissolved in 2 mL of DMF was treated with 0.1 mL of 2-pyrrolidinone, 0.5 g (5 eq) copper powder and 0.1 g (2 eq) of potassium carbonate. The contents were heated in a sealed tube at 150° C. for 48 hours. The reaction mixture was cooled, passed through a short pad of celite and washed several times with ethyl acetate. The solvent was removed in vacuo and the product was isolated by preparative TLC eluting with 10% methanol in dichloromethane to give 0.037 g of the desired lactam: ES MS: m/z calcd for $C_{23}H_{26}ClN_2O_2^+$=397.1; found m/z=397.1 (M+1)$^+$ Method 34:

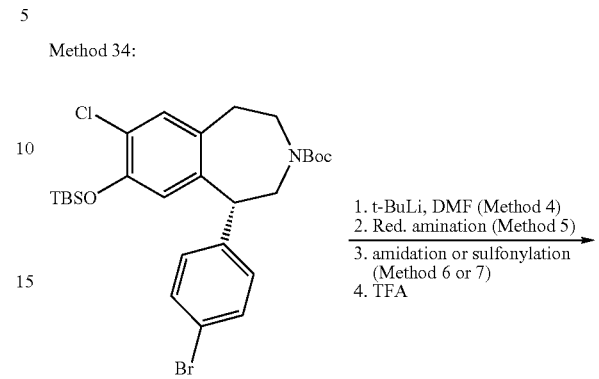

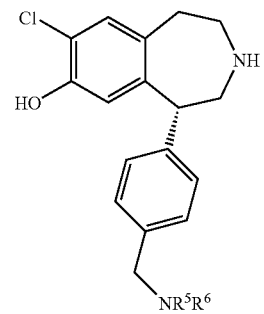

The following compounds could be prepared according to the above scheme using methods 4-7 as appropraite, followed by deprotection of the benzazepine nitrogen with trifluoroacetic acid:

| Compound | Compd # | Mol. Formula | Calc. MS | Found (M + 1) |
|---|---|---|---|---|
|  | 34a1 | $C_{22}H_{27}ClN_2O_3S$ | 435 | 435 |

-continued

| Compound | Compd # | Mol. Formula | Calc. MS | Found (M + 1) |
|---|---|---|---|---|
| (structure) | 34a2 | $C_{23}H_{27}ClN_2O_2$ | 399 | 399 |
| (structure) | 34a3 | $C_{26}H_{29}ClN_2O$ | 421 | 422 |

Method 35:

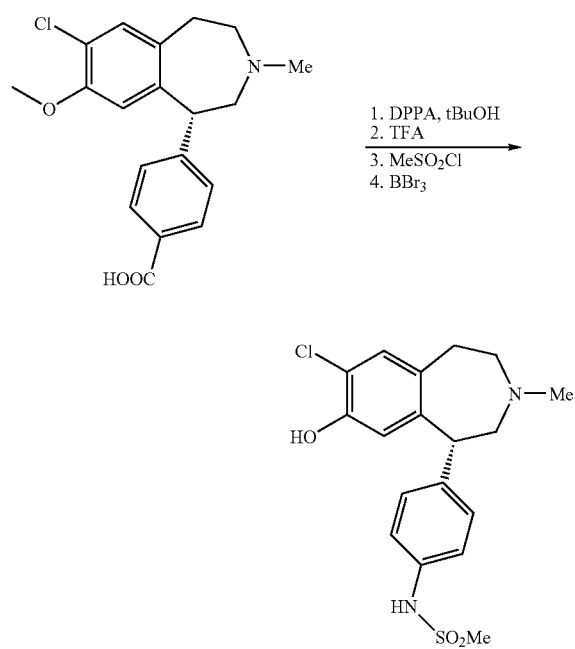

The acid (0.7 g, 2.02 mmol) was dissolved in 15 mL freshly distilled t-BuOH and 4 mL N-methylpyrrolidinone. It was treated with Hünig's base (0.35 mL, 1 eq) and diphenylphosphoryl azide (DPPA) (0.56 g, 1 eq). The mixture was heated to 90° C. overnight. The solvent was removed in vacuo. The residue was partioned between EtOAc and saturated NaHCO$_3$. The EtOAc layer was washed with brine and the solvent was removed to give a mixture of compounds. The desired NH-Boc compound was purified by prep TLC, followed by treatment with 30% TFA in dichloromethane to afford the desired aniline product. $^1$HNMR (CDCl$_3$) δ 2.40 (m, 1H) 2.40 (s, 3H) 2.70-3.20 (m, 5H) 3.60 (s, 3H) 4.28 (d, 1H, J=8.4 Hz) 6.28 (s, 1H) 6.68 (d, 2H, J=8.8 Hz) 6.98 (d, 2H, J=8.8 Hz) 7.10 (s, 1H). $^{13}$CNMR (CDCl$_3$) δ 35.70 48.50 49.48 57.15 58.12 63.98 114.01 116.46 120.30 130.08 131.77 133.04 134.66 145.43 146.02 153.99. Calcd. Mass for $C_{18}H_{21}ClN_2O^+$: 317; found: 317.

The aniline (30 mg, 0.09 mmol) was treated with pyridine (50 mg, 7 eq), MeSO$_2$Cl (52 mg, 5 eq) and stirred for 3 h. EtOAc was added and the mixture was washed with NaHCO$_3$ and water. Prep TLC provided the desired product (28 mg). $^1$HNMR (CDCl$_3$) δ 2.38 (s, 3H) 2.42 (m, 1H) 2.60-3.00 (m, 5H) 3.00 (s, 3H) 3.60 (s, 3H) 4.20 (br s,1H) 6.28 (s, 1H) 7.20 (m, 5H).

The final deprotection of O-Me was carried out with BBr$_3$ according to The final deprotection of O-Me was carried out with BBr$_3$ according to Org. Synth., Collect. Vol. V, 412 (1973). to give 35a1: $^1$HNMR (CDCl$_3$) δ 2.35 (m, 1H) 2.38 (s, 3H) 2.42 (m, 1H) 2.60-3.00 (m, 5H) 3.10 (s, 3H) 4.20 (d, 1H, J=8.4 Hz) 6.30 (s, 1H). 7.20 (m, 5H). $^{13}$CNMR (DMSO) δ 34.06 47.50 48.00 57.00 5 61.98 116.20 116.96 120.30 129.08 130.10 133.54 136.20 138.85 144.20 151.99. Calcd. Mass for $C_{18}H_{21}ClN_2O_3S^+$:381; found: 381.

The following compound was prepared analogously to the above procedure:

| Structure | Cmpd # | Mol. Formula | Calcd Mass | Found (M + 1) |
|---|---|---|---|---|
| 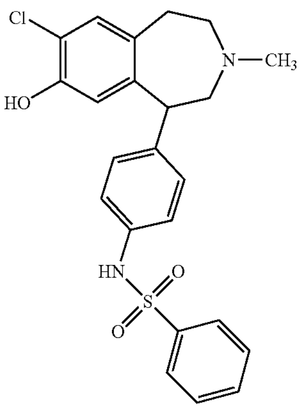 | 35a2 | $C_{23}H_{23}ClN_2O_3S$ | 443 | 443 |

Method 36:

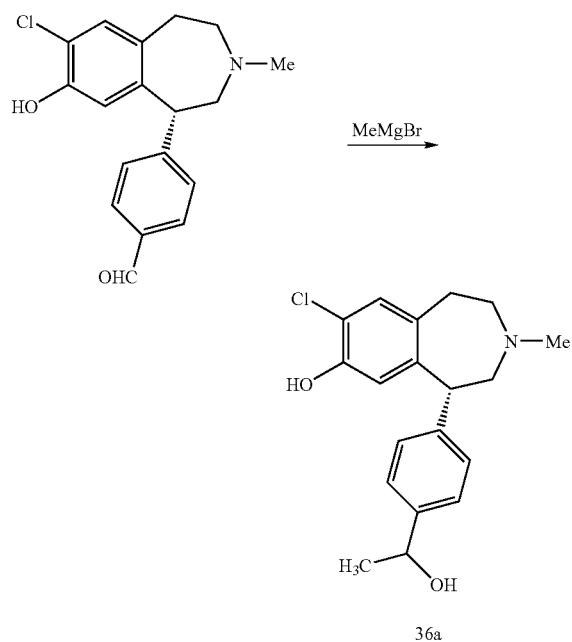

36a

The aldehyde (60 mg, 0.19 mmol) was treated with 1 mL tetrahydrofuran and 0.2 mL MeMgBr (3 M, 3 eq ) at 0° C. for 10 min. The reaction was quenched with water and extracted with EtOAc. The organic layer was dried and concentrated in vacuo to give 21 mg of the desired product, 36a$^1$HNMR (CDCl$_3$) δ 1.50 (d, 3H, J=6.4 Hz) 2.30 (m, 1H) 2.36 (s, 3H) 2.70-3.10 (m, 5H) 4.20 (m, 1H) 4.80 (m, 1H) 6.20 (d, 1H, J=6.6 Hz) 7.00-7.40 (m, 5H): Calcd. Mass for $C_{19}H_{22}ClNO_2^+$:332; found: 332.

The compounds of the present invention exhibit $D_1/D_5$ receptor antagonizing activity, which has been correlated with pharmaceutical activity for treating CNS disorders such as OCD, trichotillomania, metabolic disorders such as obesity, eating disorders such as hyperphagia, and diabetes. This utility is manifested by activity in the following assay.

Assay

Affinity values (Ki) of compounds at human $D_1$ and $D_2$ receptors were ascertained using radioligand binding competition assays. Ltk-cells expressing $D_1$ and $D_2$ (long variant) receptors were lysed in hypotonic buffer for membrane preparation. Membranes were incubated with various concentrations of test compound and 1 nM [3H] of a compound of formula III and 0.2 nM [3H] Methylspiperone for $D_1$ and $D_2$ assays, respectively. Non-specific binding was defined as binding in the presence of 10 micromolar of a compound of formula III for $D_1$ assays and 10 micromolar butaclamol for $D_1$ assays. Following incubation to equilibrium (1 hour at room temperature), bound radioligand was separated from free by rapid filtration. Bound radioactivity on the dried filters was quantified by liquid scintillation counting.

Results of the binding assay on compounds of the invention showed Ki ($D_1$) values of 0.2 to 2835 nM and Ki ($D_2$) values of 2.1 to >10,000.

Selectivity is determined by dividing Ki for D2 receptor by Ki for D1 receptor.

Compounds with Ki ($D_1$) values less than 100 nM are designated in the table below as D class compounds.

Compounds with Ki ($D_1$) values less than 50 nM but greater than 10 nM are designated in the table below as C class compounds.

Compounds of Ki ($D_1$) values less than 10 nM and a selectivity value greater than 100 are designated in the table below as B class compounds.

Preferred compounds of the invention have Ki ($D_1$) values less than 5nM and a selectivity value greater than 500 and are designated by the letter A in the table below.

A preferred embodiment of the claimed compounds is example 19b1 with a Ki ($D_1$) value of 0.45 and $D_2$:$D_1$ ratio value of 6642.

TABLE OF

$D_1$ Binding and Selectivity ($D_2$:$D_1$ Ratio)

| Ex. | $D_1$ binding and $D_2$:$D_1$ Selectivity |
|---|---|
| 5a14 | B |
| 5b46 | D |
| 6a6 | C |
| 6b1 | C |
| 7b7 | D |
| 8a3 | C |
| 8b11 | D |
| 13a2 | B |
| 13a6 | C |
| 15l | C |
| 18a6 | A |
| 18b15 | C |
| 19a6 | B |
| 19b5 | A |
| 20a33 | C |
| 20b30 | A |
| 21a1 | A |
| 22a2 | C |
| 22b1 | C |
| 14t | A |
| 19b1 | A |
| 5a1 | A |
| 7c18 | A |
| 24a1 | A |
| 24b2 | A |
| 20a8 | A |
| 29c | A |
| 21a2 | A |
| 20b5 | B |
| 5a50 | A |
| 19b31 | A |
| 5a38 | A |
| 13a7 | A |
| 24a2 | A |
| 20b6 | A |
| 24a3 | A |
| 19b32 | A |
| 19b23 | A |
| 13a12 | B |
| 20a7 | A |
| 13a21 | B |
| 18a1 | A |
| 23 | A |
| 25c | A |
| 27a | B |
| 13a24 | A |
| 35a1 | A |
| 13a20 | B |
| 13a19 | B |
| 18a4 | B |
| 19b24 | B |
| 13a14 | B |
| 18a8 | B |
| 13a16 | B |
| 30a | B |
| 5c16 | A |
| 6c26 | A |
| 7c16 | A |
| 8c33 | B |
| 13d1 | C |
| 34a2 | B |
| 35a2 | B |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by structural formula:

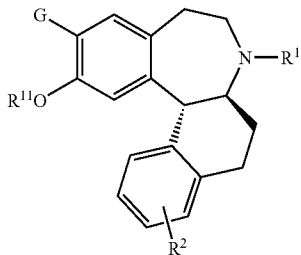

or a pharmaceutically acceptable salt of said compound, isomer or racemic mixture wherein G is hydrogen, halogen, alkyl, alkylthio, nitro, nitrile, hydroxy, alkoxy, alkylsulfinyl, alkylsulfonyl, trifluoromethyl or trifluoromethoxy;

$R^1$ is hydrogen, alkyl, allyl, cycloalkyl or cycloalkyl(alkyl);

$R^2$ is one substituent selected from the group consisting of trifluoromethoxy, aryl, $-NO_2$, $-NR^5R^6$, $-(CH_2)_{1-6}$ $-NR^5R^6$, $-N(R^6)C((R^7)(R^8))C(O)R^8$, $-CN$, heteroaryl, $-C(O)OR^8$, $-C(O)NR^3R^4$, $-C(R^7)(R^8)NR^5R^6$, $-C(R^7)=NOR^4$ and $-C(R^7)(R^8)OR^6$;

$R^3$ and $R^4$ are aryl, aralkyl, alkenyl, heterocyclyl, heteroaryl, cycloalkyl, cycloalkylalkyl, heteroaralkyl, heterocyclylalkyl, alkyl or hydrogen, or $R^3$, $R^4$ and the N to which they are attached can be joined together to form a ring selected from the group consisting of azetidine, azepane, indane, pyrrolidine, piperidine, piperazine, morpholine and

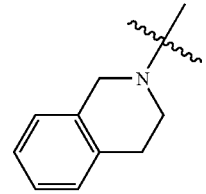

wherein said ring is unsubstituted or optionally substituted with one to four $R^{10}$ moieties;

$R^5$ is hydrogen, alkyl, alkenyl, aryl, aralkyl, cycloalkyl, heteroaralkyl, $-C(O)NR^3R^4$, $-S(O)_2NR^3R^4$, $-S(O)_2R^8$, $-C(O)R^8$, $-C(O)OR^8$ or $-R^9$;

$R^6$ is hydrogen, alkyl, aryl, aralkyl, cycloalkyl, cycloalkylalkyl, heteroaralkyl, heterocyclylalkyl, heterocyclyl or heteroaryl, or $R^5$, $R^6$ and the N to which they are attached can be joined together to form a ring selected from the group consisting of azetidine, azepane, indane, pyrrolidine, piperidine, piperazine, morpholine and

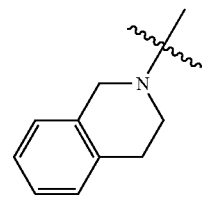

wherein said ring is unsubstituted or optionally substituted with one to four $R^{10}$ moieties;

$R^7$ is hydrogen, alkyl, aryl or aralkyl;

$R^8$ is hydrogen, aryl, alkyl, aralkyl, cycloalkyl, cycloalkylalkyl, heterocyclyl or heteroaryl;

$R^9$ is alkoxyalkyl, alkoxyaryl, alkoxyheteroaryl or alkoxyaralkyl;

$R^{10}$ is 1 to 4 substituents which can be the same or different, each $R^{10}$ being independently selected from the group consisting of alkyl, aryl, aralkyl, heteroaryl, heteroaralkyl, hydroxy, hydroxyalkyl, alkoxy, aryloxy, aralkoxy, acyl, aroyl, halogen, nitro, cyano, carboxy, alkoxycarbonyl, alkoxycarbonylalkylenyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, trifluoromethyl, $Y_1Y_2N-$, $Y_1Y_2N$-alkyl-, $Y_1C(O)N-$, $Y_1Y_2NC(O)-$ and $Y_1Y_2NS(O)_2-$, wherein $Y_1$ and $Y_2$ may be the same or different and are independently selected from the group consisting of hydrogen, alkyl, aryl, and aralkyl or two $R^{10}$ groups on adjacent carbons can be joined together to form a methylenedioxy or ethylenedioxy group; and $R^{11}$ is hydrogen or alkyl;

wherein each of said alkyl, allyl, alkylenyl, aryl, aralkyl, alkoxy, aryloxy, aralkoxy, acyl, aroyl, alkoxyalkyl, heterocyclylalkyl, heteroaryl, heteroaralkyl, hydroxyalkyl, cycloalkylalkyl, heterocyclyl and cycloalkyl is unsubstituted or optionally substituted with one to four $R^{10}$ moieties, where two adjacent $R^{10}$ groups can be joined together to form a methylenedioxy or ethylenedioxy group.

2. The compound according to claim 1 wherein $R^{11}$ is hydrogen.

3. The compound according to claim 1 wherein G is halogen.

4. The compound according to claim 1 wherein G is chloro.

5. The compound according to claim 1 wherein $R^1$ is hydrogen or alkyl.

6. The compound according to claim 1 wherein $R^1$ is hydrogen or methyl.

7. The compound according to claim 1 wherein G is halogen, $R^1$ is alkyl and $R^{11}$ is hydrogen.

8. The compound according to claim 7 wherein G is chloro, $R^1$ is methyl.

9. The compound according to claim 1 wherein
$R^2$ is $-CH_2-NR^5R^6$;
$R^5$ is hydrogen;
and $R^6$ is

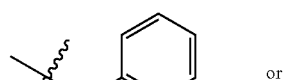  or  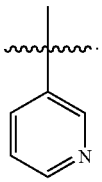

10. The according to claim 1 wherein
$R^2$ is $-CH_2-NR^5R^6$;
$R^5$ is $C(O)CH_3$;
and $R^6$ is

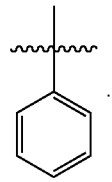

11. The compound according to claim 1 wherein
$R^2$ is $-CH_2-NR^5R^6$;
$R^5$ is benzyl;
and $R^6$ is

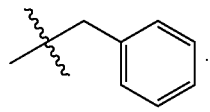

12. The compound according to claim 1 wherein
$R^2$ is $-CH_2-NR^5R^6$;
$R^5$ is $-S(O)_2$-methyl;
and $R^6$ is

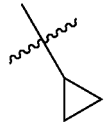

13. The compound according to claim 1 wherein
$R^2$ is $-CH_2-NR^5R^6$;
$R^5$ is $-S(O)_2$-methyl;
and $R^6$ is

14. The compound according to claim 1 wherein
$R^2$ is $-CH_2-NR^5R^6$;
$R^5$ is $-C(O)NH$-ethyl;
and $R^6$ is

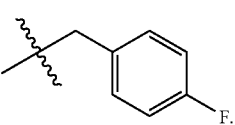

15. The compound according to claim 1 wherein
R² is —CH₂—NR⁵R⁶;
R⁵ is —C(O)NH-isopropyl;
and R⁶ is
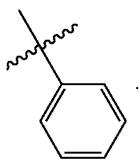
16. The compound according to claim 1 wherein R² is selected from the group consisting of
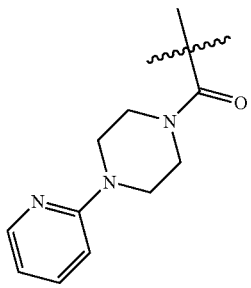 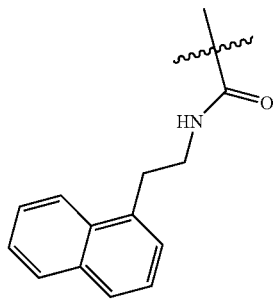
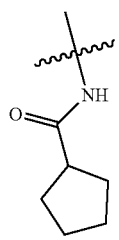 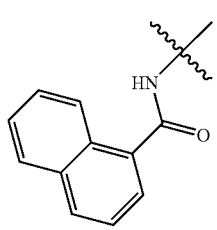
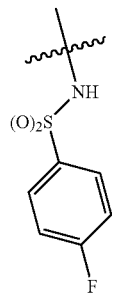 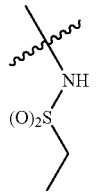
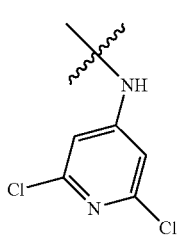 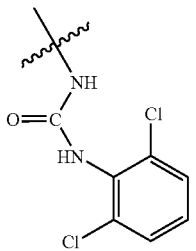 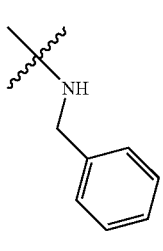
-continued
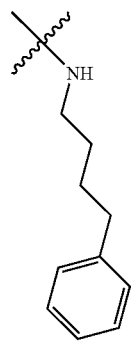 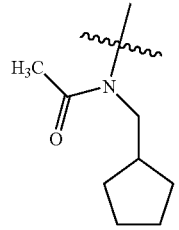 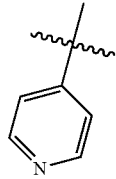
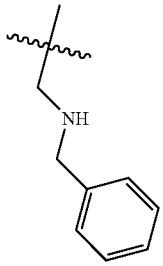 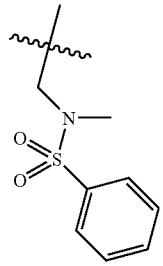 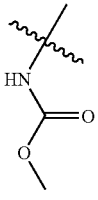
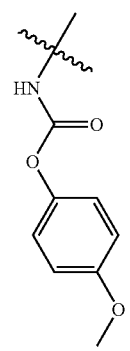 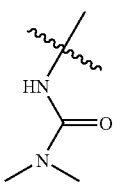 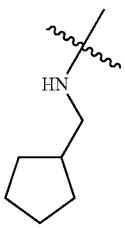
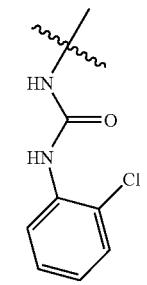 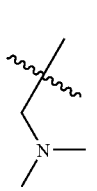 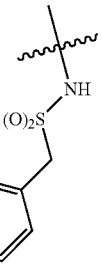
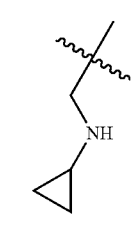 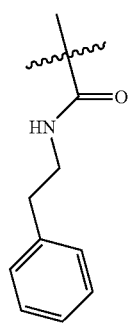 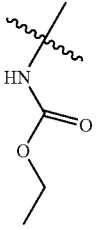

-continued
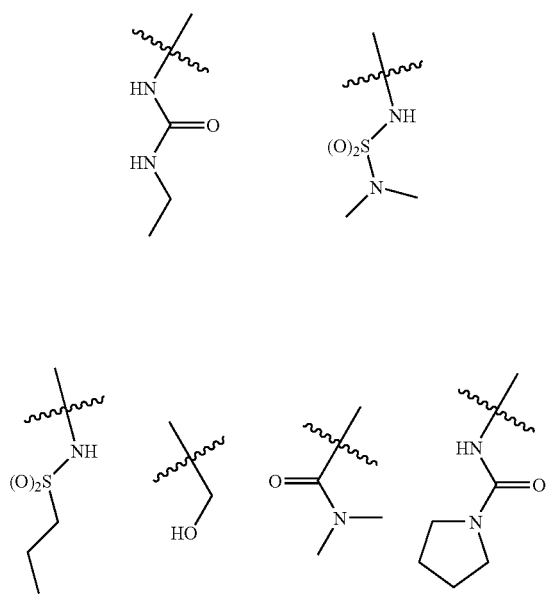
-continued
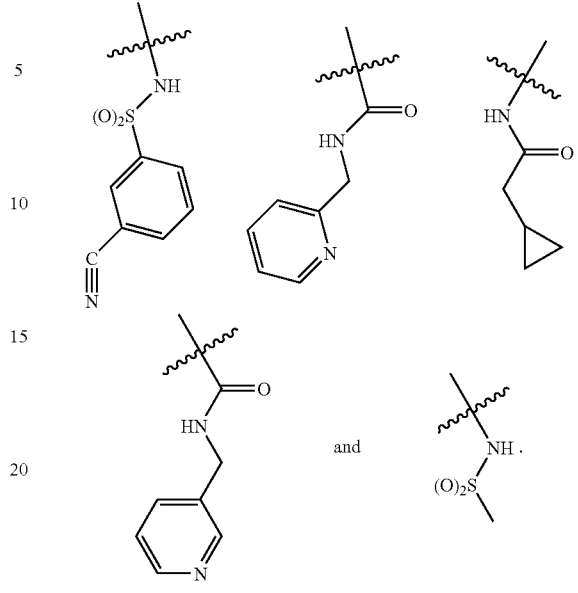
17. The compound according to claim 1 wherein $R^2$ is selected from the group consisting of:
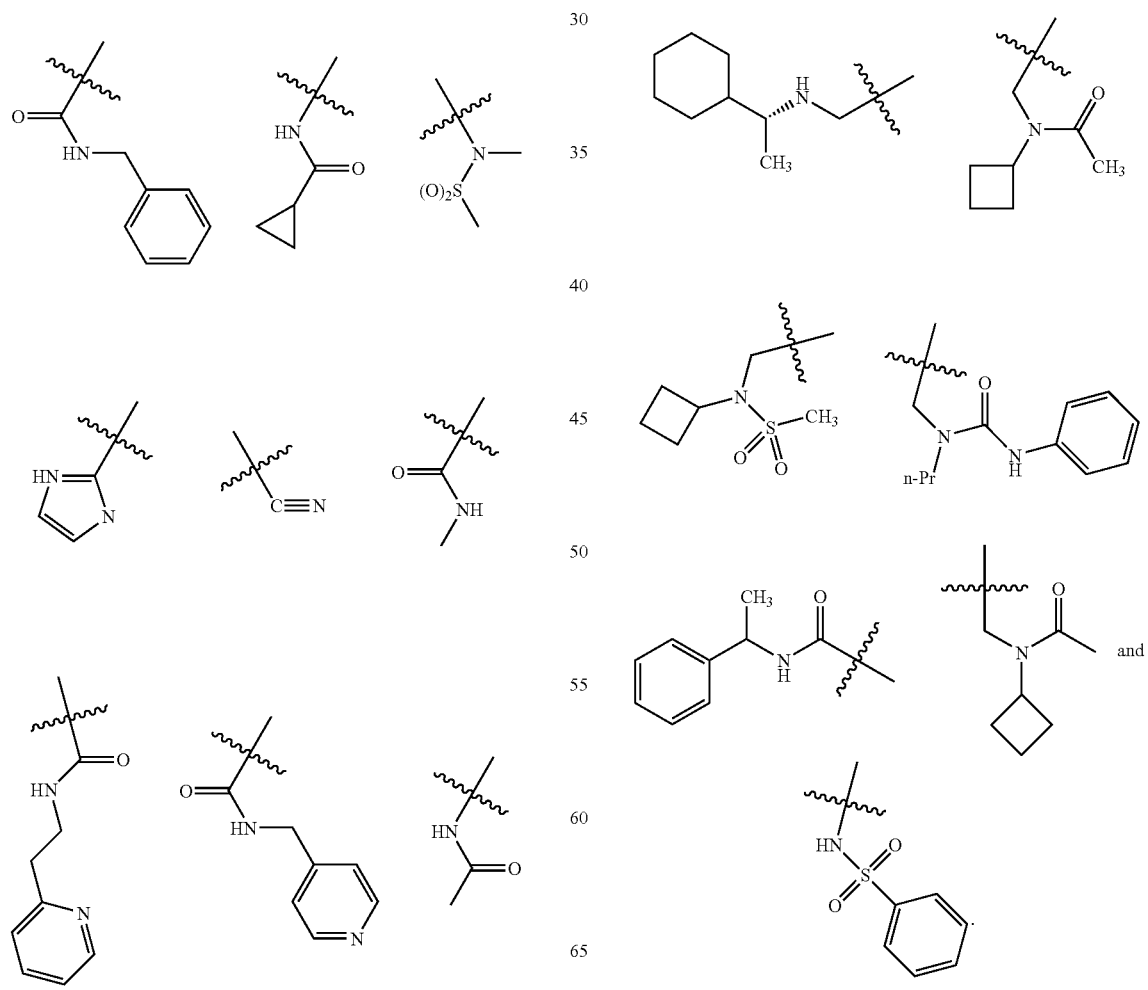

18. A compound selected from the group consisting of:
5a14
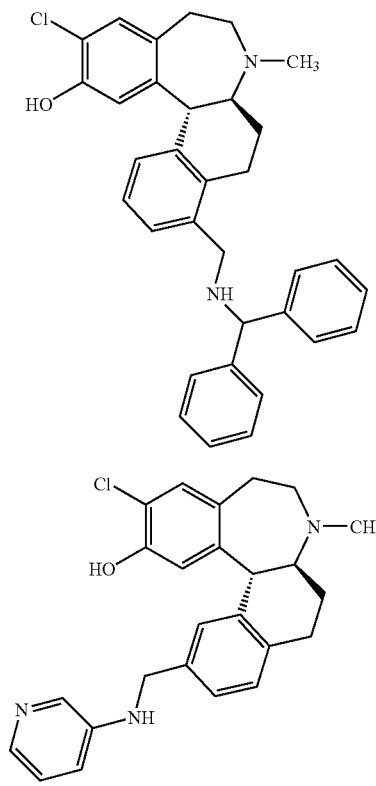
5b46
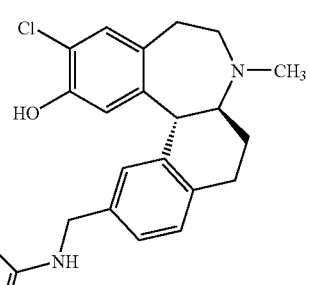
6a6
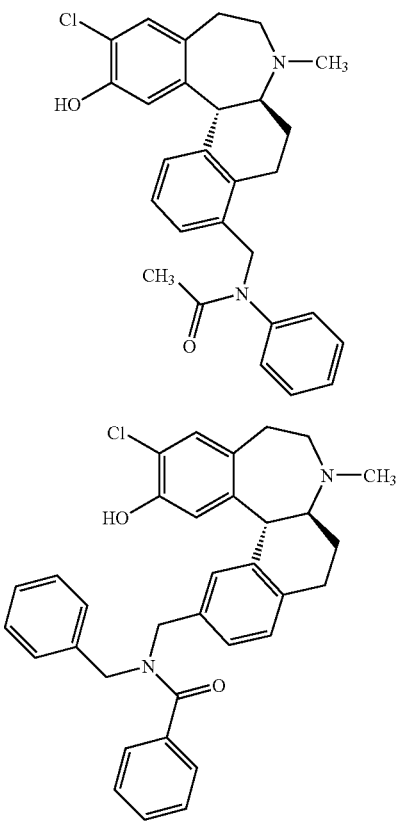
6b1
7b7
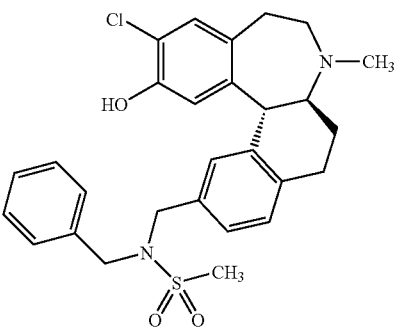
8a3
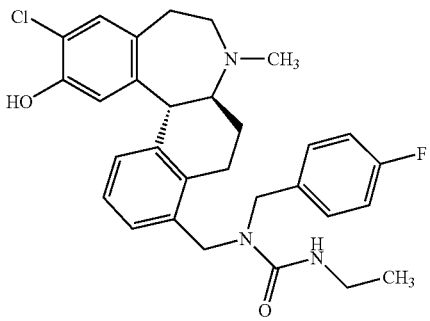
8b11
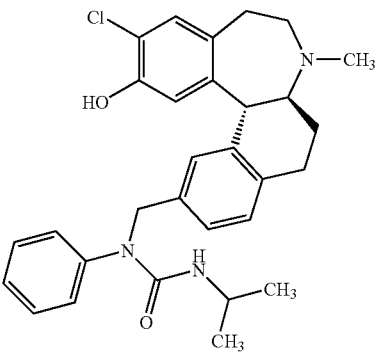
13a2
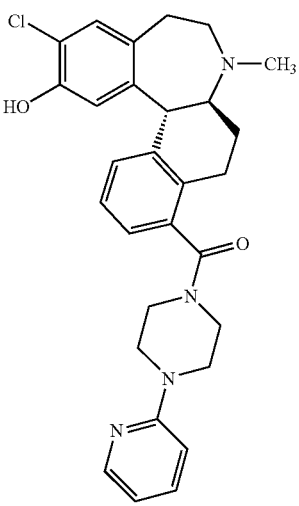

| 307 -continued | 308 -continued |
|---|---|
| 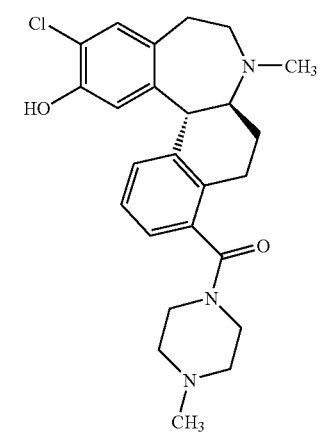 13a6 | 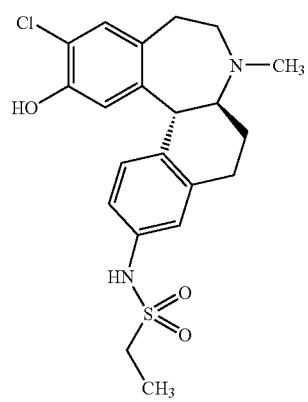 19b5 |
| 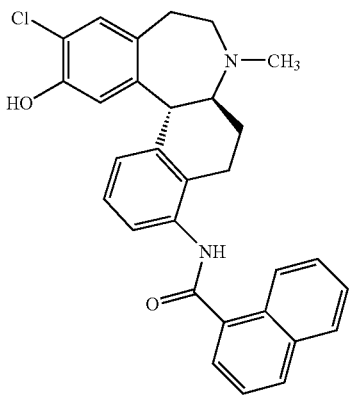 18a6 | 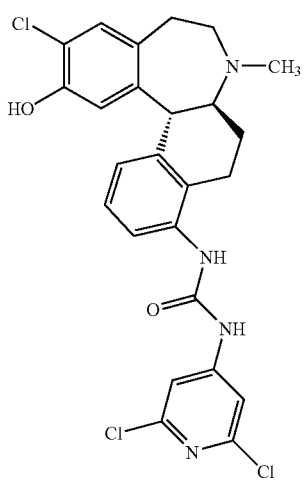 20a33 |
| 18b15 | |
| 19a6 | 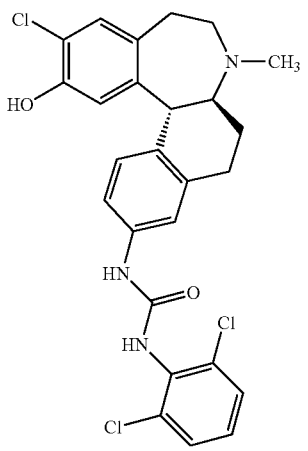 20b30 |
| 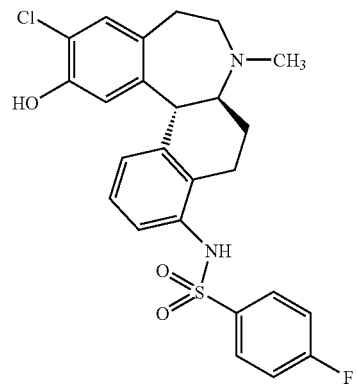 | |

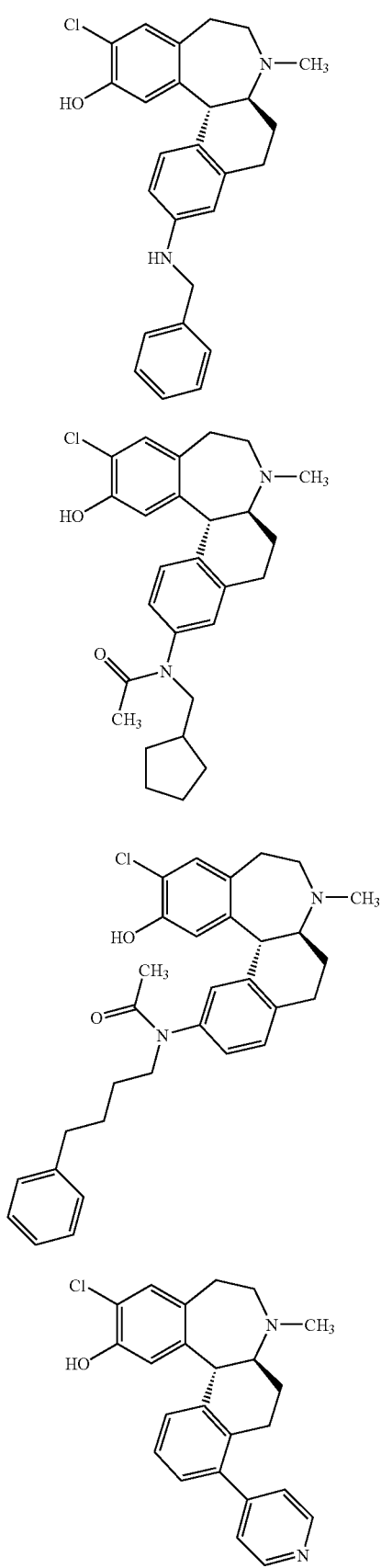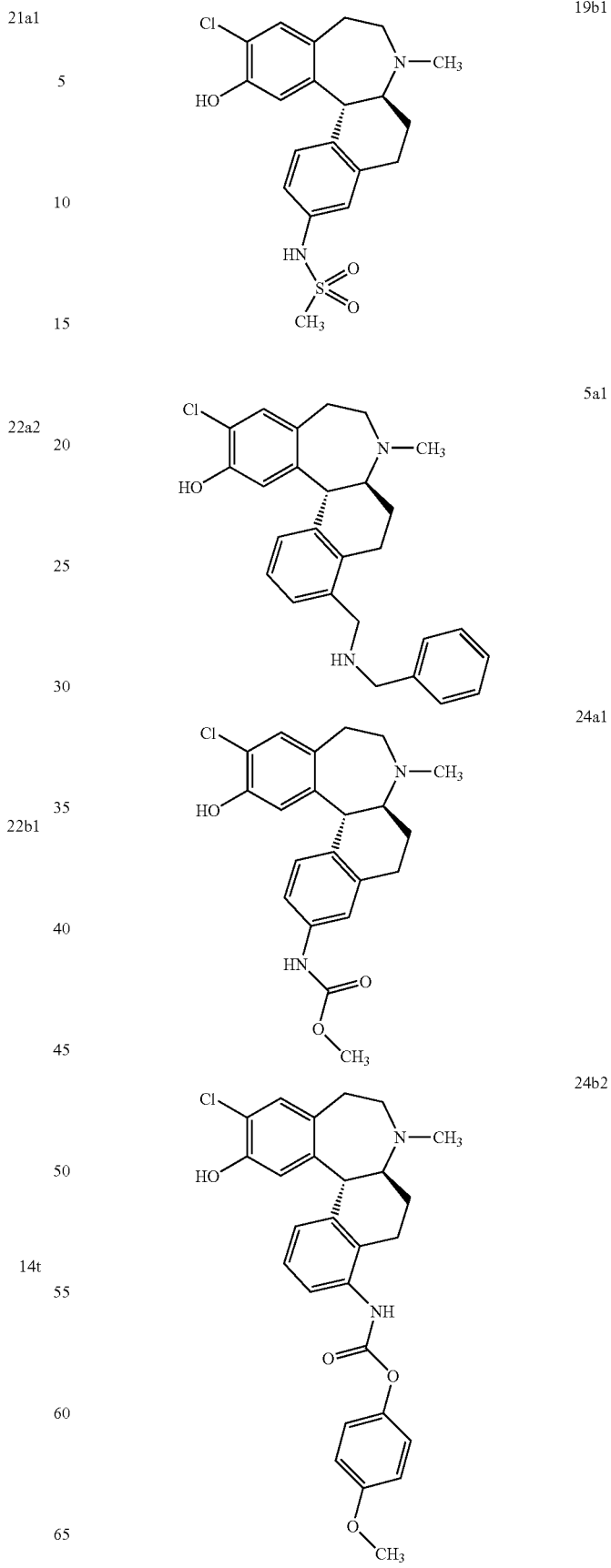

| 311 -continued | | 312 -continued | |
|---|---|---|---|
| 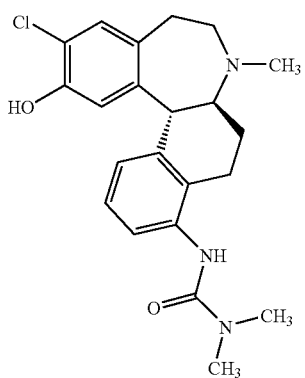 | 20a8 | 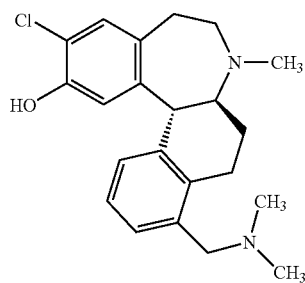 | 5a50 |
| 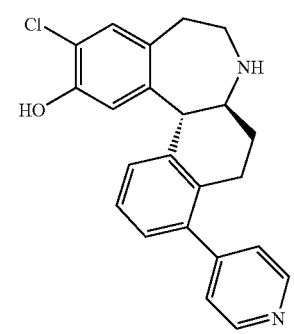 | 29c | 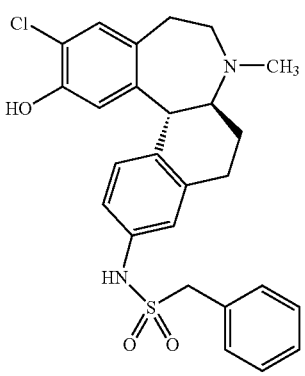 | 19b31 |
| 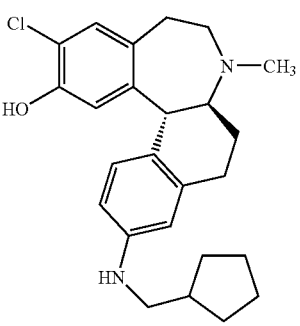 | 21a2 | 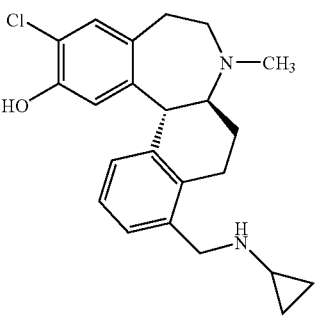 | 5a38 |
| 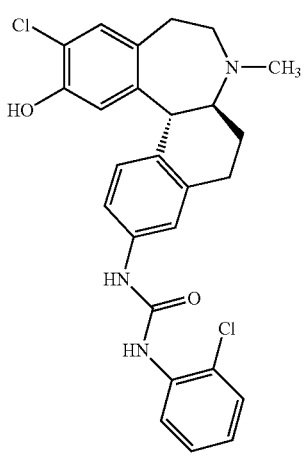 | 20b5 | 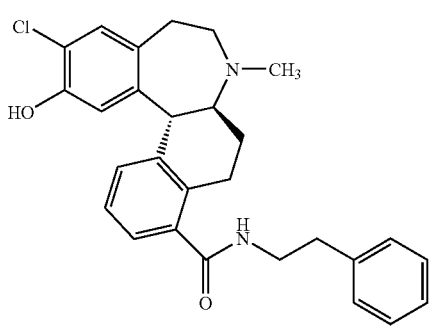 | 13a7 |
| | | 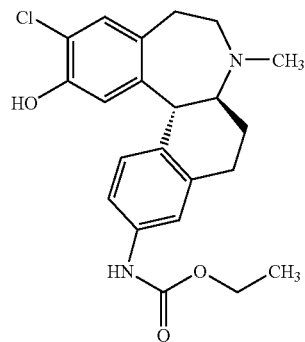 | 24a2 |

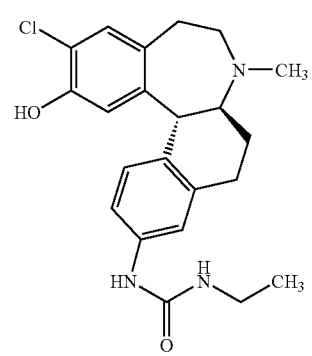
20b6
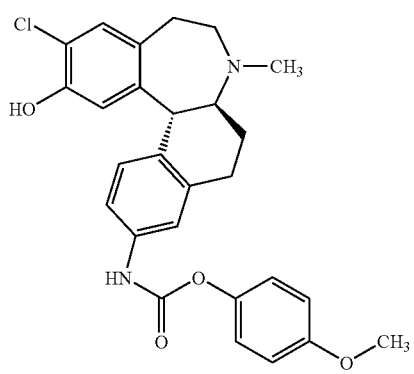
24a3
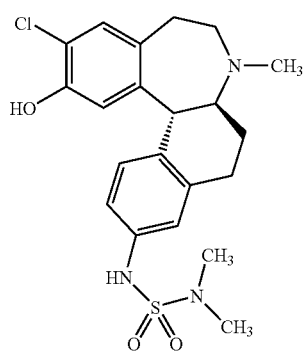
19b32
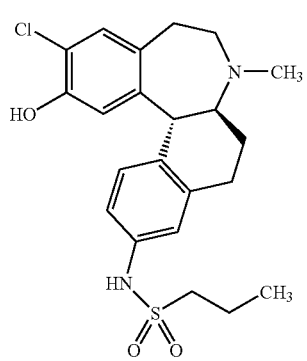
19b23
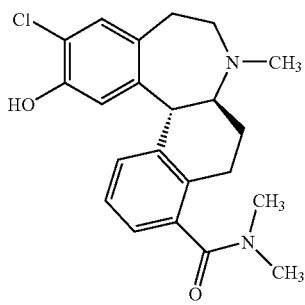
13a12
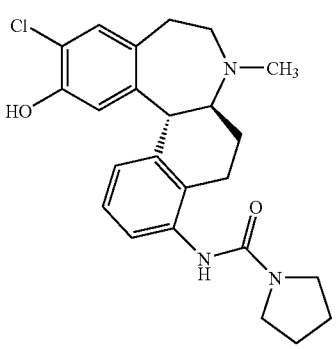
20a7
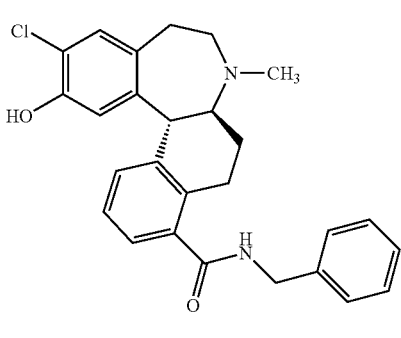
13a21
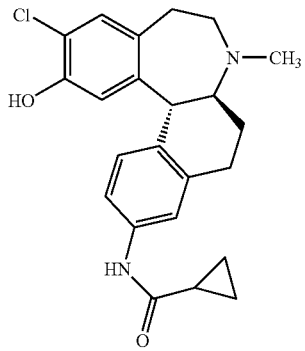
18a1
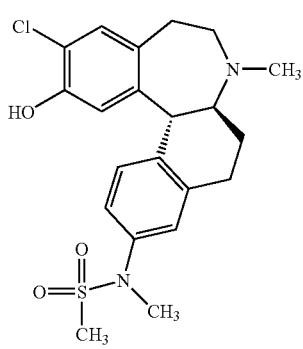
23

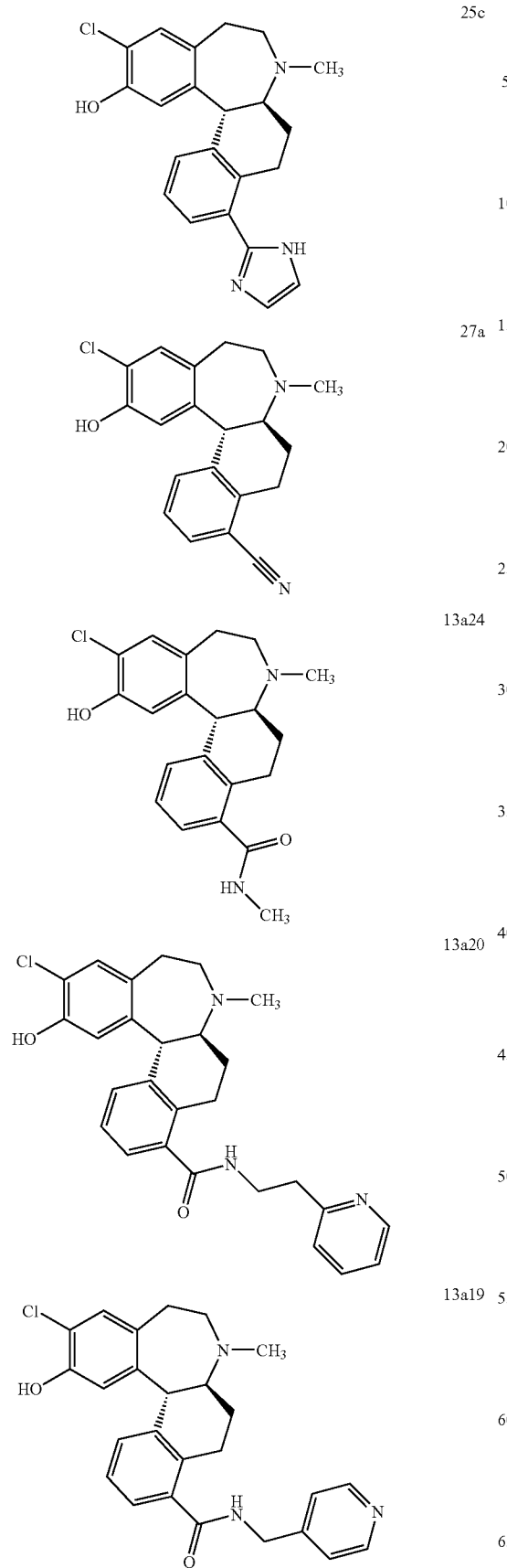
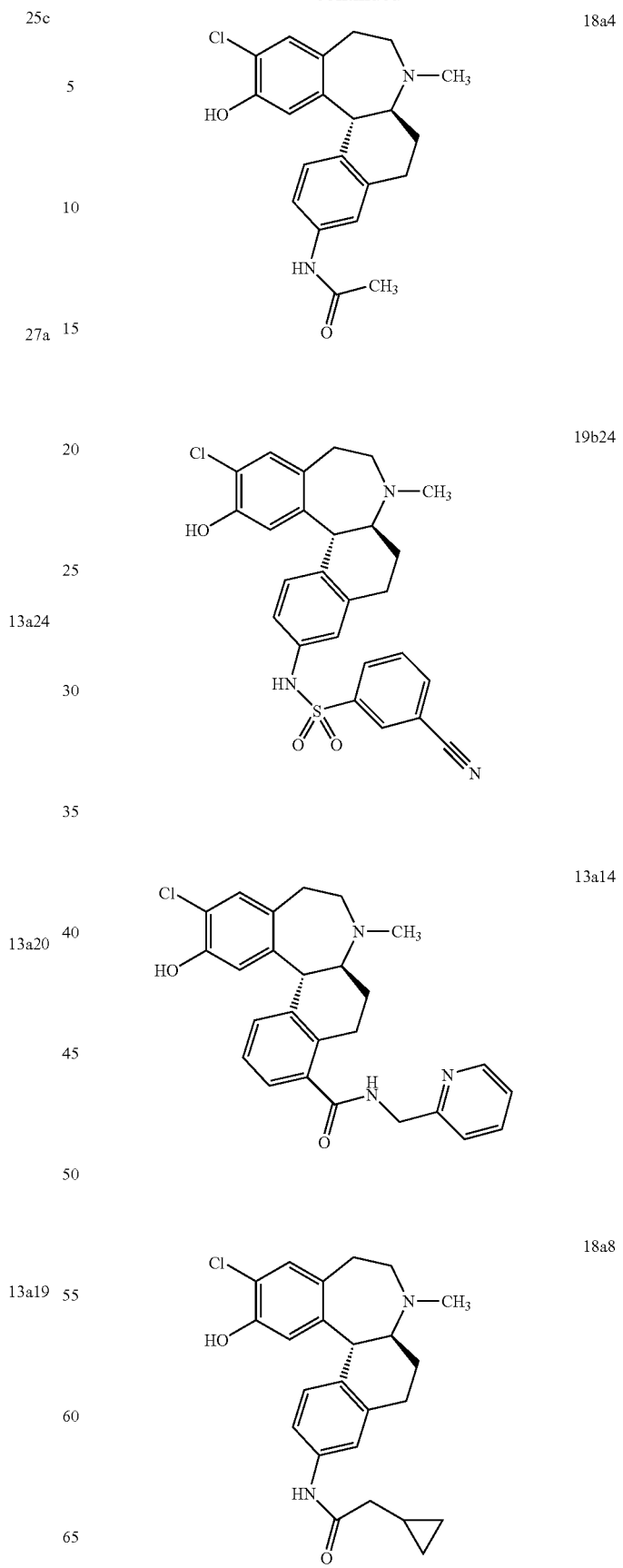

-continued

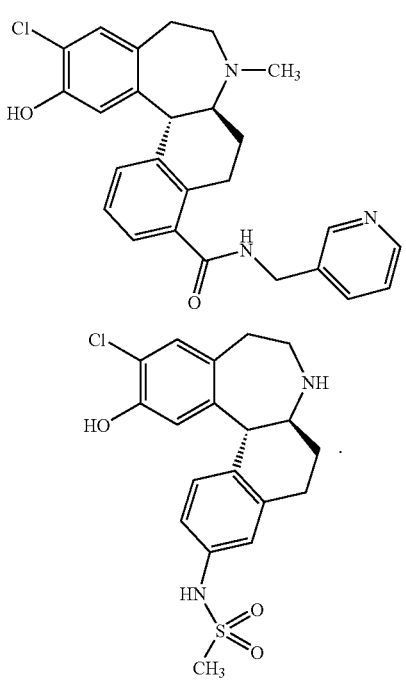

or a pharmaceutically acceptable salt thereof.

19. A method of treating an eating disorder comprising administering to a patient a therapeutically effective amount of at least one compound of claim 1, or a pharmaceutically acceptable salt of said compound, to a patient in need of such treatment.

20. A method of treating an eating disorder comprising administering to a patient a therapeutically effective amount of at least one compound of claim 18, or a pharmaceutically acceptable salt of said compound, to a patient in need of such treatment.

21. The method of claim 19 wherein said eating disorder is hyperphagia.

22. The method of claim 20 wherein said eating disorder is hyperphagia.

23. A pharmaceutical composition comprising a therapeutically effective amount of at least one compound of claim 1, or a pharmaceutically acceptable salt of said compound, in combination with at least one pharmaceutically acceptable carrier.

24. A pharmaceutical composition comprising a therapeutically effective amount of at least one compound of claim 18, or a pharmaceutically acceptable salt of said compound, in combination with at least one pharmaceutically acceptable carrier.

25. A process for making a pharmaceutical composition comprising combining at least one compound of claim 1, or a pharmaceutically acceptable salt thereof, and at least one pharmaceutically acceptable carrier.

26. A process for making a pharmaceutical composition comprising combining at least one compound of claim 18, or a pharmaceutically acceptable salt thereof, and at least one pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,504,391 B2 | Page 1 of 1 |
| APPLICATION NO. | : 10/850530 | |
| DATED | : March 17, 2009 | |
| INVENTOR(S) | : Duane A. Burnett et al. | |

It is certified that error appears in the above-identified patent and that said Letters Patent is hereby corrected as shown below:

Claim 1, col. 92, line 36: Please correct "-OCH3" to -- -OCF3--.

Signed and Sealed this

Nineteenth Day of January, 2010

David J. Kappos
*Director of the United States Patent and Trademark Office*